(12) United States Patent
Wang et al.

(10) Patent No.: US 10,732,017 B2
(45) Date of Patent: Aug. 4, 2020

(54) TOMOGRAPHY APPARATUS, MULTI-PHASE FLOW MONITORING SYSTEM, AND CORRESPONDING METHODS

(71) Applicant: UNIVERSITY OF LEEDS, Leeds, Yorkshire (GB)

(72) Inventors: Mi Wang, Leeds (GB); Jiabin Jia, Central Scotland (GB); Yousef Faraj, Huddersfield (GB); Qiang Wang, Leeds (GB)

(73) Assignee: UNIVERSITY OF LEEDS, Leeds (GB)

( * ) Notice: Subject to any disclaimer, the term of this patent is extended or adjusted under 35 U.S.C. 154(b) by 598 days.

(21) Appl. No.: 15/511,155

(22) PCT Filed: Sep. 15, 2015

(86) PCT No.: PCT/GB2015/052672
§ 371 (c)(1),
(2) Date: Mar. 14, 2017

(87) PCT Pub. No.: WO2016/042317
PCT Pub. Date: Mar. 24, 2016

(65) Prior Publication Data
US 2017/0261357 A1      Sep. 14, 2017

(30) Foreign Application Priority Data

Sep. 15, 2014    (GB) .................................. 1416287.9

(51) Int. Cl.
*G01F 1/58*    (2006.01)
*G01F 1/64*    (2006.01)
(Continued)

(52) U.S. Cl.
CPC ................ *G01F 1/584* (2013.01); *G01F 1/58* (2013.01); *G01F 1/64* (2013.01); *G01F 1/74* (2013.01);
(Continued)

(58) Field of Classification Search
CPC . G01F 15/02; G01F 15/18; G01F 1/58; G01F 1/584; G01F 1/64; G01F 1/74; G01F 1/88; G01N 27/07
(Continued)

(56) References Cited

U.S. PATENT DOCUMENTS 3,177,709 A * 4/1965 Fischer ..................... G01F 1/58
                                                    73/861.16
3,834,232 A * 9/1974 Gruner ..................... G01F 1/584
                                                    73/861.12
(Continued)

FOREIGN PATENT DOCUMENTS

CN        201476825 U     5/2010
EP        2343538 A2      7/2011
(Continued)

OTHER PUBLICATIONS

Deng et al., Fusion research of Electrical Tomography with other sensors for two-phase flow measurement, 2012, Measurement Science Review (Year: 2012).*
(Continued)

*Primary Examiner* — John Fitzgerald
*Assistant Examiner* — Truong D Phan
(74) *Attorney, Agent, or Firm* — Patterson Thuente Pedersen, P.A.

(57) ABSTRACT

A flow monitoring system is described for monitoring flow of a mixed-phase sample comprising at least a first phase and a second phase having different electrical conductivities, the second phase being a liquid or a gas and substantially
(Continued)

electrically non-conductive and the first phase being a liquid and having a conductivity higher than the second phase. The system comprises: a conduit through which the mixed-phase sample can be arranged to flow; tomography apparatus arranged to generate tomography data indicative of at least a first conductivity profile of at least a portion of a first cross section of the mixed phase sample when flowing through the conduit; a flow meter arranged to detect flow of the first phase though the conduit and provide a flow signal indicative of a flow velocity of the first phase; and processing means adapted to calculate, from said data, a fraction of said first cross section occupied by the first phase, and calculate, from said fraction and said flow signal, a volumetric flow rate of the first phase through the conduit.

19 Claims, 24 Drawing Sheets

(51) Int. Cl.
| | |
|---|---|
| G01F 1/74 | (2006.01) |
| G01F 1/88 | (2006.01) |
| G01F 15/02 | (2006.01) |
| G01F 15/18 | (2006.01) |
| G01N 27/07 | (2006.01) |

(52) U.S. Cl.
CPC ............... *G01F 1/88* (2013.01); *G01F 15/02* (2013.01); *G01F 15/18* (2013.01); *G01N 27/07* (2013.01)

(58) Field of Classification Search
USPC .......................................... 73/861.12–861.15
See application file for complete search history.

(56) References Cited

U.S. PATENT DOCUMENTS

| | | | | |
|---|---|---|---|---|
| 4,346,604 A * | 8/1982 | Snook | ....................... | G01F 1/58 73/861.12 |
| 4,459,858 A * | 7/1984 | Marsh | ....................... | G01F 1/58 73/861.12 |
| 4,707,658 A | 11/1987 | Frahm et al. | | |
| 5,269,191 A * | 12/1993 | Wada | ....................... | G01F 1/584 73/861.11 |
| 5,807,251 A * | 9/1998 | Wang | ....................... | A61B 5/0536 600/407 |
| 6,803,775 B2 * | 10/2004 | Sanchez | ............. | G01N 33/2852 324/515 |
| 6,940,286 B2 | 9/2005 | Wang et al. | | |
| 9,163,967 B2 * | 10/2015 | Lucas | ....................... | G01F 1/588 |
| 2004/0130338 A1 * | 7/2004 | Wang | ....................... | G01N 27/20 324/694 |
| 2007/0039398 A1 * | 2/2007 | Conrady | ................. | G01F 1/584 73/861.12 |
| 2008/0319685 A1 * | 12/2008 | Xie | ....................... | G01N 22/00 702/45 |
| 2010/0089171 A1 * | 4/2010 | Voigt | ....................... | G01F 1/584 73/861.12 |
| 2011/0166814 A1 * | 7/2011 | Mahalingam | .......... | G01N 27/02 702/77 |
| 2012/0235693 A1 | 9/2012 | Feng | | |
| 2012/0262176 A1 | 10/2012 | Czechowski et al. | | |
| 2013/0036817 A1 * | 2/2013 | Lucas | ....................... | G01F 1/588 73/32 R |
| 2013/0049770 A1 | 2/2013 | Basu et al. | | |
| 2013/0327154 A1 * | 12/2013 | Xie | ....................... | G01N 22/00 73/861.04 |
| 2014/0331783 A1 * | 11/2014 | Xie | ....................... | G01F 1/363 73/861.04 |
| 2015/0097589 A1 | 4/2015 | Orazem et al. | | |
| 2015/0145532 A1 | 5/2015 | Kersey et al. | | |

FOREIGN PATENT DOCUMENTS

| | | |
|---|---|---|
| WO | WO 2002/053029 A1 | 7/2002 |
| WO | WO 2009/030870 A1 | 3/2009 |
| WO | WO 2011/128656 A1 | 10/2011 |

OTHER PUBLICATIONS

PCT International Search Report and Written Opinion for PCT/GB2015/052671 dated Mar. 1, 2016, 19 pages.
Xiang Deng et al: "Fusion Research of Electrical Tomography with Other Sensors for Two-phase Flow Measurement", Measurement Science Review, vol. 12, No, 2, Jan. 1, 2012 (Jan. 1, 2012), pp. 62-67, XP055135675, ISSN: 1335-8871, DOI: 10.2478/v10048-012-0008-7.
Xiang Deng et al: "Theoretical study of vertical slug flow measurement by data fusion from electromagnetic flowmeter and electrical resistance tomography", Flow Measurement and Instrumentation, Butterworth-Heinemann, Oxford, GB, vol. 22, No. 4, Mar. 15, 2011 (Mar. 15, 2011), pp. 272-278, XP028224069, ISSN: 0955-5986, DOI: 10.1016/J.FLOWMEASINST.2011.03.007 [retrieved on Mar. 23, 2011].
Xiang Deng et al: "Study on fusion of electromagnetic flowmeter and ERT system in slug flow", 9th International Conference on Electronic Measurement & Instruments, 2009 : ICEMI '09 : Aug. 16-19, 2009, Beijing, China ; Proceedings, IEEE, Piscataway, NJ, USA, Aug. 16, 2009 (Aug. 16, 2009), pp. 1-365, XP031537858, ISBN: 978-1-4244-3863-1.
Image File Wrapper for U.S. Appl. No. 15/511,132, filed Mar. 14, 2017, Inventor(s): Wang et al.
PCT International Search Report and Written Opinion for PCT/GB2015/052671 dated Nov. 30, 2015, 15 pages.
Giguere R et al: "Characterization of slurry flow regime transitions by ERT", Chemical Engineering Research and Design, Part A, Institution of Chemical Engineers, XX, vol. 86, No. 9, Sep. 1, 2008 (Sep. 1, 2008) pp. 989-996, XP023980366, ISSN: 0263-8762, DOI: 10.1016/J.CHERD.2008.03.014 [retrieved on May 22, 2008].
Zozislaw Szczepanik et al: "Frequency Analysis of Electrical Impedance Tomography System", IEEE Transactions on Instrumentation and Measurement, IEEE Service Center, Piscataway, NJ, US, vol. 49, No. 4, Aug. 1, 2000 (Aug. 1, 2000), XP011025064, ISSN: 0018-9456.
Yi Li et al: "Gas/oil/water flow measurement by electrical capacitance tomography", Imaging Systems and Techniques (IST), 2012 IEEE International Conference on, IEEE, Jul. 16, 2012 (Jul. 16, 2012), pp. 83-88, XP032237187, DOI: 10.1109/IST.2012.6295481 ISBN: 978-1-4577-1776-5.
Search Report under Section 17(5) for UK Application No. 1416280.4, dated Mar. 10, 2015 (4 pages).
Search Report under Section 17(5) for UK Application No. 1416287.9, dated Mar. 17, 2015 (4 pages).
Kotre, "A sensitivity coefficient method for the reconstruction of electrical impedance tomograms," Clinical Physics and Physiological Measurement, vol. 10, No. 3, May 5, 1989, pp. 275-281.
Wang, "Inverse solutions for electrical impedance tomography based on conjugate gradients methods," Measurement Science and Technology, vol. 13, No. 1, Dec. 12, 2001, pp. 101-117.
Kotre, "EIT image reconstruction using sensitivity weighted filtered backprojection," Physiological Measurement vol. 15, Supplement 2A, May 1994, pp. A125-A136.
Xu et al., "Measurement of Solid Slurry Flow Via Correlation of Electromagnetic Flow Meter, Electrical Resistance Tomography and Mechanistic Modelling," Journal of Hydrodynamics, vol. 21, Issue 4, Aug. 2009, pp. 557-563.

\* cited by examiner (a) 2- or 3-phase flow direction
Flow with no solid particles (b) 2- or 3-phase flow direction
Flow with solid particles

TOMOGRAPHY APPARATUS, MULTI-PHASE FLOW MONITORING SYSTEM, AND CORRESPONDING METHODS

RELATED APPLICATIONS

The present application is a National Phase entry of PCT Application No. PCT/GB2015/052672, filed Sep. 15, 2015, which claims priority from GB Patent Application No. 1416287.9, filed Sep. 15, 2014, said applications being hereby incorporated by reference herein in their entirety.

FIELD OF THE INVENTION

Certain embodiments of the present invention relate to flow monitoring systems and methods for monitoring the flow of mixed-phase samples (in particular, although not exclusively, two-phase and three-phase samples). Certain embodiments of the invention relate to tomography apparatus and methods for measuring or monitoring flowing samples.

BACKGROUND

There are various applications in which it may be desirable to monitor the flow of multi-phase samples. For example, oil-in-water two-phase flows are often encountered in the petroleum industry. The measurement of phase flow rates is of particular importance for managing oil production and water disposal and/or water reinjection in the oil industry. The complexity of two and three-phase flow structures creates a challenge to flow measurements, and there is a constant need to improve flow monitoring systems in order to produce more accurate, more useful, and/or more reliable results, for example tomograms indicative of flow cross-sections with improved resolution and/or tomograms generated more rapidly/frequently with a particular data processing resource.

It is generally desirable to produce flow monitoring systems that are able to measure and provide a more accurate indication of various flow parameters of mixed-phase flows, and systems that are able to provide an indication of parameters that could not be deduced from previous systems and methods.

It is known for tomography apparatus to be used for monitoring flowing samples, and to produce tomograms indicative of a conductivity profile of a flowing sample across a conduit carrying sample, the apparatus employing arrays of electrodes distributed around the conduit in a wall. Such systems typically perform a plurality of measurements, using one pair of electrodes to drive a current through the flowing sample, and another pair of electrodes to measure a resultant voltage developed. From a large number of such measurements, using different pairs of electrodes, known calculation techniques are able to generate a tomogram indicative of the conductivity profile of a sample across the conduit bore. However, a problem with such systems is that samples material may be deposited on, or otherwise build up on the electrode contact surfaces. In general this build-up of material will generally increase the impedance of the electrode-sample connection/contact and can reduce the accuracy and/or resolution, or otherwise degrade the tomograms that could be generated from the measured data. This can be a particular problem in systems for use in the monitoring of two-phase sample flows, such as flows of oil mixed with water. Oil droplets, for example, may build up on the contact surfaces, degrading performance of the tomography apparatus as a whole.

BRIEF SUMMARY OF THE DISCLOSURE

It is an aim of embodiments of the present invention to obviate, mitigate, or solve at least partly, at least one of the problems associated with the prior art.

Certain embodiments of the invention aim to provide flow monitoring systems and methods able to produce more accurate information and/or more information on parameters associated with the flow of mixed-phase samples than were possible with the prior art.

Certain embodiments aim to provide tomography apparatus and methods which solve, at least partly, at least one of the problems associated with the prior art.

According to a first aspect of the present invention there is provided a flow monitoring system for monitoring flow of a mixed-phase sample comprising at least a first phase and a second phase having different electrical conductivities, the second phase being a liquid or a gas and substantially electrically non-conductive and the first phase being a liquid and having a conductivity higher than the second phase, the system comprising:

a conduit through which the mixed-phase sample can be arranged to flow;

tomography apparatus arranged to generate tomography data indicative of at least a first conductivity profile of at least a portion of a first cross section of the mixed phase sample when flowing through the conduit;

a flow meter arranged to detect flow (e.g. axial flow) of the first phase though the conduit and provide a flow signal indicative of a flow velocity (e.g. an axial flow velocity, or a mean axial flow velocity) of the first phase; and processing means (e.g. at least one processor, processing module, or processing unit) adapted to calculate (determine, ascertain), from said data, a fraction (e.g. a mean fraction) of said first cross section occupied by the first phase (or a volume fraction, e.g. a mean volume fraction, of the sample occupied by the first phase), and calculate, from said fraction and said flow signal, a volumetric flow rate (e.g. a mean volumetric flow rate) of the first phase through the conduit.

It will be appreciated that embodiments of the invention may use various types of tomography apparatus and techniques to generate tomography data. For example, certain embodiments use Electrical Resistance Tomography (ERT) apparatus/techniques, certain embodiments use Electrical Impedance Tomography (EIT) apparatus/techniques, and certain other embodiments may use alternative tomography apparatus/techniques suitable for obtaining the requisite data.

In certain embodiments the flow meter is an electromagnetic flow meter.

In certain embodiments said data is further indicative of a second conductivity profile of at least a portion of a second cross section of the mixed phase sample when flowing through the conduit.

In certain embodiments the planes of said first and second cross sections are parallel to each other.

In certain embodiments the tomography apparatus comprises a first array of electrodes arranged around said first cross section and a second array of electrodes arranged around said second cross section.

In certain embodiments the processing means is adapted to calculate (determine, ascertain) a volume fraction (e.g. a mean volume fraction) of the first phase in the sample using said data.

In certain embodiments the processing means is adapted to calculate a volumetric flow rate (e.g. a mean volumetric flow rate) of the first phase in the sample using said volume fraction and said signal.

In certain embodiments the processing means is adapted to calculate an axial velocity (e.g. a mean axial velocity) and a volume fraction (e.g. a mean volume fraction) of the second phase in the sample using said data.

In certain embodiments the processing means is adapted to calculate a volumetric flow rate (e.g. a mean volumetric flow rate) of the second phase in the sample using said axial velocity and volume fraction of the second phase.

In certain embodiments the mixed-phase sample comprises a third phase, the third phase being a liquid or a gas, being substantially electrically non-conductive, and having a density different from a density of the second phase, the system further comprising means (e.g. a density meter or sub-system) for measuring a density of the mixed-phase sample flowing through the conduit and generating density data indicative of the density of the mixed-phase sample.

In certain embodiments the processing means is adapted to calculate a volume fraction (e.g. a mean volume fraction) of the second and/or third phase in the sample using tomography data of the second phase in the sample and the volume fraction (e.g. a mean volume fraction) of the third phase in the sample using the tomography data and the density data.

In certain embodiments the processing means is adapted to calculate a volumetric flow rate (e.g. mean) of the first phase using (from) the tomography data and said signal, calculate a volumetric flow rate (e.g. mean) of the second phase using the tomography data, the density data, and said signal, and calculate a volumetric flow rate (e.g. mean) of the third phase using the tomography data and the density data.

In certain embodiments the second phase is a liquid and the third phase is a gas.

In certain embodiments said first phase is water and said second phase is an oil.

In certain embodiments the processing means is adapted to calculate a volume fraction (e.g. a mean volume fraction) of the second and/or third phase in the sample using tomography data.

In certain embodiments the processing means is adapted to calculate a volumetric flow rate (e.g. mean) of the first phase using (from) the tomography data and electromagnetic flow meter data.

In certain embodiments the processing means is adapted to measure flow-mix density using a flow-mixture density metre (e.g. a gradiomanometer), for example with a first pressure sensor arranged at a first height and a second pressure sensor arranged at a second height of said conduit.

In certain embodiments the processing means is adapted to calculate a volumetric flow rate (e.g. mean) of the third phase using data from tomography and the flow-mixture density meter (e.g. gradiomanometer).

In certain embodiments said first phase is water and said second phase is a gas and said the third phase is an oil.

In certain embodiments said conduit is arranged with its longitudinal axis substantially vertical, and the means for measuring a density comprises a first pressure sensor arranged at a first height and a second pressure sensor arranged at a second height, each pressure sensor being arranged to sense pressure of the flowing sample in the conduit at the respective height and provide a respective pressure signal, indicative of sample pressure, to the processing means.

In certain embodiments the system further comprises a temperature sensor arranged to sense a temperature of the sample flowing though the conduit and provide a temperature signal, indicative of said temperature, to the processing means.

In certain embodiments the processor is adapted to use the temperature signal and the tomography data to calculate a volume fraction of at least the first phase in the flowing sample (e.g. such that the calculated volume fraction may compensate for, or take into account, changes in conductivity of the first phase resulting from changes in temperature).

In certain embodiments the processor is adapted to use the temperature signal to calculate at least one of: volume fraction of one or more of said phases; flow velocity of one or more of said phases; and volume flow rate of one or more of said phases.

In certain embodiments the processing means is adapted to use the temperature signal and said flow signal to calculate a flow velocity of the first phase (e.g. such that the calculated flow velocity may compensate for, or take into account, changes in conductivity of the first phase resulting from changes in sample temperature).

In certain embodiments the system further comprises conductivity measuring means (e.g. a conductivity meter) arranged to measure an electrical conductivity of the first phase of the sample flowing through the conduit and provide a conductivity signal, indicative of the measured conductivity, to the processing means.

In certain embodiments the processor is adapted to use the conductivity signal and the tomography data to calculate a volume fraction of at least the first phase in the flowing sample (e.g. such that the calculated volume fraction may compensate for, or take into account, changes in conductivity of the first phase resulting from changes in ionic concentration).

In certain embodiments the processor is adapted to use the conductivity signal to calculate at least one of: volume fraction of one or more of said phases; flow velocity of one or more of said phases; and volume flow rate of one or more of said phases.

In certain embodiments the processing means is adapted to use the conductivity signal and said flow signal to calculate a flow velocity of the first phase (e.g. such that the calculated flow velocity may compensate for, or take into account, changes in conductivity of the first phase resulting from changes in ionic concentration).

In certain embodiments the conductivity measuring means comprises a chamber arranged in communication with the sample-containing volume of the conduit such that when the sample is flowing through the conduit, a portion of the sample collects in the chamber, a plurality of electrodes arranged to be in electrical contact with first phase material collected in the chamber, and current driving means and voltage measurement means connected to the plurality of electrodes and arranged to drive a current through the collected first phase material and measure a voltage developed across the first phase material.

In certain embodiments the conduit is arranged such that its longitudinal axis is substantially vertical, and said chamber is a side chamber extending radially outwards from the conduit.

In certain embodiments the first phase has a density higher than the second phase and the third phase, and said side chamber extends axially downwards such that first phase material collects in a lower portion of the chamber, said electrodes being located in said lower portion.

In certain embodiments the first phase has a density lower than the second phase and the third phase, and said side chamber extends axially upwards such that first phase material collects in an upper portion of the chamber, said electrodes being located in said upper portion.

In certain embodiments the conductivity measuring means further comprises a ground metal mesh screen arranged in the chamber to isolate the electric field effect of the up portion of the proximate the sample to the low portion of the collected sample proximate the electrodes In certain embodiments the conductivity measuring means further comprises a screen (e.g. a ground metal mesh screen) arranged in the chamber to separate a portion of the collected sample proximate the electrodes from a portion proximate the sample flowing in the conduit.

In certain embodiments the conductivity measuring means further comprises a tube connecting the chamber to the conduit, and a valve operable to selectively permit or prevent flow of sample material through said tube, for refreshing first phase material in said chamber.

In certain embodiments the tomography apparatus comprises:
a plurality of electrodes each having a respective contact surface arranged to be in electrical contact with a sample flowing through said conduit; and
measurement means connected to the plurality of electrodes and adapted to perform a plurality of measurements on a sample flowing through said conduit to generate said tomography data, each measurement comprising driving a current between a pair of said electrodes and measuring a voltage (a voltage developed) across another pair of said electrodes,
wherein at least a portion of each electrode contact surface slopes (or, in other words, curves, ramps, or extends) inwardly, toward a longitudinal axis of the conduit, along the longitudinal axis, whereby accumulation of deposits on each said portion may be at least partly inhibited by sample flow past each said portion.

In certain embodiments the system further comprises heating means operable to heat at least part of each electrode, wherein each contact surface is a surface of the respective said part.

In certain embodiments the system further comprises vibrating means operable to vibrate at least part of each electrode, wherein each contact surface is a surface of the respective said part.

In certain embodiments the tomography apparatus comprises:
a plurality of electrodes each having a respective contact surface arranged to be in electrical contact with a sample flowing through said conduit; and
measurement means connected to the plurality of electrodes and adapted to perform a plurality of measurements on a sample flowing through said conduit to generate said tomography data, each measurement comprising driving a current between a pair of said electrodes and measuring a voltage (a voltage developed) across another pair of said electrodes,
and further comprises heating means operable to heat at least part of each electrode, wherein each contact surface is a surface of the respective said part.

In certain embodiments the apparatus further comprises vibrating means operable to vibrate at least part of each electrode, wherein each contact surface is a surface of the respective said part.

In certain embodiments the tomography apparatus comprises:
a plurality of electrodes each having a respective contact surface arranged to be in electrical contact with a sample flowing through said conduit; and
measurement means connected to the plurality of electrodes and adapted to perform a plurality of measurements on a sample flowing through said conduit to generate said tomography data, each measurement comprising driving a current between a pair of said electrodes and measuring a voltage (a voltage developed) across another pair of said electrodes,
and further comprises vibrating means operable to vibrate at least part of each electrode, wherein each contact surface is a surface of the respective said part.

Another aspect of the present invention provides a flow monitoring method for monitoring flow of a mixed-phase sample comprising at least a first phase and a second phase having different electrical conductivities, the second phase being a liquid or a gas and substantially electrically non-conductive and the first phase being a liquid and having a conductivity higher than the second phase, the system comprising:
arranging the mixed-phase sample to flow through a conduit;
using tomography apparatus to generate tomography data indicative of at least a first conductivity profile of at least a portion of a first cross section of the mixed phase sample flowing through the conduit;
using a flow meter to detect flow (e.g. axial flow) of the first phase though the conduit and generate a flow signal indicative of a flow velocity (e.g. an axial flow velocity, or a mean axial flow velocity) of the first phase; and
calculating, from said data, a fraction (e.g. a mean fraction) of said first cross section occupied by the first phase (or a volume fraction of the sample occupied by the first phase), and calculating, from said fraction and said flow signal, a volumetric flow rate (e.g. a mean volumetric flow rate) of the first phase through the conduit.

Thus, the tomography apparatus may be used to calculate the second and/or third phase volume fraction.

In certain embodiments the mixed-phase sample comprises a third phase, the third phase being a liquid or a gas, being substantially electrically non-conductive, and having a density different from a density of the second phase, the method further comprising: measuring a density of the mixed-phase sample flowing through the conduit and generating density data indicative of the density of the mixed-phase sample.

In certain embodiments the method further comprises:
calculating a volume fraction (e.g. a mean volume fraction) of the second phase in the sample and the volume fraction (e.g. a mean volume fraction) of the third phase in the sample using the tomography data and the density data (and optionally the flow meter, e.g. electromagnetic flow meter, data).

Method features corresponding to the various apparatus features of embodiments of the first aspect of the invention may be incorporated in embodiments of this second aspect with corresponding advantage.

Another aspect of the invention provides tomography apparatus comprising:
a conduit having an interior volume (e.g. a bore) extending along a longitudinal axis and through which a fluid or mixed-phase sample may be arranged to flow;
a plurality of electrodes each having a respective contact surface arranged to be in electrical contact with a sample flowing through said interior volume; and measurement means connected to the plurality of electrodes and adapted to perform a plurality of measurements on a sample flowing through said interior volume, each measurement comprising driving a current between a pair of said electrodes and measuring a voltage (a voltage developed) across another pair of said electrodes, wherein at least a portion of each electrode contact surface slopes (or, in other words, curves, ramps, or extends) inwardly, toward the longitudinal axis, along the longitudinal axis, whereby accumulation of deposits on each said portion may be at least partly inhibited by sample flow past each said portion.

Another aspect of the invention provides tomography apparatus comprising:

a conduit having an interior volume (e.g. a bore) extending along a longitudinal axis and through which a fluid or mixed-phase sample may be arranged to flow;

a plurality of electrodes each having a respective contact surface arranged to be in electrical contact with a sample flowing through said interior volume; and measurement means connected to the plurality of electrodes and adapted to perform a plurality of measurements on a sample flowing through said interior volume, each measurement comprising driving a current between a pair of said electrodes and measuring a voltage (a voltage developed) across another pair of said electrodes, and further comprising heating means operable to heat at least part of each electrode, wherein each contact surface is a surface of the respective said part.

Another aspect of the present invention provides tomography apparatus comprising:

a conduit having an interior volume (e.g. a bore) extending along a longitudinal axis and through which a fluid or mixed-phase sample may be arranged to flow;

a plurality of electrodes each having a respective contact surface arranged to be in electrical contact with a sample flowing through said interior volume; and measurement means connected to the plurality of electrodes and adapted to perform a plurality of measurements on a sample flowing through said interior volume, each measurement comprising driving a current between a pair of said electrodes and measuring a voltage (a voltage developed) across another pair of said electrodes, and further comprising vibrating means operable to vibrate at least part of each electrode, wherein each contact surface is a surface of the respective said part.

It will be appreciated that features associated with one aspect of the invention may be incorporated in embodiments of any other aspect of the invention with corresponding advantage.

BRIEF DESCRIPTION OF THE DRAWINGS

Embodiments of the invention will now be described with reference to the accompanying drawings, of which.

DETAILED DESCRIPTION

Figure 1:
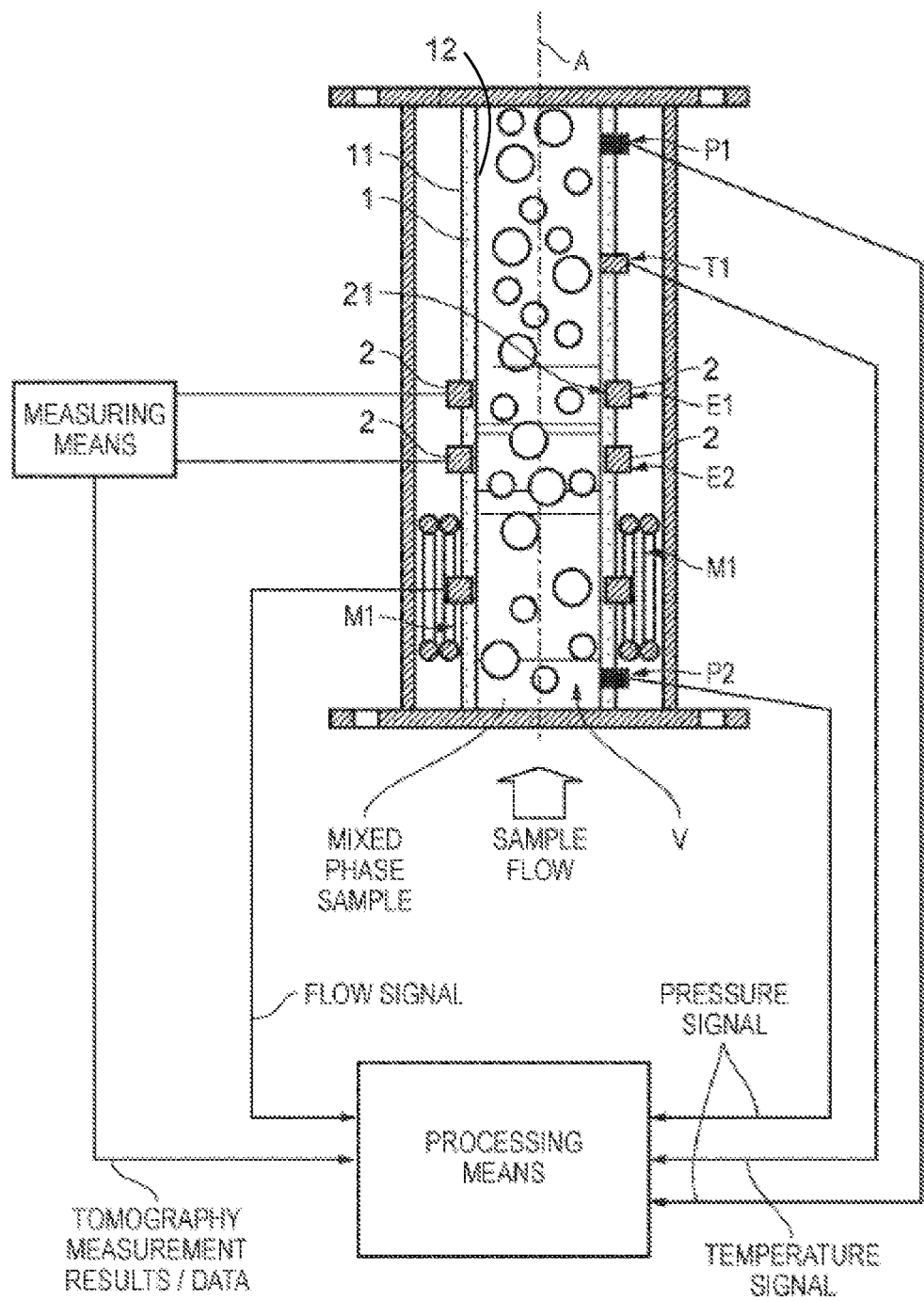
FIG. 1 is a representation of a two and/or three-phase multi-phase flow meter embodying the invention.

Referring now to FIG. 1, this illustrates a two and/or three phase multiphase flow visualisation and meter embodying the invention. The illustrated apparatus/system is a multiphase flow instrument for non-invasively measuring the phase flow rates, and rapidly imaging the flow-field distributions, of complex, unsteady two- or three-phase flows. The system may utilise a method of partial imaging with limited measurements (PILM) of Electrical Resistance Tomography (ERT) combined with an Electromagnetic flowmeter (EMF) in conjunction with auxiliary differential-pressure, temperature and conductivity measurements, providing rapid imaging speed, e.g. 10,000 dfps (dual frame per second). It can provide a measurement of volumetric flow rates in two and three phase flows, and alternatively, image time-dependent distributions of the local axial velocity and volume fraction of the dispersed and continuous phases, visualise flow patterns. Novel methods in terms of calibration and compensation are built in the instrument, providing an excellent capability to adopt various industrial environments. The instrument has been developed to address the high demands of industries for the management of productivity in many industrial sectors such as petroleum, petrochemical, food, nuclear and mineral processing.

The invention embodied by the apparatus of FIG. 1 provides new concepts and methods fused with multi-technologies from both science and engineering for two and three phase flow measurement systems, which includes (i) a dual-plane partial region tomography sensing strategy, (ii) associated partial imaging with limited measurements algorithm (PILM), (iii) a flow density metering system (FDM) based on absolute pressure sensors and an empirical model, (iv) on online conductivity sensor, (v) novel calibration methods, (vi) online compensation methods, (vii) multi-modality data fusion methods and (viii) flow data process, visualisation and users' interface methods. For the example of two-phase oil-in-water flow, the PILM methods with ERT technique is used to extract the local volume fraction distribution ($\Box_d$) and the local flow velocity distribution (vd) of the dispersed phase (oil) in water continuous flow.

FIG. 1 shows an integrated sensor system for two and three phase flow measurement. The PILM sensors (E1 and E2) consist of electrodes contacted to inner flow, which can be driven by either a voltage or current excitation tomography system. The EMF is indicated as M1. Two absolute pressure sensors (P1 & P2) are used to produce differential pressure for FDM, the temperature sensor (T1) or the online conductivity sensor (C1, given separately in Figures shown in the accompanying appendices) is also used for online compensating the changes in the water conductivity due to changes in ionic concentration or temperature. Measurements from the absolute pressure and temperature sensors also allow the standard phase volumetric flow rates to be calculated from the measured phase volumetric flow rates.

Thus, the embodiment shown in FIG. 1 comprises a conduit having a longitudinal axis arranged to be substantially vertical. The mixed-phase sample is then arranged to flow upwards through the bore of the conduit. The system includes tomography apparatus arranged to generate tomograms of the sample cross-section at two different heights along the conduit, using first and second annular arrangements of electrodes E1 and E2. Thus, the plurality of electrodes E2 are generally arranged in a lower plane, and can generate an upstream tomogram. The electrodes E1 can be used to generate a second tomogram, downstream of the first tomogram (as sample flow in this example is vertically upwards). Suitable processing of the two tomograms can therefore provide indications of volumetric fractions of the second and third phases, and the flow velocities of those phases.

Figure 2:
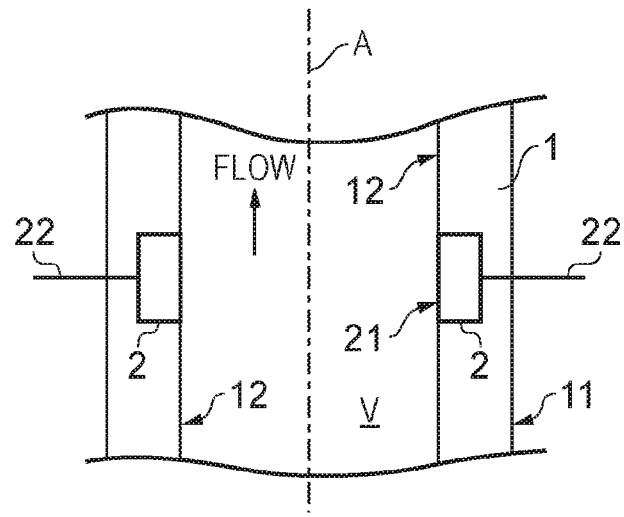
FIG. 2 is a schematic axial cross-section of part of tomography apparatus embodying the invention.
Figure 3:
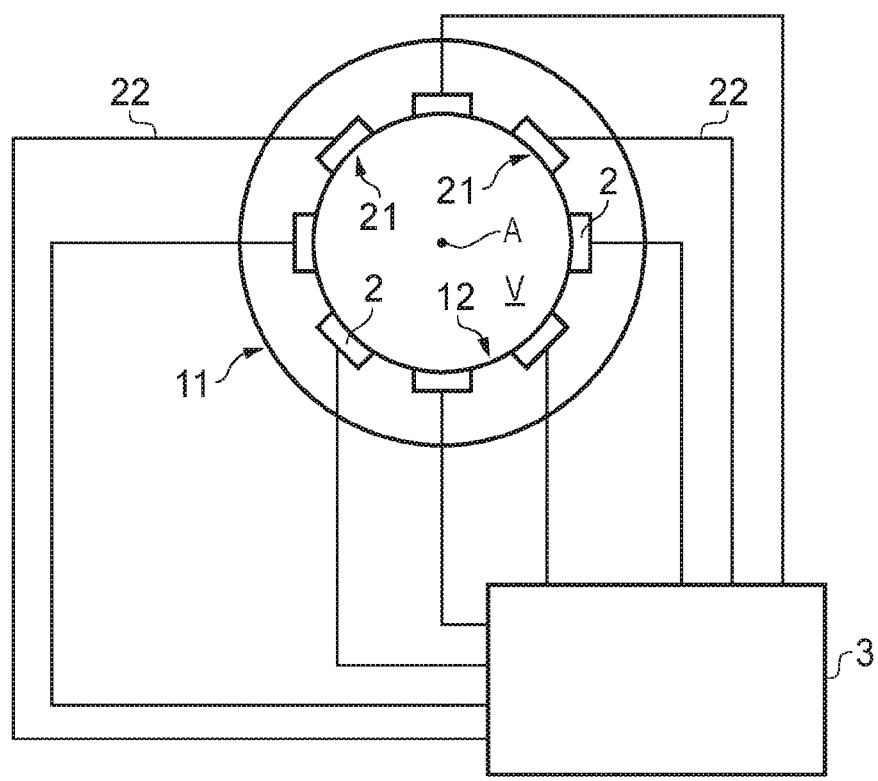
FIG. 3 is a schematic representation, including a radial cross-section of the sample-containing conduit, of tomography apparatus embodying the invention.

Referring now to FIG. 2 this is a schematic vertical cross-section of part of tomography apparatus embodying the invention. In this embodiment the apparatus comprises a conduit in the form of a cylindrical tube 1 having a longitudinal axis A along which a sample may be arranged to flow. The tube wall has an outer surface 11 and an inner surface 12 that is in contact with the flowing sample. The apparatus includes an array of measurement electrodes 2, each of which is embedded in the tube wall and has a respective contact surface 21 arranged to be flush with the inner surface 12 of the tube so that each electrode makes electrical contact with the flowing sample but does not in any way affect or impede sample flow. Thus, the electrode arrangement, which may be used in embodiments of the invention, enables measurements to be made on the flowing sample but does not impede or disturb sample flow, and does not introduce any turbulence or constrict flow. Referring also to FIG. 3, this shows further details of the tomography apparatus incorporating the electrode array shown in FIG. 2. Here, a radial cross-section of the tube is shown, illustrating the arrangement of eight electrodes set into the tube wall, with each electrode contact surface 21 forming part of the inner cylindrical surface of the sample-containing conduit. The apparatus also includes measuring means 3 connected to each of the electrodes, for performing the various measurements necessary to be processed in the generation of a tomogram. Thus, with each electrode embedded in the tube wall, an electrical connection 22 from the electrode extends radially outwards, through the tube wall, for connection to the measuring means 3.

Although these electrode arrangements and tomography apparatus can be employed in embodiments of the invention, an associated problem is that the electrode contact surfaces can accumulate material from the test sample. In other words, the contact surfaces may accumulate dirt or other deposits. As deposits form on the contact surfaces, those deposits will, of course, alter or degrade the electrical contact between the electrode and the sample material. In general, the accumulated deposits will increase the impedance of the electrode-sample connection/contact. This degradation can result in a reduction in accuracy or resolution of tomograms calculated from measurement results. A factor contributing to the deposition of material on the contact surfaces is that, at the inner walls of the conduit, sample axial flow velocity is very low (tending to zero at the actual interface). Thus, although the sample is generally flowing through the conduit, there may be negligible scrubbing action on the electrode contact surfaces.

Referring now to FIGS. 4-8, these figures show various electrode arrangements which may be utilised in embodiments of the invention and which overcome, at least partly, the problems associated with electrode arrangements in FIGS. 2 and 3.

Figure 4:
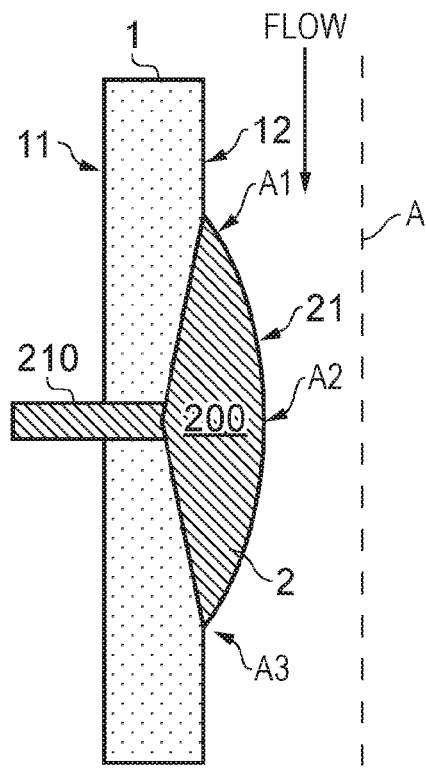
FIG. 4-FIG. 8 demonstrate various electrode structures and associated apparatus which may be employed in embodiments of the invention.

Referring now to FIG. 4, this shows part of tomography apparatus embodying the invention and incorporates an electrode 2 attached to the wall of a sample-containing conduit. Only one side of the wall is shown in the figure, with the sample arranged to flow axially along the conduit in a direction indicated by the large arrow. The conduit has an inner wall surface 12 and an outer wall surface 11. The electrode 2 comprises a first part of body of material 200 which is electrically conducted and is fixed to the conduit wall 1 such that a contact surface 21 of the electrode will be in electrical contact with the sample flowing inside the conduit. A second part or portion 210 of the electrode extends radially outwards from the first part or portion 200, to a position radially outside the conduit. The part 210 thus provides an electrical connection through the conduit wall to the inner part 200. As can be seen in the figure, an upstream portion of the contact surface 21 is shaped so that it slopes, curves, or otherwise extends radially inwards from the inner surface 12 as one progresses along the longitudinal axis in the direction of sample flow. In this example, this portion of the contact surface begins, at axial position A1, flush with the inner wall surface 12, and then extends progressively radially inwards as one progresses along the longitudinal axis up to a second axial position A2, where a tangent to the contact surface is parallel to the longitudinal axis A. From that axial position A2, the contact surface 21 then curves outwards, until at a third axial position A3 it is once again flush with the inner wall surface 12. Thus, in the arrangement shown in FIG. 4, at least a portion of the electrode contact surface is sloped, extends, ramps, or is curved generally radially inwards. A downstream portion of the contact surface 21 then curves radially outwards, back to the conduit inner wall 12. Advantageously, as the sample material flows by the electrode surface 21, it is imparted with a radial velocity component as a result of interaction with the inwardly sloping or inwardly curved portion of the surface 21, and in turn exerts a force on the electrode and a scrubbing or cleaning action which at least partly inhibits or prevents accumulation of deposits on the inwardly sloped electrode surface. This self-cleaning action or scrubbing action is of course a function of the slope or curvature of the surface 21. The more aggressive the slope or curvature, the greater the self-cleaning or scrubbing action, but this does also increasingly affect flow dynamics in the tube. In general, a compromise should be made between obtaining sufficient self-cleaning action and having a minimal effect on flow conditions.

Figure 5:
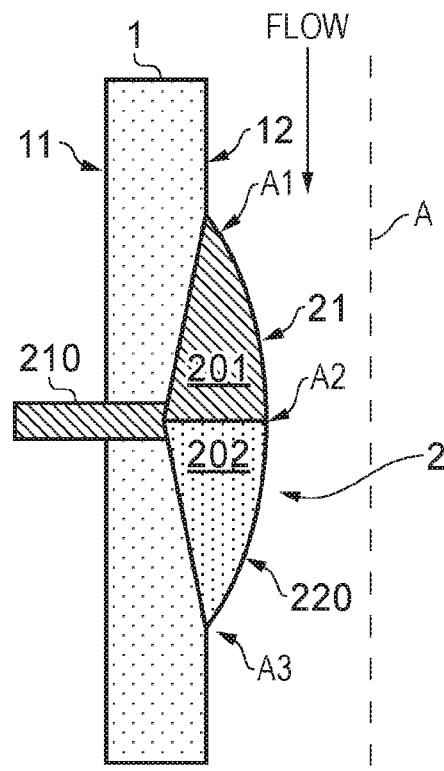

Referring now to FIG. 5, this shows an alternative electrode arrangement which may be used in embodiments. Here, a first, upstream portion 201 of the electrode 2 is formed from conductive material and has a contact surface 21 arranged to curve radially inwards from the conduit inner wall 12 along the axis A. A downstream portion 202 of the electrode has a surface 220 which is shaped to form a continuation of contact surface 21. However, this second portion 202 is formed from non-conductive material. Overall, therefore, the electrode is arranged to introduce minimal turbulence into the flowing sample, and the contact surface 21 is at least partly cleaned by the flowing sample because it is curved radially inwards. It will be appreciated that the surface 220 of the downstream portion 202 may have sample material deposited on it, but that will not affect the electrical contact between the electrode and the flowing sample as the downstream portion 202 is electrically non-conductive.

In certain alternative embodiments, the electrode structure may be generally the same as that shown in FIG. 4, but the downstream part of the electrode surface may be provided with a non-conducting coating. This can then provide the same advantages as the arrangement shown in FIG. 5, where any deposits formed on the downstream portion will not affect the electrical contact between electrode and sample.

Figure 6:
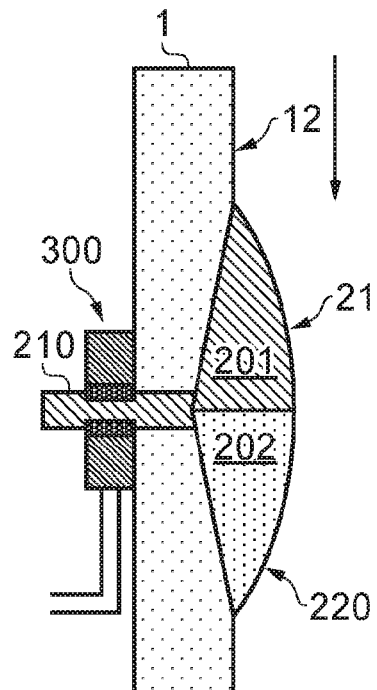

Moving on to FIG. 6, this shows yet another electrode arrangement in certain embodiments of the invention. Here, the general electrode arrangement is as shown in FIG. 5, but the apparatus includes heating means in the form of a heater 300 arranged to heat the electrode part 210, which is electrically and thermally conductive, and so conducts heat through to the electrically conductive first part 210. A variety of techniques may be used to provide heating, for example the electrode part 210 can be heated with heated steam, oil, or electricity, or using inductive techniques, and that heat is conducted through to the electrode part 201 and hence heats the contact surface 21. This heating can be used to prevent the accumulation of deposits such as wax or other thick fluids on the contact surface 21.

Figure 7:
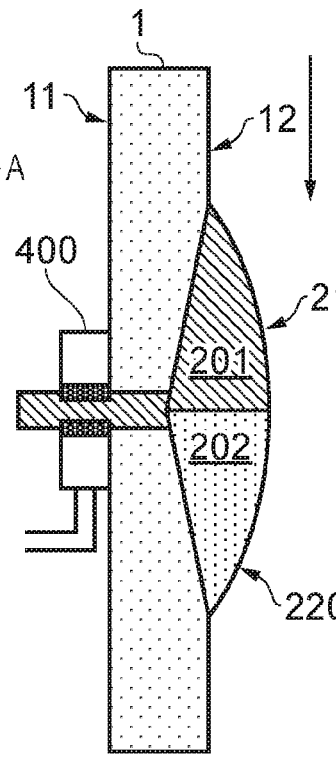

Referring now to FIG. 7, this shows another electrode arrangement in embodiments of the invention, this time incorporating vibrating means, for example in the form of an ultrasonic transducer 400, arranged to vibrate the electrode contact surface 21. In the arrangement of FIG. 7, this is achieved by arranging the vibrating means to vibrate the rigid third portion 210 of the electrode, which then transmits this vibration through the vessel wall 1 to the first and second electrode parts 201, 202. This arrangement can be used to remove or prevent the accumulation of rigid or hard deposits on the contact surface 21, and optionally also on the non-contact surface 220.

Figure 8:
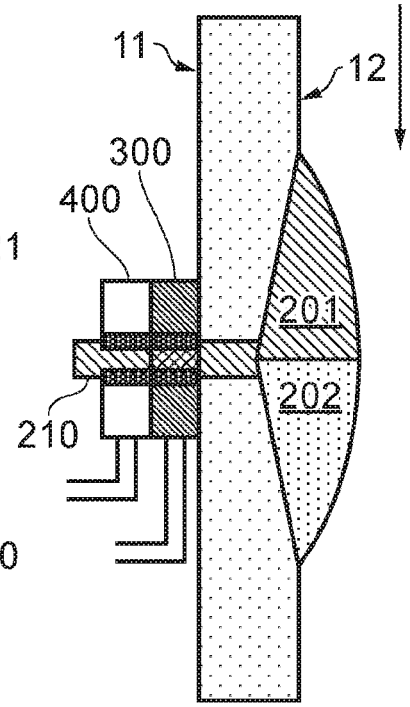

FIG. 8 shows yet another electrode arrangement which may be used in embodiments of the invention, incorporating both heating means 300 and vibrating means 400 which may be used separately, or in combination, to provide heating and/or vibration of at least the contact surface 21.

It will be appreciated that each of FIGS. 5 to 8 illustrates an electrode 2 comprising a respective downstream portion having a respective electrically non-conducting surface 220.

In certain embodiments each said electrically non-conducting surface is arranged to continue axially from a respective contact surface, and slope outwards, away from the longitudinal axis, along the longitudinal axis.

In certain embodiments each said electrically non-conducting surface is arranged to abut a respective contact surface at the second axial position and slope outwards along the longitudinal axis to the third axial position.

In certain embodiments each electrically non-conducting surface is arranged to be flush with an interior surface of the conduit defining a wall of the interior volume at said third axial position.

Description Sub-Section 1

This sub-section describes the Measurement of Vertical Oil-in-water Two-phase Flow Using a Dual-modality ERT/EMF System embodying the invention.

Summary of Sub-Section 1

Oil-in-water two-phase flows are often encountered in upstream petroleum industry. The measurement of phase flow rates is of particular importance for managing oil production and water disposal and/or water reinjection in the oil industry. The complexity of oil-in-water flow structures creates a challenge to flow measurement. This sub-section proposes a new method of two-phase flow metering, which is based on the use of dual-modality system and multidimensional data fusion. The Electrical Resistance Tomography system (ERT) is used in combination with a commercial off-the-shelf Electromagnetic Flow Meter (EMF) to measure the volumetric flow rate of each constituent phase. The water flow rate is determined from the EMF with an input of the mean oil-fraction measured by the ERT. The dispersed oil-phase flow rate is determined from the mean oil-fraction and the mean oil velocity measured by the ERT cross-correlation velocity profiling. Experiments were carried out on a vertical upward oil-in-water pipe flow, 50 mm inner-diameter test section, at different total liquid flow rates covering the range of 8-16 m3/hr. The oil and water flow rate measurements obtained from the ERT and the EMF are compared to their respective references. The accuracy of these measurements is discussed and the capability of the measurement system is assessed. This work provides a baseline check for a three-phase gas-liquid flow measurement research prototype based on an extended ERT-EMF dual-modality system (reported in a separate sub-section).

Introduction to Sub-Section 1

Oil-in-water two-phase flows are often encountered in the upstream petroleum industry. The measurement of phase flow rates is of particular importance for managing oil production and water disposal and/or water reinjection in the oil industry. The need for a measurement system, by which each constituent phase flow quantity is determined, has always been present since oil industry started. For example, in order to know what is happening in the reservoir, accurate information regarding the producing wells is required. Therefore, a reliable measurement system or method is required to satisfy these needs. In return it enables optimisation of the oil production and ensures long term recovery from the reservoir. However, in the later stage of oil production the complexity of oil-in-water high water-cut flows (a small subset of oil-water-gas three-phase flows), which is caused by differences in densities and viscosities of each phase, can create a challenge to flow measurement (Oddie 2004; Thorn 1997; Thorn 2013).

Over the years a considerable number of methods have been evaluated, in the aim of accurately measuring oil-water flows in horizontal, inclined or vertical pipes. Some of these methods include the use of flow-constriction differential-pressure (DP) sensors (Pal 1993; Skea and Hall 1999; Zhang 2013), Coriolis, vortex shedding or turbine 'single-phase' flow meters (Skea and Hall 1999), electrical conductance sensor combined with a DP sensor (Tang 2013). There are still some drawbacks in the investigated methods, such as the flow-distribution dependency (separated vs. well-mixed flow), use of flow-restriction (in the DP measurement) and of the moving parts. It is desirable to have a full-bore oil-water flow metering method that has the potential to be extended to the measurement of oil-water-gas three-phase flows, without the use of a radioactive source.

Since the 1980s tomography techniques have gone through a major development and are used to provide a novel means of non-intrusive flow measurement and rapid visualisation of the internal structure of process industry (Wang 1999). The Electrical Resistance Tomography (ERT), amongst the family of tomography techniques, can be used as a viable tool to non-intrusively and safely interrogate the internal structure of oil-water (-gas) flow. It is worth pointing out that in two-phase flow metering it is almost impossible to determine all flow parameters of both phases (such as velocities) using only one conventional method or flow meter. Thus, a secondary sensor or method is required to determine each phase flow parameter.

Therefore, the objective of this research work is to develop an on-line two-phase oil-in-water flow dual-modality measurement system, in which the ERT is used as the main subsystem and an off-the-shelf Electromagnetic Flow Meter (EMF) as a secondary subsystem (sensor). The novel dual-modality system is developed for on-line rapid phase volumetric flow rate measurement. The dispersed oil-phase flow rate is determined from the mean oil volume fraction and the mean oil velocity measured by the ERT and cross-correlation velocity profiling. The water flow rate is determined from the EMF with an input of the mean oil volume fraction measured by the ERT.

Measurement Concepts

The principle of the method ERT-EMF dual-modality system and multi-dimensional data fusion for phase flow-rate determination is described in this section.

Phase Fraction Determination

Figure 9:
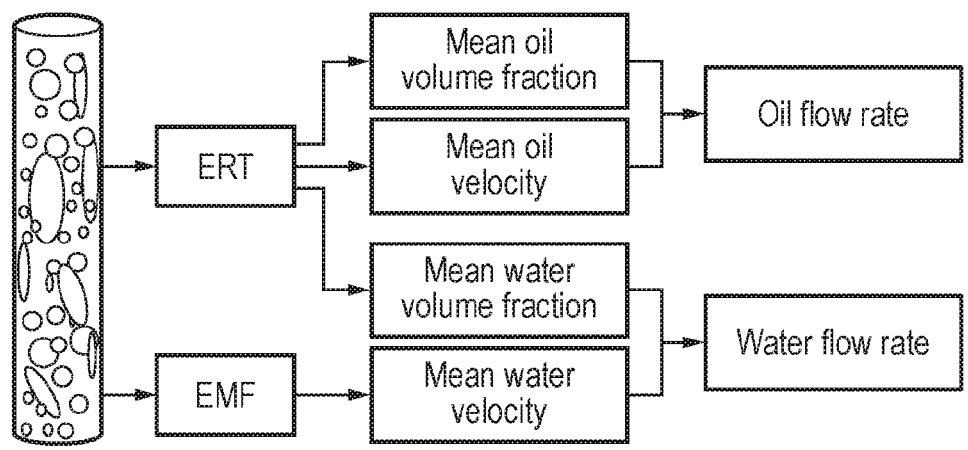
FIG. 9 illustrates the ERT-EMF phase flow rate determination concept for two-phase oil-in-water flow in an embodiment of the invention.

In two-phase oil-in-water flow, the ERT technique is used to extract the local volume fraction distribution ($\alpha_o$) and the local flow velocity distribution ($V_o$) of the dispersed oil phase across the pipe cross-section. The ERT measurement is based on the relative change between the conductivity of the two-phase mixture and the conductivity of conductive water phase (water conductivity can be monitored online separately, Jia et al. 2014). The EMF is used to measure the mean velocity of the continuous water phase ($V_w$), while the mean volume fraction of the continuous phase ($\alpha_w$) is determined from the ERT. The schematic diagram of phase determination concept for two-phase oil-in-water flow is illustrated in FIG. 9. We have $$\bar{\alpha}_O = \bar{\alpha}_{ERT} \quad (1)$$

$$\bar{\alpha}_O + \bar{\alpha}_W = 1 \quad (2)$$

The mean water local volume fraction can be obtained by substituting equation (1) in (2).

$$\bar{\alpha}_w = 1 - \bar{\alpha}_{ERT} \quad (3)$$

Phase Volumetric Flow Rate Determination

The phase volume flow rate can be determined through combination of the dual-plane ERT and the EMF measurements. The oil flow rate can be obtained from the local mean oil volume fraction distribution and mean axial oil velocity distribution, which are both obtained from the ERT, across the pipe cross-sectional area (A), as shown in Eq. 4. The oil velocity is determined from the cross-correlation of dual-plane oil fraction distributions. The water flow rate is obtained from the product of mean water volume fraction, obtained from the ERT, and mean axial water velocity measured by the EMF, across the pipe cross-sectional area (A), as shown in Eq. 5. The subscripts, ERT and EMF, in both equations denote the method or (or technique) used to measure the relevant parameter.

$$Q_o = \bar{\alpha}_{o(ERT)} \bar{v}_{o(ERT)} A \quad (4)$$

$$Q_w = \bar{\alpha}_{w(ERT)} \bar{v}_{w(EMF)} A \quad (5)$$

Experimental Set-Up and Data Processing

The Experimental Flow Facility

Figure 10:
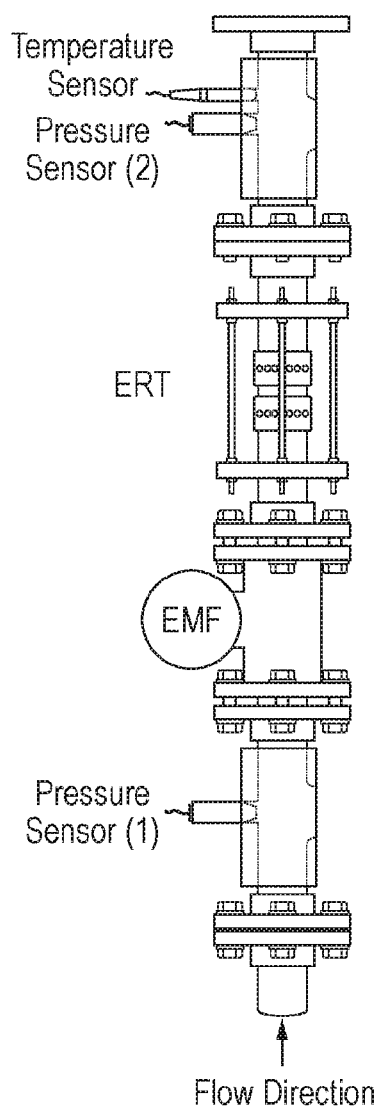
FIG. 10 is a schematic diagram of the test section in an embodiment.

Experiments were carried out using the inclinable three-phase flow facility in Schlumberger Gould Research (SGR). The two-phase oil-in-water measurement system was installed on the flow loop and tested mainly for vertical upward flows. The measurement system was located at approximately 6 m from the inlet of the SGR flow loop, with a transparent pipe section of 500 mm in length installed at the upstream for the purpose of visual observation during the experiments. The test section is approximately 1 m long with 50 mm internal diameter pipeline and composed of a dual-plane ERT sensor (designed and manufactured by the University of Leeds), an off-the-shelf EMF (OPTIFLUX 4000, from KROHNE), two absolute pressure transducers (PXM209-2.50A10V, from OMEGA) and one temperature sensor (SPRTX-M1, from OMEGA). FIG. 10 illustrates the schematic diagram of the test section.

Water and oil were pumped from the flow-loop separator, measured respectively by electromagnetic and turbine single-phase liquid reference flow meters, and introduced into the flow loop as a two-phase mixture. The oil fluid was low-viscosity (2.1 cP) Total-75 Kerosene and local tap water ($\approx$0.7 mS/cm at 20° C.). The range of oil flow rate and water flow rate used in the experiments were 1-8 m$^3$/hr and 4-11 m$^3$/hr respectively. The total liquid flow rate was 8-16 m$^3$/hr, with a maximum line pressure 2.2 bar. Two groups of experiments were carried out, each with different mixture velocity and different water-in-liquid ratio (WLR). It is worth mentioning that all the experiments were carried out within water continuous region (WLR>30%).

The Dual-Modality ERT/EMF Flow Measurement System

The oil-in-water measurement system is composed of a dual-plane ERT sensor and an off-the-shelf Electromagnetic Flow meter. The EMF is an OPTIFLUX 4000 with Hastelloy C22 fixed electrodes with 2 electrodes construction. The accuracy of the EMF is ±0.2%. The EMF is installed at the upstream of and next to the dual-plane ERT sensor.

The ERT based hardware system is a novel on-line measurement system, which has been developed by the University of Leeds. The dual-plane ERT sensor was in-house built with each sensor plane consists of 16 equally spaced stainless-steel electrodes, which are flush mounted at the periphery of each sensor plane. The sensor planes are separated by an axial distance of 50 mm to realise the application of cross-correlation dispersed-phase velocity profiling method. The hardware system enables the use of either 8 electrodes or 16 electrodes per plane, depending on the purpose and the application. In the experiments highlighted in this section, only 8-electrode arrangement was used for the image reconstruction of the mixture conductivity distribution (for dispersed oil-phase fraction determination).

A total of 20000 dual frames were acquired for each flow condition (about 20-second duration). The algorithm used for the image reconstruction is the Modified Sensitivity Back Projection (MSBP). The ERT is used to determine the oil volume fraction distribution using Maxwell relationship (Maxwell 1881), considering the oil conductivity being zero and water as a continuous conducting phase. The axial oil velocity distribution is calculated through the combination of the ERT and pixel-to-pixel Cross-Correlation. The phase flow rates are determined through the combination of the ERT and EMF measurements.

Results and Discussions

The flow quantities obtained from the experimental measurements are presented in the final form of water and oil volumetric flow rates ($Q_w$ & $Q_o$) in this sub-section, as shown in Table 1.

TABLE 1

Reference and measured Phase volumetric flow rate

|  | Reference | | Measured | |
|---|---|---|---|---|
|  | $Q_w$ (m$^3$/hr) | $Q_o$ (m$^3$/hr) | $Q_w$ (m$^3$/hr) | $Q_o$ (m$^3$/hr) |
| Variable WLR = $Q_w/Q_T$ | 8 | 4 | 7.98 | 4.52 |
|  | 9 | 3 | 8.98 | 3.20 |
|  | 10 | 2 | 9.95 | 2.13 |
|  | 11 | 1 | 10.91 | 1.05 |
| Variable liquid velocity (WLR = 50%) | 4 | 4 | 4.15 | 4.21 |
|  | 5 | 5 | 5.13 | 5.40 |
|  | 6 | 6 | 6.06 | 6.92 |
|  | 7 | 7 | 7.18 | 7.87 |
|  | 8 | 8 | 8.05 | 9.14 |

The experiment conditions were split into two separate test groups. In the first test group the WLR is variable and liquid velocity (total liquid rate) is constant ($Q_T$=12 m$^3$/hr), while in the second test group the liquid velocity is variable and WLR is constant (at 50%). The main reason for splitting the test conditions into two separate groups was to evaluate the effect of WLR and liquid velocity on the measurement scheme. Each test group is individually analysed by comparing the measured phase volume flow rate with the reference phase volume flow rate. Since the constituent phases are incompressible fluids, then it is reasonable to use the inlet condition of each phase as a reference to validate the ERT based measurement system. The uncertainty associated with the measured phase flow rates is discussed (Table 2 below).

Effect of WLR on the Measurement Scheme

The effect of WLR was determined by comparing measured phase volume flow rate, obtained from the ERT based two-phase flow measurement system, with that of reference as a function of water cut (or WLR). The WLR is calculated as the ratio of water flow rate to total liquid flow rate (i.e. oil and water).

Figure 11:
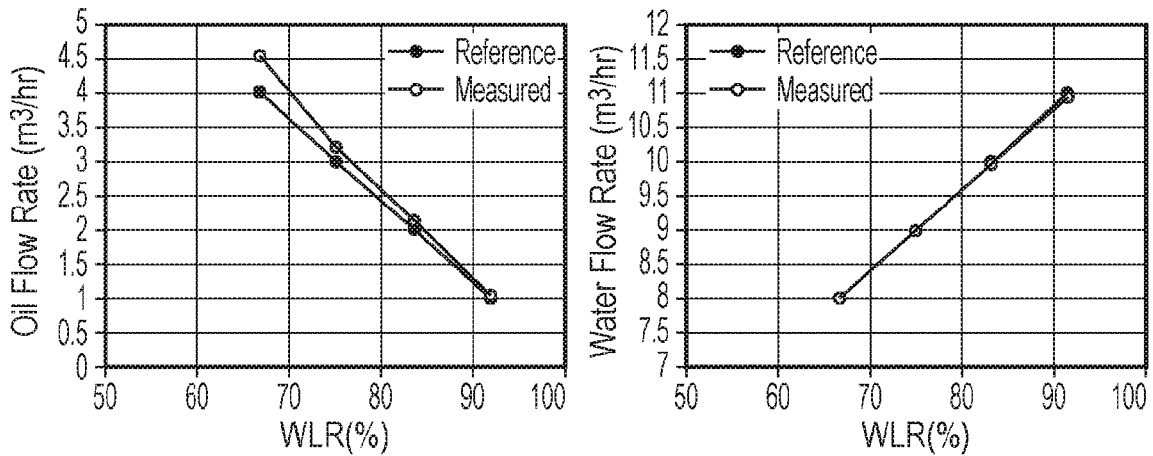
FIG. 11 shows the effect of WLR (QT=12 m3/h); (left) oil flow rate, (right) water flow rate in an embodiment.

FIG. 11 shows the comparison of measured phase flow rates with that of reference for the variable WLR test group. It can be seen that the measured water flow rate agrees well with that of the reference (FIG. 11 right plot). On the other hand, by observing FIG. 11 (left plot), it is quite clear that the oil flow rates are overestimated with decreasing WLR, probably due to the overestimate in the mean oil velocity as the oil volume fraction increases.

Effect of Liquid Velocity on the Measurement Scheme

Figure 12:
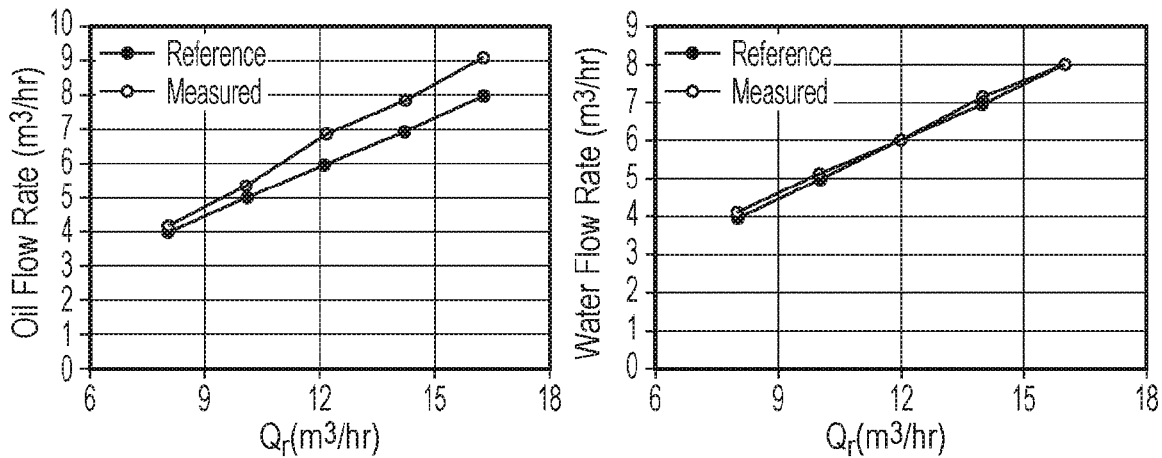
FIG. 12 shows the effect of liquid rate (velocity) with WLR=50%; (left) oil flow rate, (right) water flow rate in an embodiment.

The effect of varying liquid velocity on the measurement scheme is highlighted by comparing the measured phase volume flow rate with that of the reference as a function of total liquid flow rate. The comparison results are illustrated in FIG. 12 for each phase. It can be seen that the measured water flow rate again agrees well with that of the reference (FIG. 12 right plot). On the other hand, the measured oil flow rate shows an increasing overestimation of the reference with increasing total liquid rate or velocity (FIG. 12 left plot). This may be attributed to the increasing error in mean oil-velocity (determined from the dual-plane cross-correlation transit-time τ) when liquid flow velocity $V_L$ increases (the relative error $\delta V_L/V_L = -\delta\tau/\tau = -(V_L/L)\delta\tau$; with transit-time resolution $\delta\tau = 1$ ms, $V_L = 1.2$ to 2.4 m/s, dual-plane spacing L=50 mm, $\delta V/V = -2.4\%$ to $-4.8\%$).

Evaluation of the Measurement Schemes

In order to evaluate the measurement schemes, a quantitative and qualitative error analysis was carried out for all the measured phase volume flow rates. Table 2 highlights the relative error in the measured phase volumetric flow rates with respect to the reference values. By observing Table 2, it can be seen that the relative errors in measured oil flow rate are above +5% and up to about 15%; that is the oil flow rate is overall overestimated. The water flow rate is measured within ±4% of reading, indicating that combining the EMF-measured mean water velocity with ERT-measured mean water-fraction (from the mean oil-fraction) is sound.

TABLE 2

Relative error in the measured water and oil phase flow rates

|  | Reference | | Measured | | Relative | |
| --- | --- | --- | --- | --- | --- | --- |
|  | $Q_w$ | $Q_o$ | $Q_w$ | $Q_o$ | Error (%) | |
|  | (m³/hr) | (m³/hr) | (m³/hr) | (m³/hr) | $Q_w$ | $Q_o$ |
| Variable WLR | 8 | 4 | 7.98 | 4.52 | −0.26 | 12.99 |
| ($Q_T$ = 12 m³/h) | 9 | 3 | 8.98 | 3.20 | −0.25 | 6.56 |
|  | 10 | 2 | 9.95 | 2.13 | −0.55 | 6.39 |
|  | 11 | 1 | 10.91 | 1.05 | −0.84 | 5.15 |
| Variable liquid | 4 | 4 | 4.15 | 4.21 | 3.71 | 5.31 |
| velocity | 5 | 5 | 5.13 | 5.40 | 2.61 | 7.92 |
| (WLR = 50%) | 6 | 6 | 6.06 | 6.92 | 1.07 | 15.26 |
|  | 7 | 7 | 7.18 | 7.87 | 2.57 | 12.38 |
|  | 8 | 8 | 8.05 | 9.14 | 0.59 | 14.22 |

Figure 13:
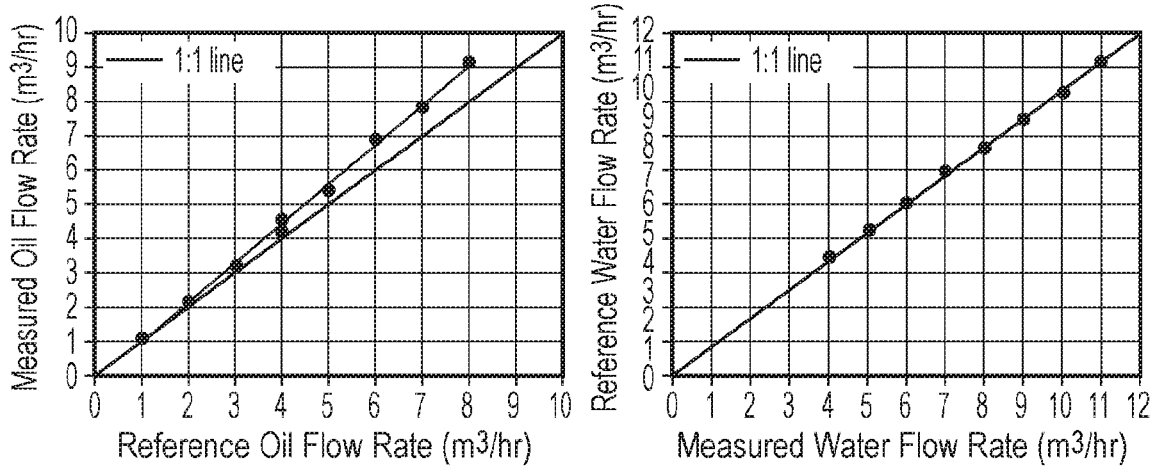
FIG. 13 shows, for both test groups, comparison of measured phase flow rate with that of reference; (left) oil flow rate, (right) water flow rate in an embodiment.

FIG. 13 shows the comparison of measured oil and water phase volumetric flow rates for both test groups (variable WLR and variable liquid velocity) with the respective references.

Figure 14:
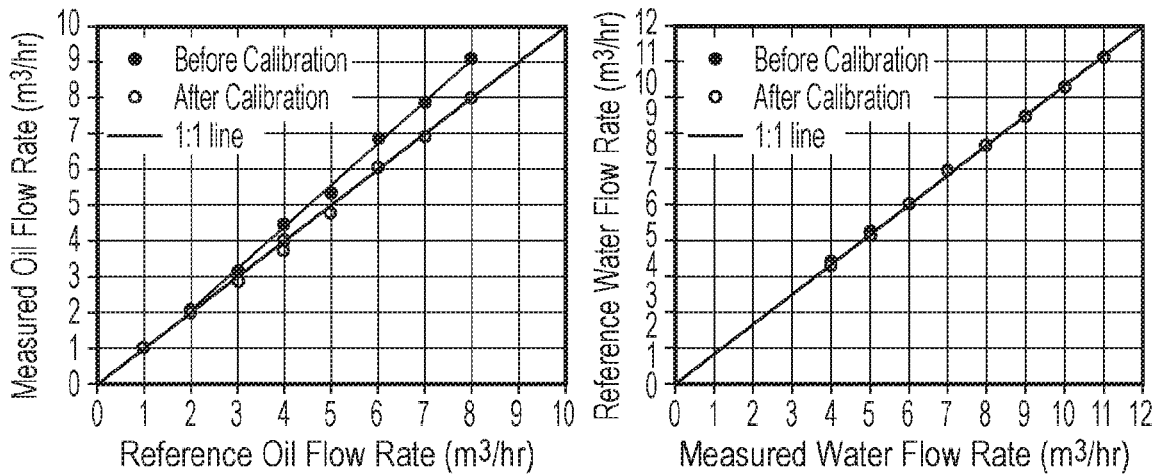
FIG. 14 is a comparison of measured phase flow rate, before and after calibration, with that of reference; (left) oil flow rate, (right) water flow rate in an embodiment.

It is possible to correct the measured oil and water flow rates obtained from the oil-water two-phase measurement system, by using calibration functions determined from the SGR respectively references. FIG. 14 illustrates the comparison of originally measured phase flow rate and calibrated phase flow rate with that of the reference. It can clearly be seen that after calibration the deviation from the reference is dramatically reduced, particularly for measured oil flow rates.

Figure 15:
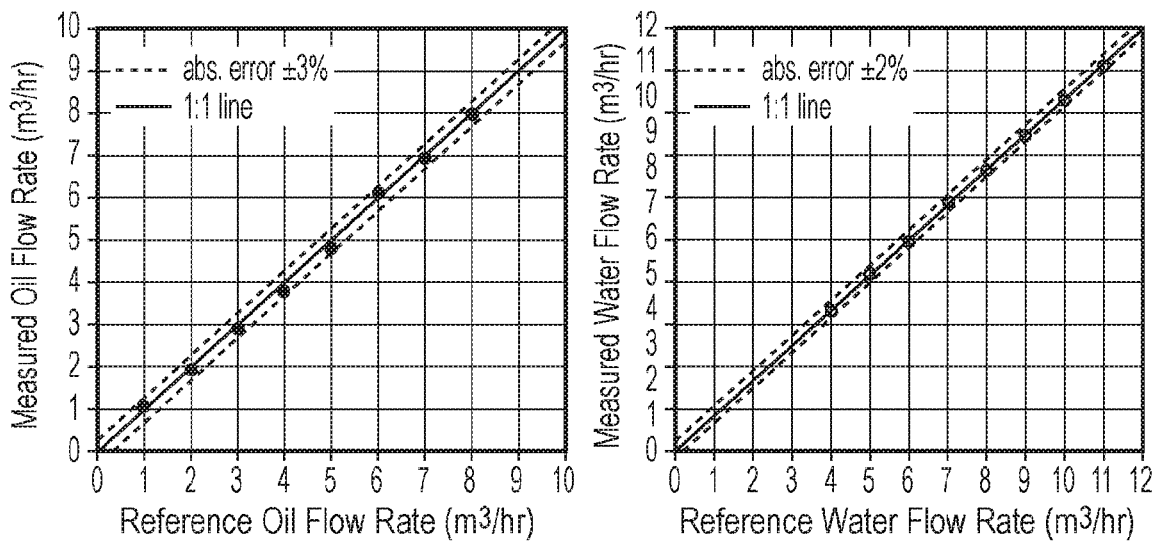
FIG. 15 shows the measurement absolute error band for; (left) oil flow rate, (right) water flow rate in an embodiment.

The absolute-error band associated with the measured phase flow rates after calibration is presented in FIG. 15. It illustrates the measurement errors for both test groups and the range of conditions used in experiments. The error in measuring oil flow rates is about ±3% absolute, while that in measuring water flow rate is about ±2% absolute. It is worth mentioning that the above absolute-error band values are based on the final corrected flow rates of oil and water phases.

CONCLUSIONS

This sub-section demonstrated the performance of a novel ERT-EMF dual-modality measurement system for the measurement of phase volumetric flow rate of oil-in-water flows. Based on the comparison between the measured oil and water phase flow rates and those of the respective references, a good agreement was noted for the flow rate of the continuous water phase (determined from the EMF-measured mean water velocity and the ERT-measured mean water fraction). Nevertheless, a large deviation in the measured dispersed-phase oil flow rate was observed, particularly at lower WLR and higher liquid velocities. The main-contributing error is believed to be attributed from the mean (dispersed-phase) oil-velocity determined from dual-plane cross-correlation transit-time. After error-correction based on the flow-loop reference (calibration) data, the measured oil flow rates could potentially be corrected to ±3% absolute error, while the measured water flow rates corrected to ±2% absolute error. The novel dual-modality flow measurement system can be extended to measuring three-phase gas-liquid (gas, oil and water) flows (Wang et al. 2014).

REFERENCES FOR SUB-SECTION 1

JIA, J., WANG, M., FARAJ, Y. AND WANG, Q. (2014), Significance of On-line Conductivity Calibration for EIT, 5th International Workshop on Process Tomography, Jeju, South Korea, 2014.
MAXWELL, J. C., (1881), A treatise on Electricity and Magnetism, Clarendon Press, Oxford.
ODDIE, G. AND PEARSON, J. R. A., (2004), Horizontal Flow-rate measurement in two-phase flow. Annual Review of Fluid Mechanics, 36, pp. 149-72.
PAL, R., (1993), Flow of oil-in-water emulsions through orifice and venturi meters, Industrial and Chemical Engineering Research, 32, 6, pp. 1212-1217.
SKEA, A. F. AND HALL, A. W. R., (1999), Effects of water in oil and oil in water on single phase flowmeter, Flow Measurement and Instrumentation, 10, pp. 151-157.
TAN, C., WU, H. AND DONG, F., (2013), Horizontal oil-water two-phase flow measurement with information fusion conductance ring sensor and cone meter, Flow Measurement and Instrumentation, 34, pp. 83-90.
THORN, R., JOHANSEN, G. A. AND HAMMER, E. A., (1997), Recent developments in three-phase flow measurement, Measurement Science and Technology, 8, 7, pp. 691-701.
THORN, R., JOHANSEN, G. A. AND HJERTAKER, B. T., (2013), Three-phase flow measurement in petroleum industry, Measurement Science and Technology, 24, 1, pp. 012003.
WANG, M., MANN, R. AND DICKIN, F. J., (1999), Electrical Resistance Tomographic Sensing Systems for Industrial Applications, Chemical Engineering Communications, 175, pp. 49-70.
WANG, M., JIA, J., FARAJ, Y., WANG, Q., XIE, C.-G., ODDIE, G., PRIMROSE, K., AND QIU, C. (2014), A New Visualisation and Measurement Technology for Multiphase Flows, 5th International Workshop on Process Tomography, Jeju, South Korea, 2014.
ZHANG, J., XU, J., WU, Y., LI, D. LI, H., (2013), Experimental validation of the calculation of phase holdup for an oil-water two-phase vertical flow based on the measurement of pressure drops, Flow Measurement and Instrumentation, 31, pp. 96-101.

Comments on Sub-Section 1

Referring to sub-section 1 above, this contains further description and information on certain flow monitoring systems embodying the invention. Looking at FIG. 9, this embodiment comprises a conduit having a bore through which a mixed-phase sample (comprising oil mixed with water) could be arranged to flow in a vertical direction. Tomography apparatus (in this example, electrical resistance tomography apparatus) is arranged to generate tomograms of the sample flowing in the conduit, and from those tomograms processing means is arranged to calculate the mean oil volume fraction, the mean oil velocity, and the mean water volume fraction.

The system also includes an electromagnetic flow meter (EMF) which provides a signal indicative of mean water velocity. The processing means is arranged to calculate an oil flow rate from the mean oil fraction and the mean oil velocity. The processing means is further adapted to calculate water flow rate from the mean water volume fraction and the mean water velocity.

FIG. 10 shows further detail of a system embodying the invention. Here, the ERT apparatus again comprises two sets of measurement electrodes which can be used in measurements to generate data that can then be processed to generate tomograms of the sample flow at two axial positions along the conduit (i.e. in first and second planes). The electromagnetic flow meter is arranged upstream of the ERT apparatus. A first pressure sensor is arranged upstream of the EMF, and a second pressure sensor and a temperature sensor are arranged downstream of the ERT.

Description Sub-Section 2

This sub-section describes a New Visualisation and Measurement Technology for Multiphase Flows and embodying the present invention.

Summary of Sub-Section 2

This sub-section reports the performance of a research prototype of a new multiphase flow instrument to non-invasively measure the phase flow rates, with the capability to rapidly image the flow distributions of two- (solids, gas or oil in water) and three-phase (gas and oil in water) flows. The research prototype is based on the novel concepts of combining vector Electrical Impedance Tomography (EIT) sensor (for measuring dispersed-phase velocity and fraction) with an electromagnetic flow meter (EMF, for measuring continuous-phase velocity with the EIT input) and a gradiomanometer flow-mixture density meter (FDM), in addition to on-line water conductivity, temperature and absolute pressure measurements. EIT-EMF-FDM data fusion embedded in the research prototype includes auto-compensation, flow regime recognition and EIT-image correction. This enables the determination of mean concentration, mean velocity and hence the mean flow rate of each individual phases based on the measurement of dispersed-phase distributions and velocity profiles. Results from recent flow-loop experiments will be described. The performance of the research prototype in flow-rate measurements will be evaluated by comparison with the flow-loop references. Within the scope of this sub-section vertical flows with a conductive continuous liquid phase will be addressed.

Introduction to Sub-Section 2

The advent of surface multiphase flowmeter (MPFM) is fundamentally changing the production monitoring of complex flows from oil-gas production wells. This transformation is driven by new technology that can measure rapid variations in oil-water-gas multiphase flows better than conventional separators. The capability to measure multiphase flow rate in real time increases operational efficiency, saving both time and cost. Accurately quantifying individual fluid phases in a production stream allows operators to make more informed decisions about well performance, to better identify, understand and remediate problematic wells, optimise artificial lift operations and build dynamic reservoir models (Xie et al. 2007).

Commonly used methods for measuring multiphase flows are based on γ-ray attenuation, RF/microwave and/or electrical impedance techniques in combination with a differential-pressure device such as a Venturi flowmeter (Xie et al. 2007, Thorn et al. 2012). Phase fraction measurement based on γ-ray attenuation methods is elegant; to achieve desired statistical accuracy there are however practical or logistical difficulties to overcome when an intense radiation source is used to achieve both the temporal and spatial resolution at the expense of increasing safety precautions (Van Santen et al. 1995). An MPFM based on nuclear magnetic resonance (NMR) technique is currently under development (Appel et al. 2011), but an NMR system tends to be complex and expensive and has limitation in temporal resolution and hence in velocity measurement-range. A relatively low-cost, radioactive-source free MPFM is desirable for industrial applications and is the focus of this work.

Electrical Impedance Tomography (EIT) has been developed to image and measure industrial processes with material conductivity contrast and with the continuous phase being electrically conductive (Sharifi and Young, 2013). Since EIT can detect local changes in electrical conductivity, the technique is used to study the unsteady mixing (George et al. 2000) or flow dynamics of liquid mixtures such as gas-liquid and solid-liquid mixtures (Wang et al. 2005). EIT may, therefore, be suitable for numerous aqueous-based processes (York 2001). Using sequences of images obtained from a dual-plane EIT flow sensor, the local flow velocity of the dispersed phase(s) can be deduced based on pixel-pixel cross-correlation methods (Lucas et al. 1999, Deng et al. 2001, Mosorov et al. 2002). This demands an EIT system to have a rapid response time (Wang et al. 2005) in order to measure multiphase flows with phase distributions changing in space and time. An EIT system can be made low costs in both installation and maintenance. However, due to the nonlinear nature of the low frequency electric field distribution and the limited number of measurements (a trade-off with high measurement speed), an EIT system presents a low spatial resolution and non-uniform sensitivity distribution over the domain to be imaged. Since spatial- and time-averaged phase flow rates are the dominant parameters in multiphase flow measurement, an EIT is considered to be a good candidate for the fraction and/or velocity measurement of dispersed phases, e.g. gas- and/or oil-in-water.

Concepts and Methods

The principle of the proposed three-phase measurement system is based on the use of multi-modality sensors and multi-dimensional data fusion, where three independent flow measurement sub-systems and three online calibration/compensation sub-systems are applied. These are, namely an Electrical Impedance Tomography (EIT) sensor (for measuring dispersed-phase velocity and fraction), an electromagnetic flow meter (EMF, for measuring continuous-phase velocity with an input of the EIT mean volume fraction) and a gradiomanometer flow-mixture density meter (FDM), in addition to on-line water conductivity, temperature and absolute pressure measurements. EIT-EMF-FDM data fusion embedded in the research prototype includes auto-compensation, flow regime recognition and EIT-image correction.

Measurement Principle

In this work, for a vertical gas-oil-water three-phase (water-continuous) flow, an EIT technique with dual-plane sensors is used to extract local volume fraction distribution, local flow velocity and flow rate of the dispersed phases (e.g. gas and oil). The principle of EMF is applied to measure the mean flow velocity and flow rate of water-continuous liquid phase, with the online correction of the mean volume fraction of the non-conducting gas and oil phases obtained using the EIT. The gas-oil-water flow-mixture density is measured by using FDM (with the gas-phase correction factor provided by an empirical model and the online absolute pressure measurement). Therefore, the volume fraction of individual phases can be derived as, $$\bar{\alpha}_O = \frac{(\rho_W - \rho_G)\bar{\alpha}_{ERT} - (\rho_W - \rho_{FDM})}{\rho_O - \rho_G} \quad (1)$$

$$\bar{\alpha}_G = \bar{\alpha}_{ERT} - \bar{\alpha}_O \quad (2)$$

$$\bar{\alpha}_W = 1 - \bar{\alpha}_{ERT} \quad (3)$$

For vertical water-continuous flows with negligible oil-water velocity slip, the flow rates of individual phases can be determined as, $$Q_G = A\bar{\alpha}_G \bar{v}_G^{EIT} \quad (4)$$

$$Q_O = A\bar{\alpha}_O \bar{v}_W^{EMF} \quad (5)$$

$$Q_W = A\bar{\alpha}_W \bar{v}_W^{EMF} \quad (6)$$

where $Q$, $\bar{\alpha}$, $\bar{v}$ and $A$ are volumetric flow rate, mean volume fraction, mean velocity and the area of pipe cross section respectively; the subscript indicates the specific gas/oil/water phase, the superscript denotes the applied sensing technique.

Measurement System

Figure 16:
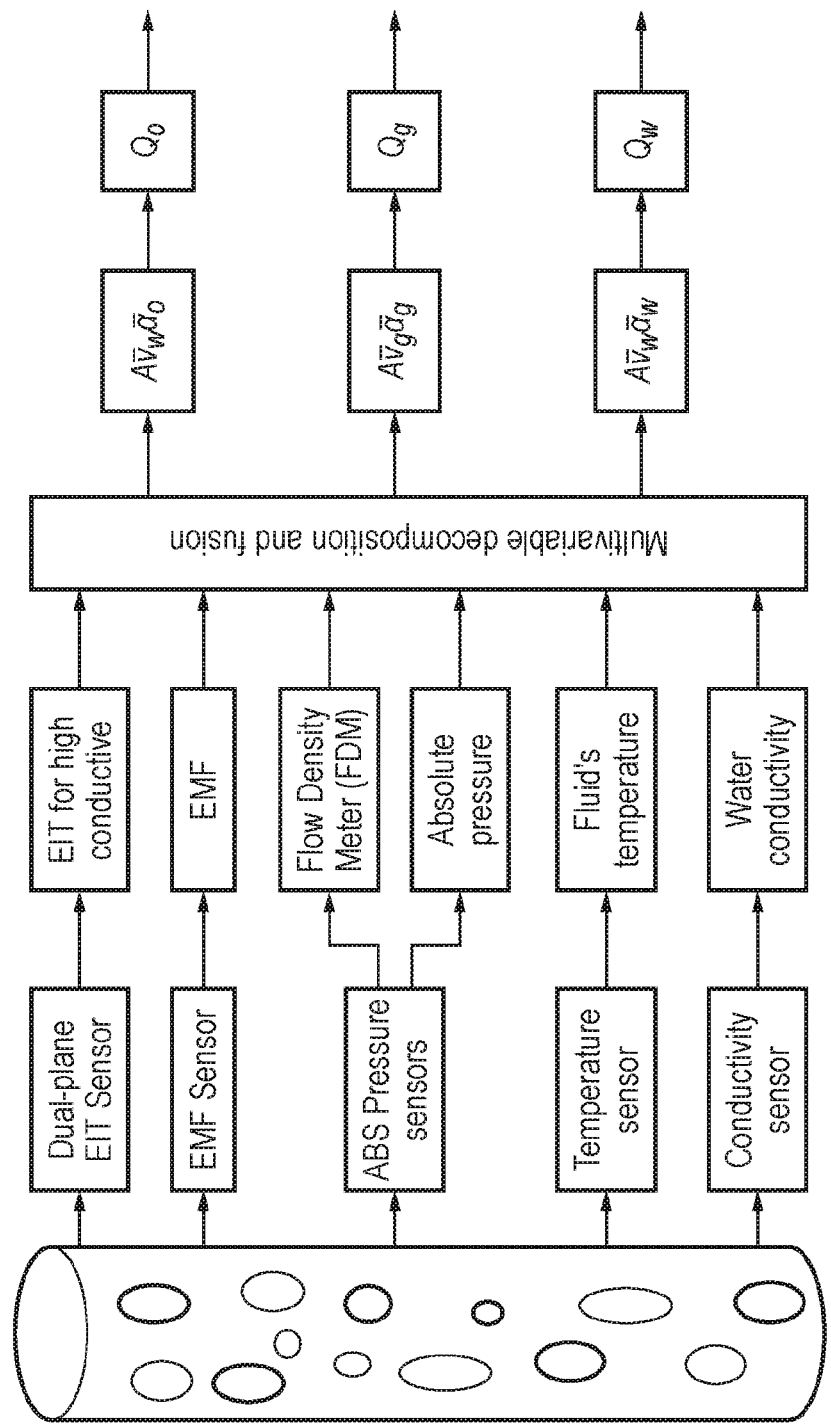
FIG. 16 is a schematic diagram of a three-phase flow measurement system embodying the invention.
Figure 17:
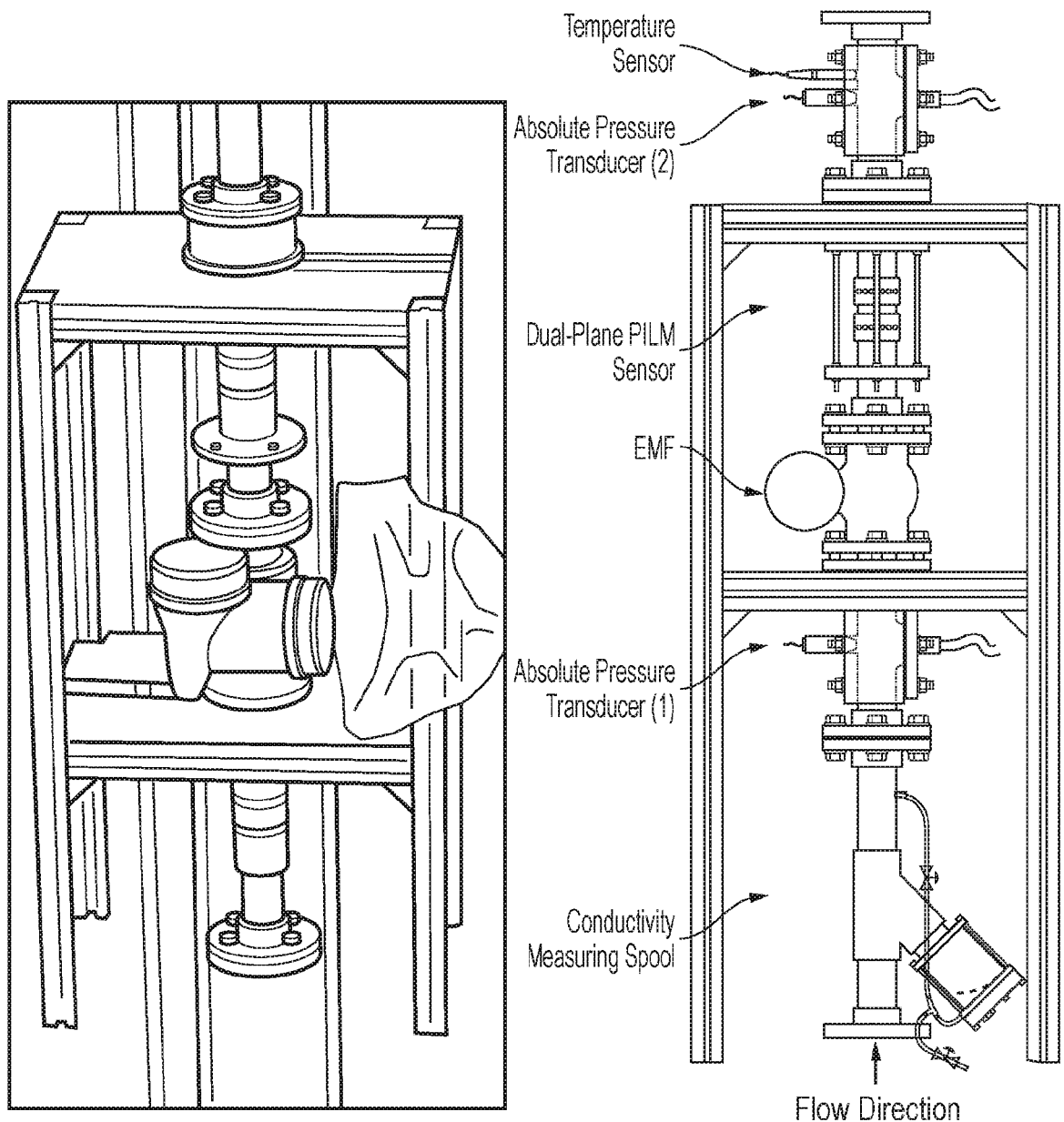
FIG. 17 shows a photograph (left) and line sketch (right) of an integrated measurement system embodying the invention.

The research-prototype three-phase flow measurement system is illustrated as FIG. 16, which is consisted of an EIT (ITS V5r EIT system) with a dual-plane sensor (Jia et al. 2010), an EMF flow meter (OPTIFLUX 4000, from KROHNE), two absolute pressure sensors (PXM209-2.50A10V, from OMEGA), one temperature sensor (RTD-NPT-72-E-MTP-M, from OMEGA) and an in-house-build online conductivity cell. A photograph and line sketch of the integrated sensor is given by FIG. 17. Computer software with graphic interface is used for control of data collection, online data fusion and display.

Corrections, Calibration and Compensations

EIT measurement relies on the relative change of conductivity between conductivities of the mixture ($\sigma_m$) and the water-continuous liquid phase ($\sigma_c$). It is a conventional approach to use Maxwell's mixing-model to derive the volume fraction of the dispersed phase ($\alpha_d$) from the measured conductivity relative change ($\sigma_m/\sigma_c$), viz.:

$$\alpha_d = \frac{1 - \frac{\sigma_m}{\sigma_c}}{1 + 0.5 \times \frac{\sigma_m}{\sigma_c}} \quad (7)$$

As indicated in equation 1, three-phase flow mixture density ($\square_{FDM}$) estimated from the gradiomanometer (FDM) is one of the three basic variables along with those measured by EIT and EMF to enable the three phase measurement. Two absolute-pressure sensors are flush-mounted on a straight section of vertical pipe to derive the differential pressure for the determination of the mixture density as well as the absolute pressure for gas density correction. The use of solid-state pressure sensors in this research work avoids the need of liquid-filled pressure-transmitting tubes in a conventional differential pressure sensor. However, the wide measurement range of the chosen absolute pressure sensors may cause a low sensitivity and therefore a marked measurement error for the derived differential pressure (DP) measurement. A specific differential amplifier is designed with high common voltage rejection ratio to enhance the performance of the DP signal. The DP sensor is calibrated to correct for the offset and the meet the full measurement range. Taking into account the effects of frictional pressure loss, the mixture density $\rho_{FDM}$ can be estimated from the following equation:

$$\rho_{FDM} = \frac{\Delta P_{FDM}}{gh + \frac{2C_f hv^2}{D}} \quad (8)$$

where $\Delta P_{FDM}$ is the derived gradio differential pressure, v the liquid velocity, D the pipe diameter, h the distance between the two pressure sensing points, g the gravitational acceleration constant, $C_f$ the Fanning frictional factor $C_f=0.079Re^{-0.25}$ with the Reynolds number being $Re=\rho/vD/\mu$ ($\mu$ is the liquid dynamic viscosity). The volume fraction of the dispersed phase (e.g. oil or gas) can be deduced, for a water-continuous two-phase flow, as, $$\alpha_d = \frac{\rho_{FDM} - \rho_w}{\rho_d - \rho_w} \quad (9)$$

where $\rho_d$ and $\rho_w$ are the densities of disperse phase and water, respectively.

Since only the relative change of conductivity is used in the data fusion, the actual value of conductivity is less important. The temperature deviation is used for measurement compensation in the system. Therefore, the correctness of temperature measurement or deviation should be checked or calibrated by a calibrated standard temperature meter. The correctness of both absolute and differential pressures is important. They may be calibrated by a set-up with or without a liquid having known density in the system.

Assuming the flow density to be known or measurable as given by equation 9 and the conductivity of the disperse (oil and/or gas) phase is zero, the relative change of conductivity used in the EIT without the conductivity reference (see equation 9) can be simply corrected by the calibration coefficient, η, at any measurement stage, which is presented as, $$\eta \cdot \frac{\sigma_m}{\sigma_c} = \frac{2(1-\alpha_d)}{2+\alpha_d} \quad (10)$$

In multiphase flow measurement, the conductivity of the water-continuous liquid phase may change due to variations in the water temperature and/or salinity (ionic concentration). To obtain robust phase fraction distributions reconstructed by the use of linear back projection algorithm, it is therefore necessary to apply online compensation to the conductivity readings of the continuous water phase. Two methods are embedded in the flowmeter research prototype, which are selectable depending on whether the change is due to the salinity or due to the temperature, based on the measurements from either an online water-conductivity cell (equation 11) or temperature sensor (equation 12).

$$\sigma'_c = k \cdot \sigma_0 \quad (11)$$

$$\sigma'_c = (1 + \lambda \Delta T) \cdot \sigma_0 \quad (12)$$

where $\sigma_0$, $\lambda$ and $\Delta T$ are the original conductivity of the continuous phase, temperature coefficient and change of temperature at the time taking the reference voltage measurement and k is the conductivity cell constant in case of using the online conductivity cell.
Combining all the above effects, the calibration and compensation can be made as, $$\alpha_d = \frac{1 - \frac{\eta \sigma_m}{k \sigma_0}}{1 + 0.5 \times \frac{\eta \sigma_m}{k \sigma_0}} \quad (13)$$

Two- and Three-Phase Flow Measurements

The flow-measurement experiment was conducted on the inclinable multiphase flow facility at Schlumberger Gould Research (SGR). Tap water, kerosene oil and nitrogen gas were used as the test fluids. The test included a large number of combinations of flow conditions, mostly for vertical upward pipe flows, with range of water flow rate ($q_w$) 0.5-15 m³/h, range of oil flow rate ($q_o$) 0.5-10 m³/h, and gas flow rate ($q_G$) 0-42 m³/h, which made the range of gas volume fraction GVF 0-97% [GVF=$q_G$/($q_G$+$q_o$+$q_w$)]. The tests covered oil/water two-phase flows with water cut WC=~30 to 100% [WC=$q_w$/($q_o$+$q_w$)]; oil/water/gas three-phase flows with similar water-cut range and GVF at line pressure up to 2.2 bar. For vertical upward high-flow rate oil/water flows, the velocity slip between the oil and water phases is considered to be negligible, hence the water fraction is considered to be the same as the water cut. Note that water to liquid ratio WLR=$\alpha_w$/($\alpha_o$+$\alpha_w$). Hence WLR=water cut when there is no oil-water velocity slip ($v_w$=$v_o$). Measurement scope of the prototype system is for oil-in-water or water-continuous flows based on the principle of EIT.

Oil-Water Two-Phase Measurements

Figure 18:
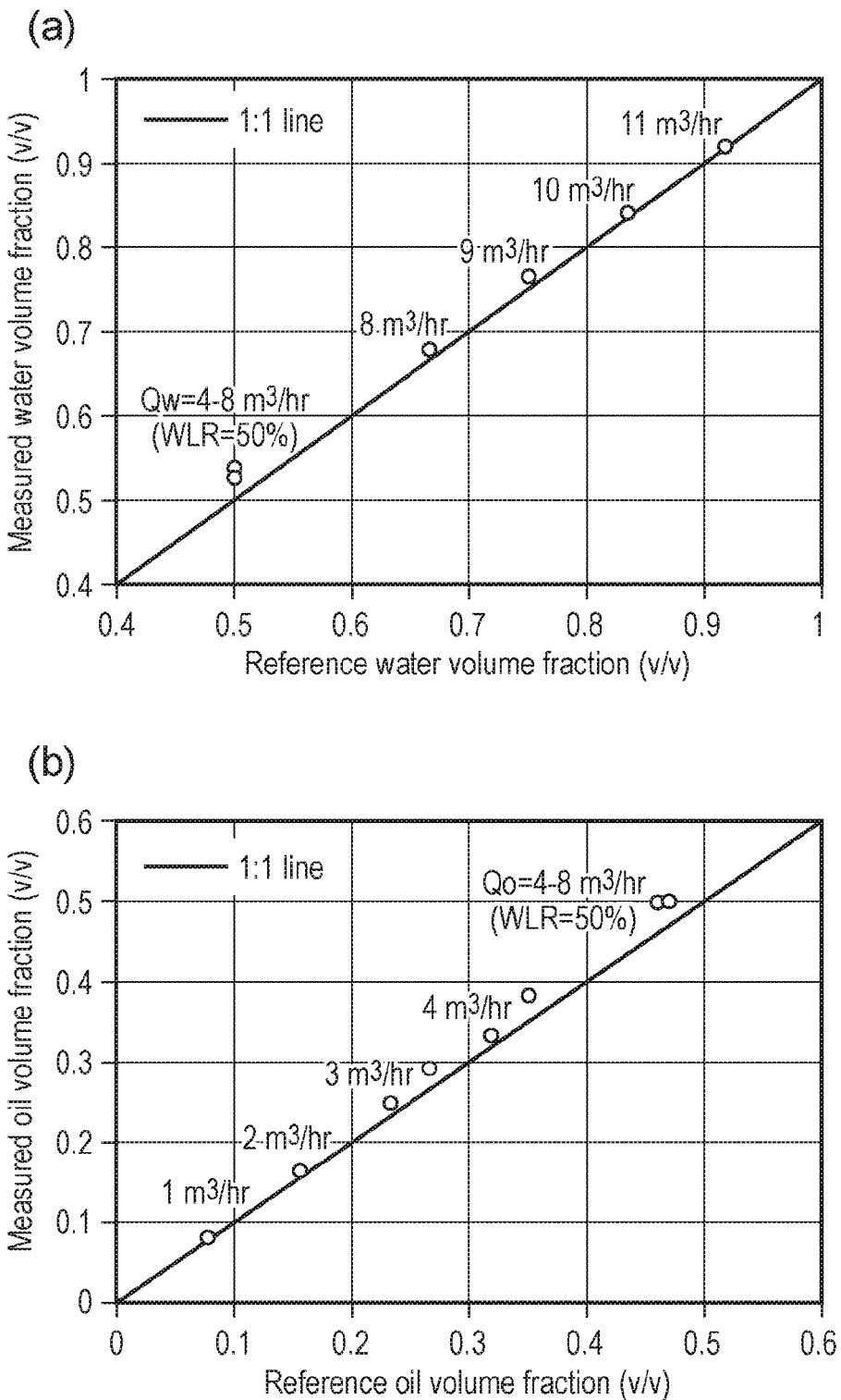
FIG. 18 shows comparison results of measured oil-in-water two-phase flow with that of reference, (a) oil volume fraction, (b) water volume fraction, (c) water flow rate, (d) oil flow rate in an embodiment of the invention.
Figure 18:
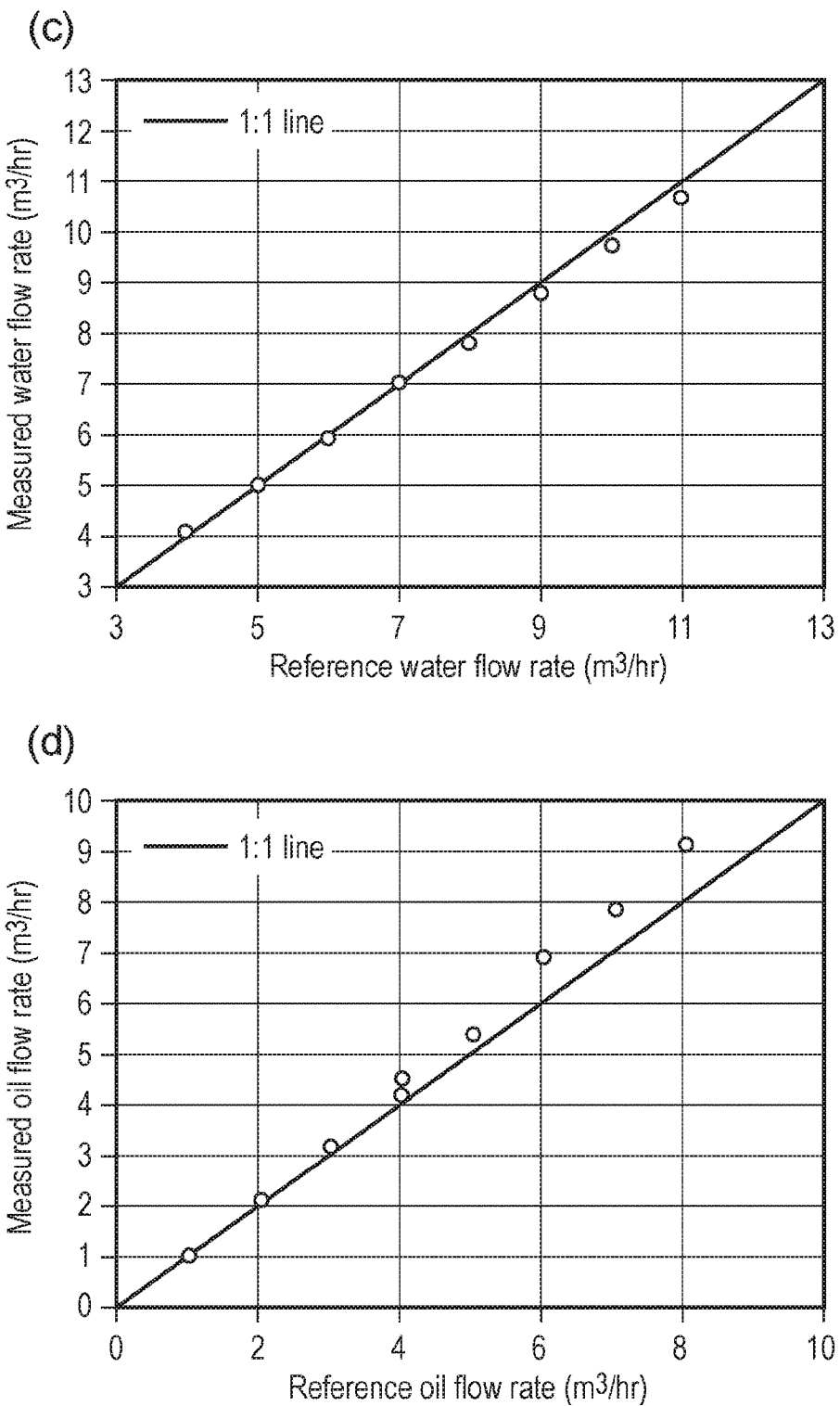

FIG. 18 illustrates the comparison results of measured mean oil-in-water two-phase flow with that of reference. By observing FIG. 18b, it is apparent that the deviation of the EIT-measured oil volume fraction from the non-slip reference value increases with increasing oil volume fraction. Since the water volume fraction is obtained from the EIT-measured mean oil volume fraction, similar deviation is mirrored in the measured water volume fraction (FIG. 18a). For oil-water flow-rate measurement, FIG. 18d shows an increasing over-estimation of the measured oil flow rate relative to the reference, with the increase in the oil flow rate. The measured water flow rate (with the mean water velocity derived from the EMF), on the other hand, largely closely follows the flow-loop reference (FIG. 18c). From the above observations, it can be concluded that the large deviation in the measured oil flow rate is attributed to the error in the mean oil velocity obtained by the EIT pixel-wise cross-correlation. (In the oil-water flow test results shown here, there is no assumption of an equal mean velocity between the oil and the water phases.).

Gas-Oil-Water Three-Phase Measurements

Figure 19:
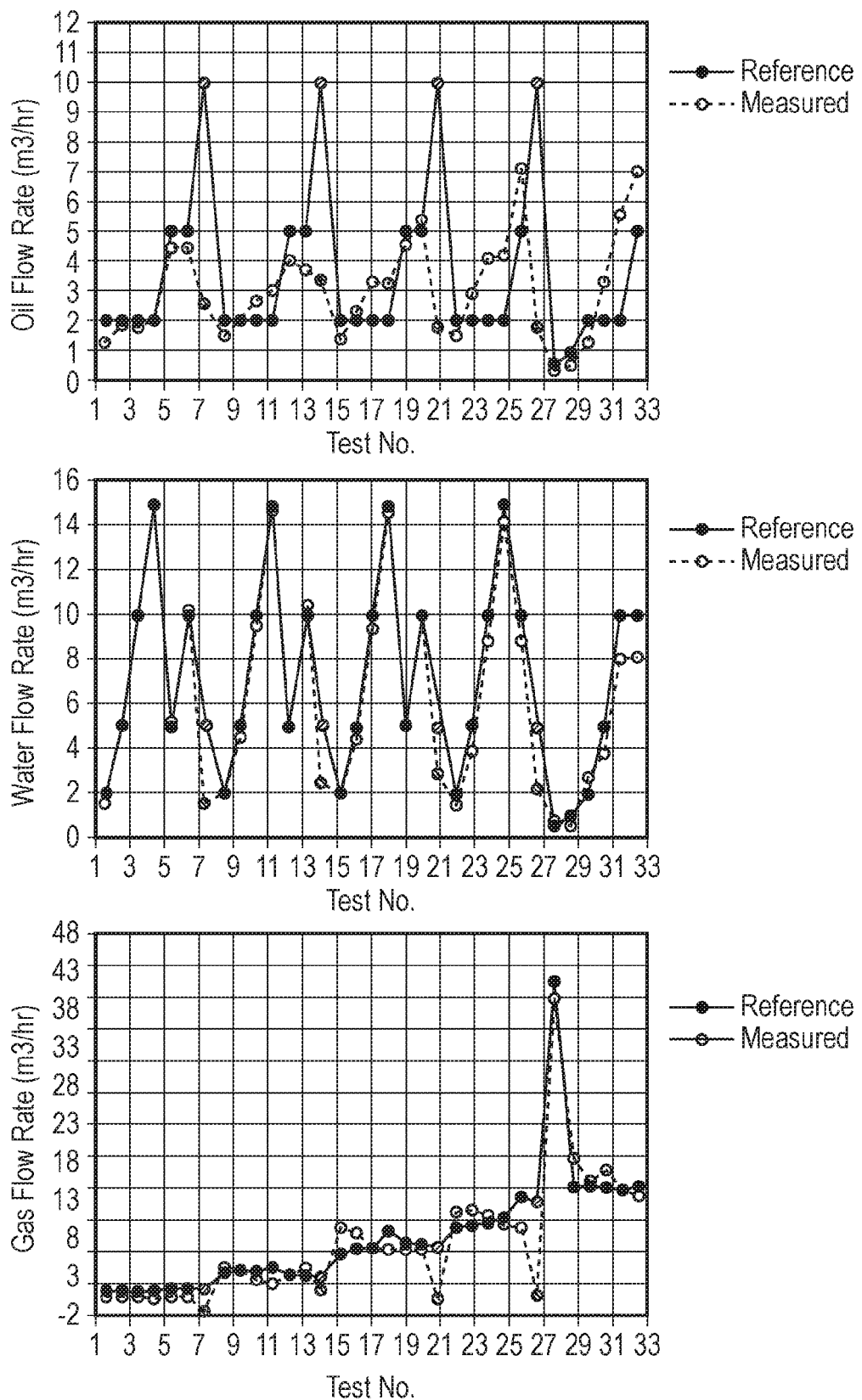
FIG. 19 shows overall results of gas-oil-water three-phase flow measurement for 33 flow conditions, (a) oil flow rate, (b) water flow rate, (c) gas flow rate in an embodiment.

The overall measurements, including the reference measurements from SGR for 33 flow conditions are summarised by FIG. 19. All the measurements were carried out within water continuous region (WLR>50%), except for four test conditions, which were carried out within oil continuous region (WLR=33%). It is well known that the phase-inversion (water cut) for low viscosity kerosene and water mixture is around 35% WLR. These four conditions are highlighted by blue-colour data points as reference values and the corresponding measured values are represented by red-colour data points. It is quite clear that a reasonable agreement with the references can be observed for all the measured flow rates within water continuous region. However, for the measured flow rates of oil continuous flows a very large deviation is apparent from the reference. By observing the trend of measured oil flow rates, it can be seen that the level of deviation is more pronounced than that of the measured water flow rates and that of the measured gas flow rates; the deviation grows more with the increase of oil flow rate. On the other hand, the comparison results of gas flow rate between the measured and reference values suggest that higher deviation in the oil flow rate is associated with higher gas flow rates, as shown in FIG. 19c (bottom). The possible reason for this is that the higher gas flow rate does not allow the existence of a water-rich conductive-layer around the EIT electrodes that are flush-mounted with the pipe wall.

Figure 20:
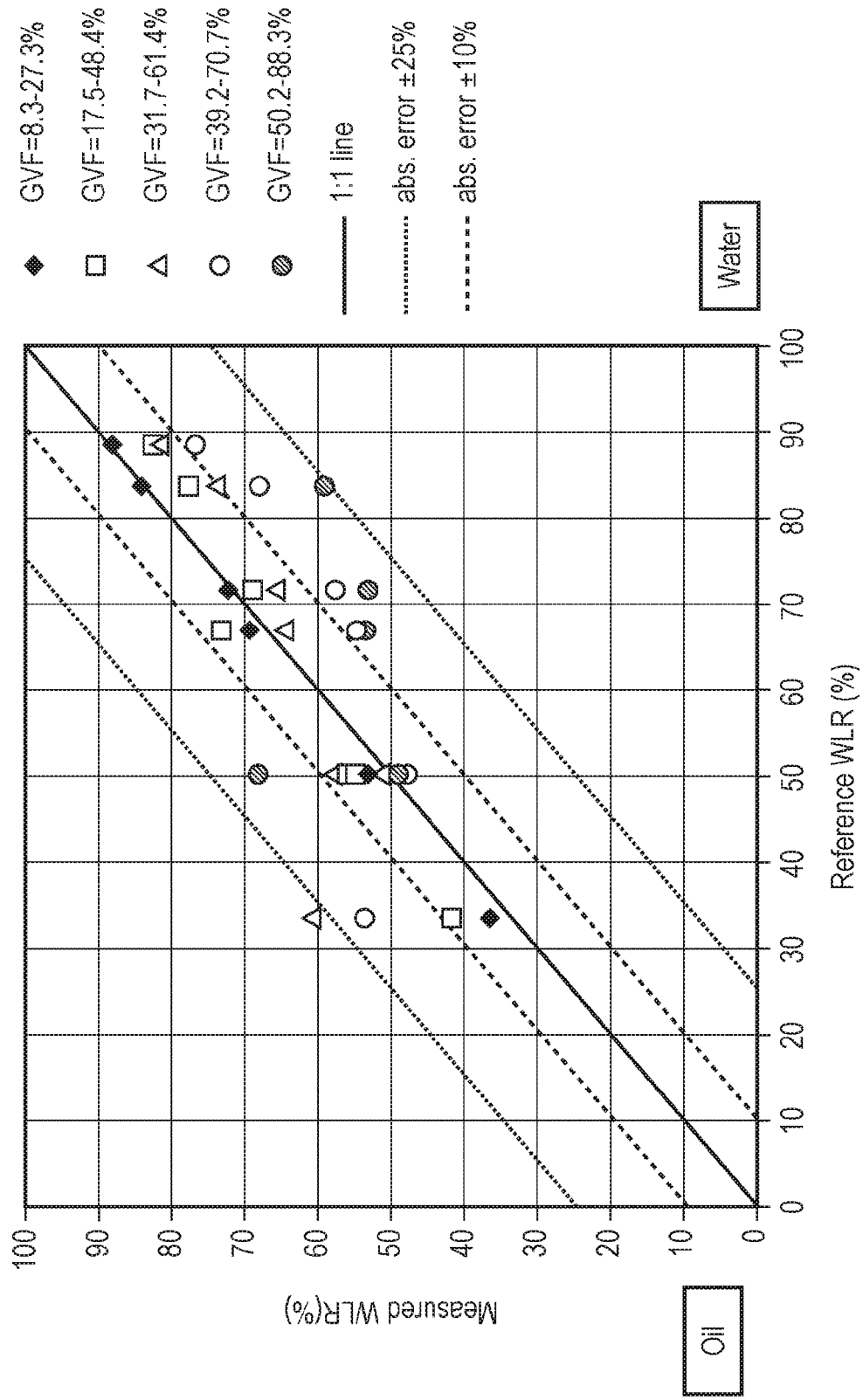
FIG. 20 shows the measured water cut (WLR) compared with the reference for different range of GVFs (with the ±10% and ±25% absolute-error boundaries shown) in an embodiment.

To further illustrate the uncertainties in the flow-measurement and identify the operating region in terms of WLR and GVF, the comparison between the estimated WLR and the reference WLR is shown in FIG. 20. It is can be seen that, within the range of 45%-100% WLR and the range of GVF 0%-45%, the estimated WLR has an absolute-error within ±10%.

Figure 21:
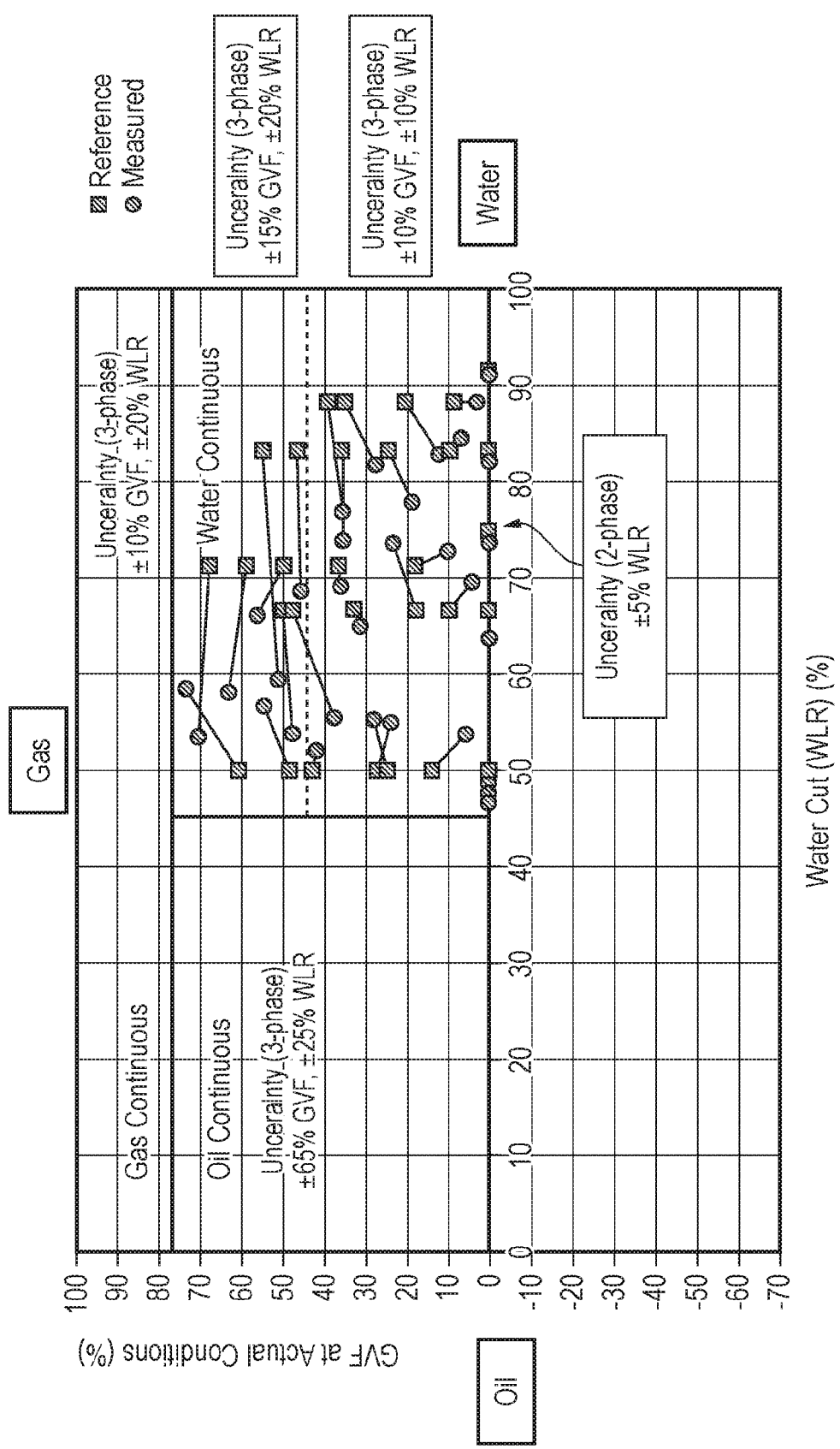
FIG. 21 is a GVF-vs-WLR Composition map summarizing the research-prototype measured GVF and WLR compared with the respective references, for two- and three-phase vertical upward flow within water-continuous region in an embodiment.

FIG. 21 presents all the results obtained from two- & three-phase vertical upward flow tests carried out in SGR, as a GVF-vs-WLR composition map, with water-continuous and oil-continuous regions indicated, in blue and red colours, respectively. The boundary of oil-and water-continuous regions is shown at WLR=45% as an example. The gas continuous flow region is roughly illustrated as being between 78%-100% GVF. In the composition map the reference and measured water cut is plotted against the reference and measured GVF. The reference values are highlighted in green data points, while the measured values are represented by red ones. Each measured value is connected to the corresponding reference value through a straight line, with its projected lengths in the WLR-axis and GVF-axis indicating the discrepancies (in absolute-error in percentage) in the WLR and GVF, respectively.

FIG. 21 indicates that the measurements of two-phase (oil-water) flow, which are distributed along the x-axis within water continuous region, have an uncertainty of ±5%. On the other hand, the measurements for three-phase flow have ±10% uncertainty in WLR and GVF within the water-continuous region (45%-100% WLR) and within the GVF range of 0%-45%. The performance of the WLR and GVF measurement deteriorates for GVF>45%, where the WLR-error doubles. It is worth pointing out that any measurement carried out near the oil-continuous region (33% WLR) is associated with an uncertainty of ±65% GVF and ±25% WLR, due to that the EIT-based measurement is limited to water-continuous flow only.

Figure 22:
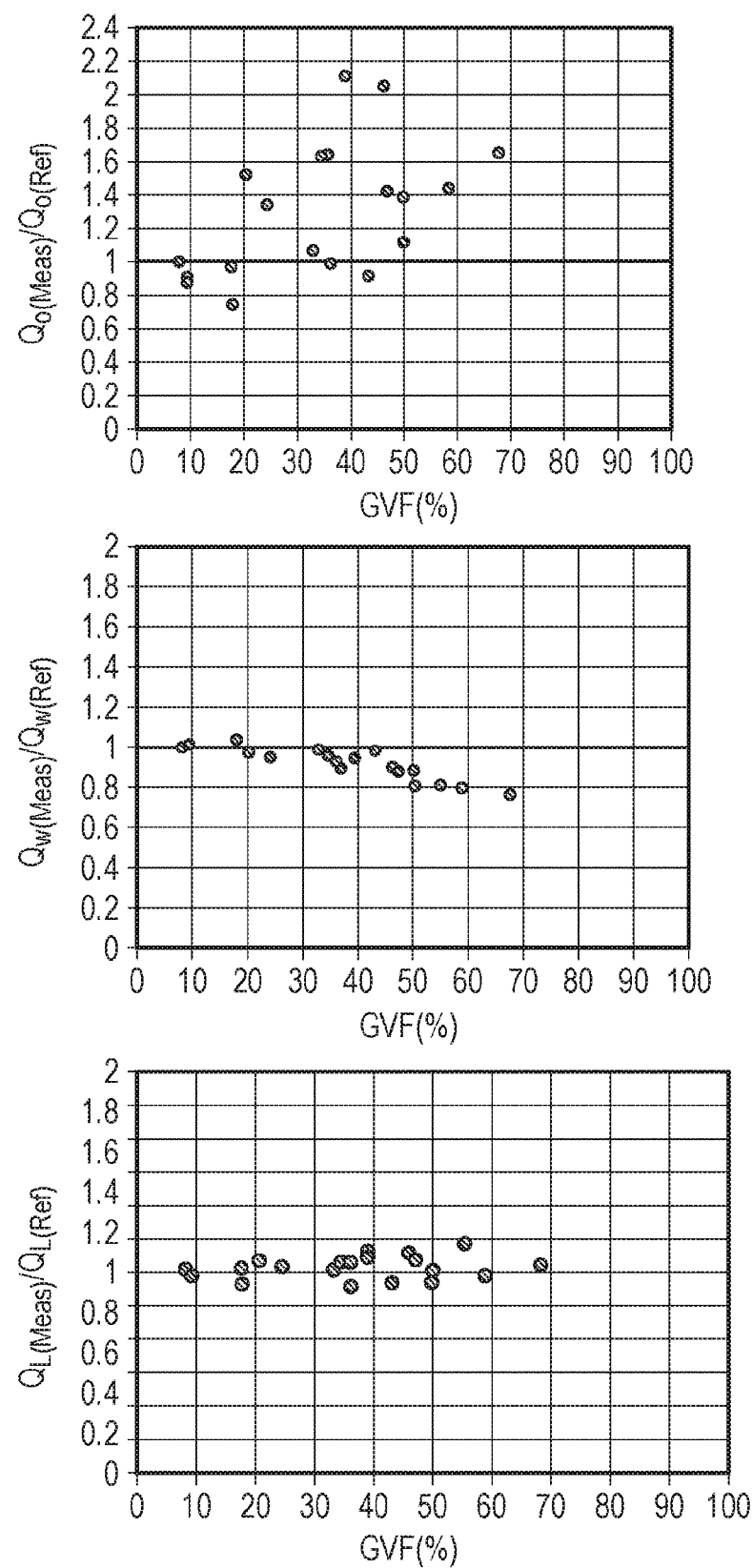
FIG. 22 shows ratios of the measured to the reference liquid phase flow rates vs. GVF; (a) (top) oil flow rate, (b) (middle) water flow rate and (c) (bottom) liquid flow rate.

Further analysis of ratio of oil flow-rate, water flow-rate and the liquid flow-rate to their respective reference, plotted against the GVF as given in FIG. 22, may reveal the major error sources and suggest appropriate corrections. FIG. 22a shows that the relative error of the oil flow rate is associated with GVF increase and is up to 220%. The relative error of the water flow rate is up to about −20%, but is within ±10% for GVF<~45% (FIG. 22b). However, the relative error of the total liquid rate is largely around ±10% (FIG. 22c). This indicates that the part of errors between oil flow rate and water flow rate may be complementary, which may come from the same error sources. Further research is needed to fully understand the source of the measurement errors.

Discussions

This sub-section has presented initial gas-oil-water three-phase flow measurement results from an electrical impedance tomography geared by an electromagnetic flow meter and a gradiomanometer flow-mixture density meter, and assisted by online water-conductivity and temperature sensors. The targeted measurement is limited for vertical upward flow with water continuous flow.

The measurements of two-phase (oil & water) flow have an uncertainty of ±5%, which will be much better than ±5% after a linear correction is applied (Faraj et al. 2014). For three-phase measurement, the results in FIG. 22 indicate that the error of the measured water flow rate is within ±10% when the flow is water continuous (i.e. has a higher WLR>45%) and low GVF (GVF<~32%). The error of the estimated oil flow rate is within ±10% when the flow has a WLR>45% and a low GVF<~10%.

The measured oil flow rate has a pronounced deviation more than that in the measured water flow rate and gas flow rate. The deviation is further increased with increase of oil flow rate to a point where a larger deviation can be noticed, which is again, similar to estimated water flow rate; the high measurement error is generated within the oil continuous region (33% WLR). The measurement errors increase with the increasing of GVF, which may be due to the limited capacity of EIT in handling the high-fraction of dispersed (oil and gas) phases, as well as the limited imaging spatial resolution from the dual-plane 8-electrode sensor in the use. The time of EIT sampling is too short to present the steady state of flow would be other source of errors. Possibilities can also be due to the 'malfunctioning' of the FDM method for a non-homogeneous flow, the lack of desired stability of differential-pressure measurement from two absolute pressure sensors.

Finally it can be concluded that the measured phase flow rates in three-phase flows are in reasonable agreement with the that of the reference within ±10%) within the range of water continuous flow region (WLR>45%) and moderate GVF<45%. Further work to improve the performance is ongoing, including, calibration, slip velocity correction and flow regime assessment, improved FDM method and modelling, enhanced EIT imaging resolution and sampling.

REFERENCES FOR SUB-SECTION 2

APPEL, M., FREEMAN, J. J. AND PUSIOL, D., (2011), Robust multi-phase flow measurement using magnetic resonance technology, *Proceedings SPE Middle East Oil and Gas Show* (Manama, Bahrain, September 2011) SPE 141465.

DENG, X., DONG, F., XU, L. J., LIU, X. P. AND XU, L. A., (2001), The design of a dual-plane EIT system for cross correlation measurement of bubbly gas/liquid pipe flow, *Meas. Sci. Technol.* 12, pp. 1024-1031.

FARAJ, Y., WANG, M. JIA, J., WANG, Q., XIE, C. G., ODDIE, G., PRIMROSE, K. AND QIU, C., (2014), Measurement of Vertical Oil-in-water Two-phase Flow Using Dual-modality ERT/EMF System, *5th International Workshop on Process Tomography*, Jeju, South Korea.

GEORGE, D. L., TORCZYNSKI, J. R., SHOLLENBE-GER, K. A., O'HEN, T. J. AND CECEIO, S. L., (2000), Validation of electrical-impedance tomography for measurements of material distribution in two-phase flows, *Internat. J. Multiphase flow*, 26, pp. 549-581.

JIA, J., WANG, M., SCHLABERG, H. I. AND LI, H., (2010), A Novel Tomographic Sensing System for High Electrically Conductive Multiphase Flow Measurement, *Flow Meas. & Instru.* 21, pp. 184-190

LUCAS, G. P., CORY, J., WATERFALL, R., LOH, W. W. AND DICKIN, F. J., (1999), Measurement of the solids volume fraction and velocity distributions in solids-liquid flows using dual-plane electrical resistance tomography, *J Flow Meas. Instrum.* 10 (4), pp. 249-258.

MOSOROV, V., SANKOWSKI, D., MAZURKIEWICZ, L. AND DYAKOWSKI, T., (2002), The 'best-correlated pixels' method for solid mass flow measurements using electrical capacitance tomography, *Meas. Sci. Technol,* 13, pp. 1810-1814.

SHARIFI, M. AND YOUNG, B., (2013), Electrical Resistance Tomography (ERT) applications to Chemical Engineering, *Chem. Eng. Res. Des*, In press, Available online 25 June (2013).

THORN, R., JOHANSEN, G. A. AND HJERTAKER, B. T., (2012), Three-phase flow measurement in the petroleum industry, *Meas. Sci. Technol,* 24, 012003 (17 pp).

VAN SANTEN, H., KOLAR, Z. I. AND SCHEERS, A. M., (1995), Photon energy selection for dual energy γ- and x-ray absorption composition measurements in oil-water-gas mixture, *Nucl. Geophysics*, 9, pp. 193-202.

WALLIS, G., B., (1969), *One Dimensional Two Phase Flow*, USA, McGraw-Hill Book Company.

WANG, M., JONES, T. F. AND WILLIAMS, R. A., (2003), Visualisation of asymmetric solids distribution in horizontal swirling flows using electrical resistance tomography, *Chem. Eng. Res. Des,* 81 (A8), pp. 854-861.

WANG, M., MA, Y., HOLLIDAY, N., DAI, Y., WILLIAMS, R. A. AND LUCAS, G., (2005), A High Performance EIT System, *IEEE Sensors Journal*, 5 (2), pp. 289-299.

XIE, C. G., ATKINSON, I. AND LENN, C., (2007), Multiphase Flow Measurement in Oil and Gas Production, *5th World Congress on Industrial Process Tomography*, Bergen, Norway, 3-6 Sep. 2007, pp. 723-36.

YORK, T., (2001), Status of electrical tomography in industrial applications, *J. Electron. Imag.* Vol. 10.3

Comments on Sub-Section 2

This contains further description and figures of certain embodiments of the invention. For example, referring to FIG. 16, this illustrates how, in this embodiment of the invention, the system comprises a dual-plane EIT sensor (i.e. electrical impedance tomography sensor), an EMF sensor, pressure sensors, a temperature sensor, and a conductivity sensor which is arranged to provide a signal indicative of water conductivity (i.e. the conductivity of the continuous phase in the mixed-phase sample). The processing means is arranged to calculate, from the various sensor signals and data generated using the tomography apparatus, oil flow velocity, gas flow velocity, water flow velocity, oil volumetric flow rate, gas volumetric flow rate, and water volumetric flow rate. Thus, by incorporating the various sensors illustrated and described in this sub-section the processing means is able to provide an indication of mean volume fractions and mean flow rates of each of the three phases present in the sample.

Description Sub-Section 3

This sub-section is concerned with the Significance of On-line Conductivity Calibration for EIT.

Summary of Sub-Section 3

Electrical Impedance Tomography (EIT) provides the images of multiphase flows based on electrical conductivity distribution. Before measuring multiphase flows, EIT takes an instant snapshot on single continuous phase as a reference. The reference file significantly determines the quality of the reconstructed images of flows. During dynamic industrial process, the temperature of continuous phase varies due to the effects from the internal energy conversion, the changes of ambient temperature and ionic concentration in process, which causes the change of continuous phase conductivity. Without conductivity calibration, EIT takes this conductivity change into account of multiphase mixture and produces large drift error on measurement results. In this sub-section, two methods are introduced to on-line calibrate the conductivity value for reference file and eliminate drift error. The first method is to test the flow temperature continuously and indirectly calibrate conductivity using linear relationship between temperature and conductivity. In the second method, the conductivity of continuous phase is monitored via a specially designed conductivity cell for directly on-line calibration. The methods were evaluated with both static and experimental set-ups. Results obtained from an air-water and air-oil-water flow rigs are reported. The proposed on-line calibration method can help EIT to monitor long-term dynamic process with stronger resistance to systemic error.

Introduction to Sub-Section 3

Electrical Impedance Tomography (EIT) is an imaging technology for the multiphase flow measurement. It is able to provide the information of dispersed phase on distribution, concentration and velocity. The first step of operating EIT is to take a baseline sensing on humongous continuous phase as a reference, which likes an instant snapshot of the conductive liquid phase. After the dispersed phase is introduced into the pipeline or vessel, each individual sensing on multiphase flow will compare with the pervious reference file. The relative impedance difference between two sensing is utilised to gain images of multiphase flow. However, during dynamic industrial process, the conductivity of continuous phase varies due to the effects from the internal energy conversion, the changes of ambient temperature and ionic concentration in process. Without conductivity calibration, EIT could not take the conductivity change into account and produces large drift error to measurement results. In Sharifi's EIT work, the concentration of solid contents is empirically correlated with temperature, conductivity and composition (Sharifi, 2013). Two alternative conductivity calibration methods will be discussed in this sub-section.

Temperature Calibration

The electrical conductivity σ of material can be defined as:

$$\sigma = \frac{L}{RA} \quad (1)$$

where R, A and L are the electrical resistance, the cross-sectional area and the length of the material respectively.

One of factors influence electrical conductivity is temperature (Hayashi, 2004). With respect to initial conductivity $\sigma_0$ at temperature $T_0$, the conductivity at temperature $T_r$ is approximated into a linear relationship as expressed in equation (2) when the temperature change $T_r-T_0$ is not much, where k is called temperature coefficient.

$$\sigma_r = (1 + k \cdot (T_r - T_0)) \cdot \sigma_0 \quad (2)$$

$Z_0$ are regarded as equivalent impedance of humongous continuous phase at temperature $T_0$. $Z_r$ is the new impedance after temperature of continuous phase changes to $T_r$. By combining equation (1) and (2), the ratio of resistance $Z_r$ and $Z_0$ is denoted in equation (5).

$$\frac{Z_r}{Z_0} = \frac{1}{(1 + k \cdot (T_r - T_0))} \quad (3)$$

Reference impedance $Z_0$ represents homogenous water flow at the beginning of measurement. Two or three phase flows are measured again and referred as measurement impedance $Z_m$. If the temperature of flow is continuously monitored, measurement drift due to temperature change can be compensated online.

In Sensitivity Back-Projection (SBP) algorithm, the process of temperature compensation is $$\frac{\sigma_m}{\sigma} = 1 - S \cdot \frac{Z_m - Z_r}{Z_r} = 1 - S \cdot \frac{Z_m - (Z_0/(1 + k \cdot \Delta T))}{Z_0/(1 + k \cdot \Delta T)} \quad (4)$$

In Modified SBP algorithm, the process of temperature compensation is $$\frac{Z_m}{Z_r} = (1 + k \cdot (T_r - T_0)) \cdot \frac{Z_m}{Z_0} \quad (5)$$

-continued $$\frac{\sigma_m}{\sigma_0} = \frac{1}{S \cdot \frac{Z_m}{Z_r}} = \frac{1}{S \cdot (1 + k \cdot (T_r - T_0)) \cdot \frac{R_m}{R_0}} \quad (6)$$

This is a straightforward compensation method. However, temperature coefficient k is an empirical parameter fitted from measurement data. Different chemical solution has different k value. Moreover, when the temperature varies over a large temperature range, the linear approximation is not valid and a more complex correlation should apply. Therefore, a better method of compensating the conductivity change is to directly measure conductivity on-line. A novel approach is introduced in next section.

Conductivity Calibration

Figure 23:
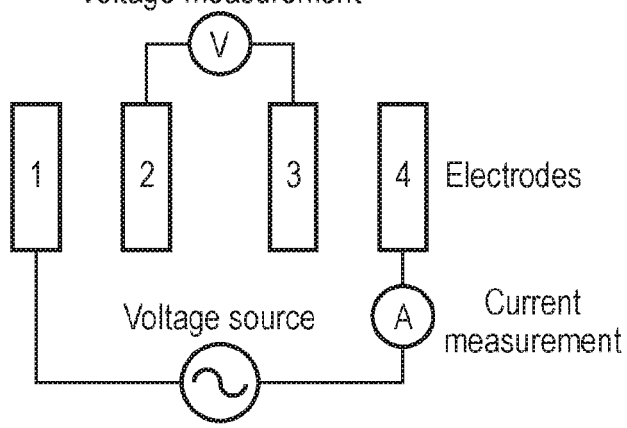
FIG. 23 shows a circuit of conductivity measurement in an embodiment.

A novel structure of conductivity cell for on-line measurement and compensation of EIT is designed. The principle of conductivity measurement is shown in FIG. 23. An alternating voltage is applied across electrode 1 and 4. The consumed current I and the response voltage V are sensed across electrode 2 and 3. The conductivity σ is computed using equation (7) below.

$$\sigma = k \frac{I}{V} \quad (7)$$

where k is a cell constant and determined by the geometry of sensor. The division of V and I is referred as mutual admittance, which is proportional to conductivity.

Figure 24:
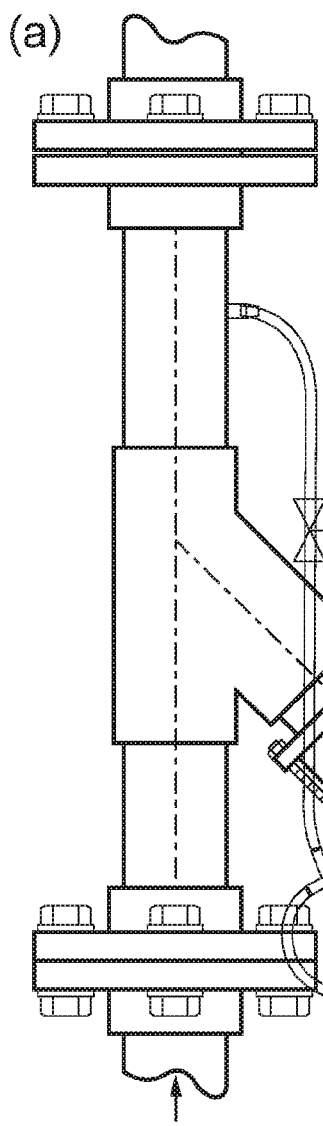
FIG. 24 shows an assembly of the conductivity sensor on the flow pipe in an embodiment.
Figure 24:
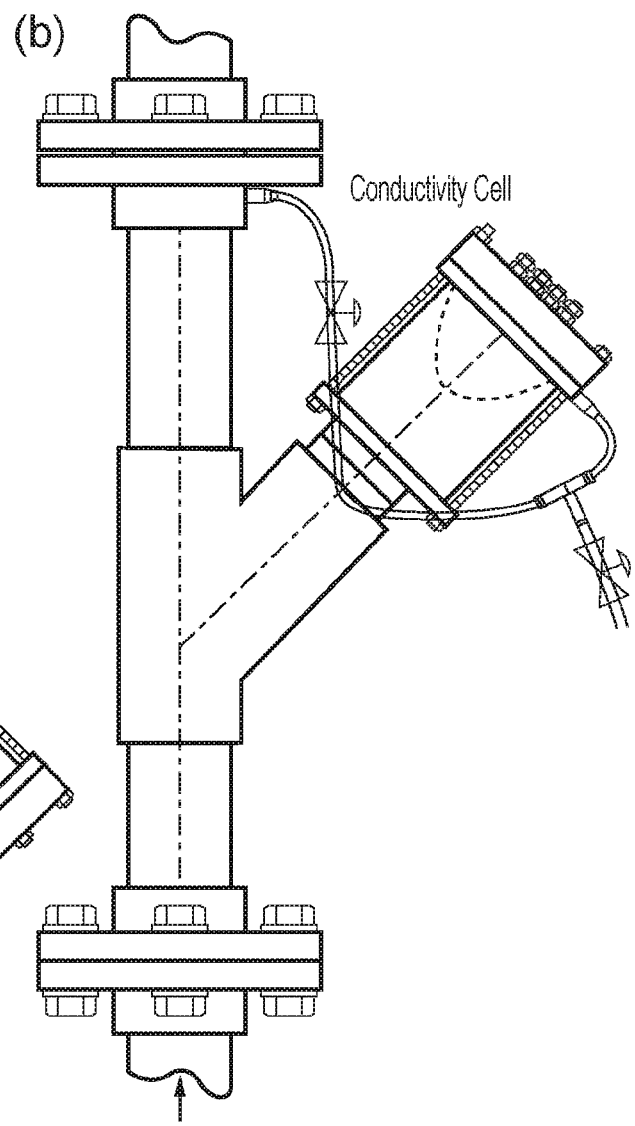

The conductivity of the conductive liquid measured on-line is used for real-time conductivity compensation due to changes in ionic concentration or temperature. The assembly of the conductivity cell is illustrated in FIG. 24. For the applications of gas-water or oil-water flow, the cell chamber is coupled with a pipe section through a 45° downwards pipe fitting (FIG. 24(a)). Because each phase has different density, natural separation process takes place in the chamber. Water is accumulated in the lower space of the chamber. Four stainless steel electrodes are arranged in an equi-spaced fashion and mounted on the bottom of the chamber to directly contact with the fluid in the cell. To ensure the conductivity of continuous phase in the main flow loop is refreshed rapidly, a flexible flush tube connects the low pressure point along the vertical pipe section and the bottom of the chamber. The contained fluid within the cell is constantly circulated with main flow loop. Two flanges are fixed at either end of the pipe section to facilitate installation of the conductivity spool in any vertical section of a flow line. A curved metal screen (mesh) is used to separate the effective measuring region from fast moving flow and prevent disturbance caused by the other constituent phases. For the applications of solid-water flow, the cell chamber is coupled with a pipe section through a 45° upwards pipe fitting (FIG. 24(b)).

Static Test

Figure 25:
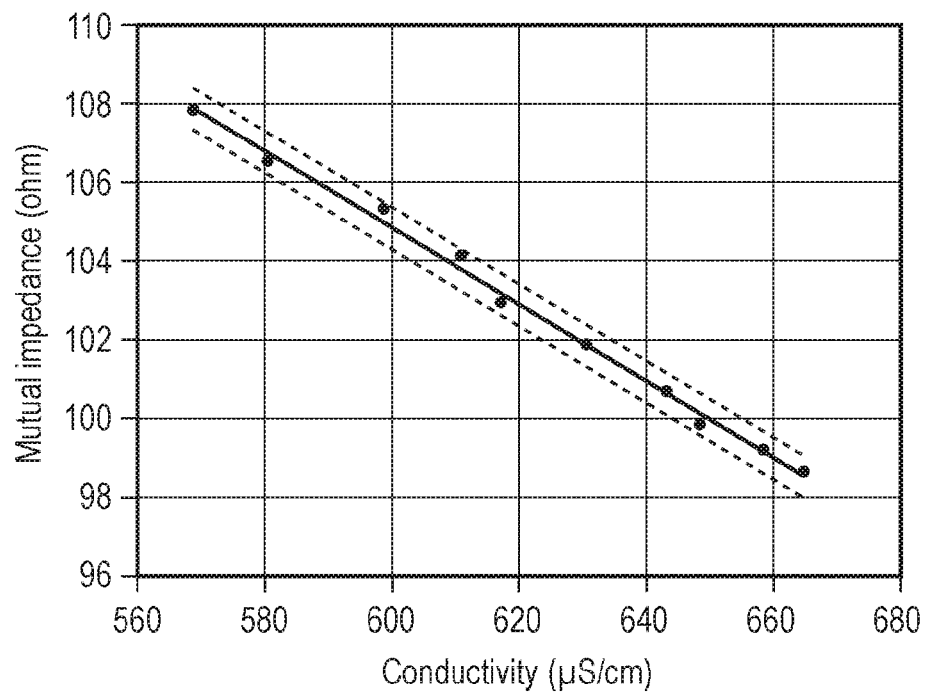
FIG. 25 illustrates a relationship between mutual impedance and conductivity in static setup in an embodiment.

The static sensitivity of the conductivity cell was tested first. Tap water was heated to 48° C. and poured into the cell chamber. Leave tap water cooled down naturally to 39° C. The conductivity of water was recorded by a commercial conductivity probe (Cyberscan PC6500) during this process. FIG. 25 demonstrates the strong linear relationship between water conductivity and mutual impedance obtained from the conductivity cell. Two dashed straight lines indicate the ±0.5% error range of the solid linear trend line.

Dynamic Test

Figure 26:
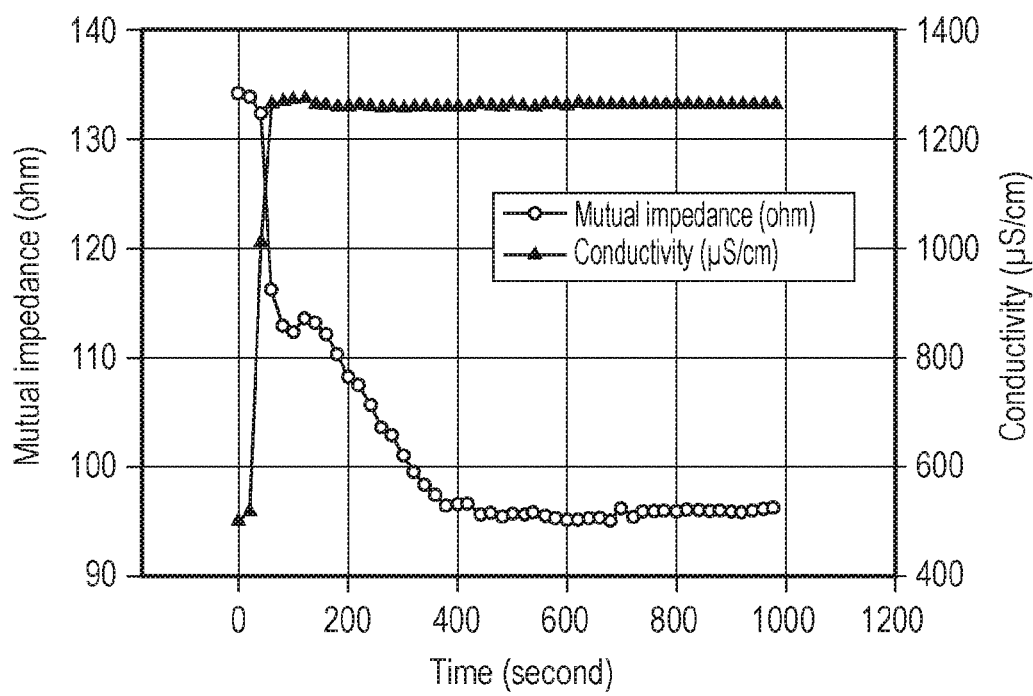
FIG. 26 illustrates dynamic response of conductivity cell in an embodiment.

To test the dynamic response of the conductivity cell, the conductivity cell unit was inserted in the flow loop at the University of Leeds (Olerni, 2013). Water conductivity in the tank was measured using the same commercial conductivity probe. The mutual impedance was read from the conductivity cell. The water flow rate in the loop was kept at 0.73 m3/hr. After 150 g NaCl was added into the water tank, as shown in the black curve in FIG. 26, it took 60 second for the conductivity in the water tank to be increased and stabilised. The blue curve showed the mutual impedance inside the conductivity cell chamber took approximate 400 second to reach steady. It is believed that the flow rate of the multiphase flow and the diameter of the flush tube affect the dynamic response of the conductivity cell.

Figure 27:
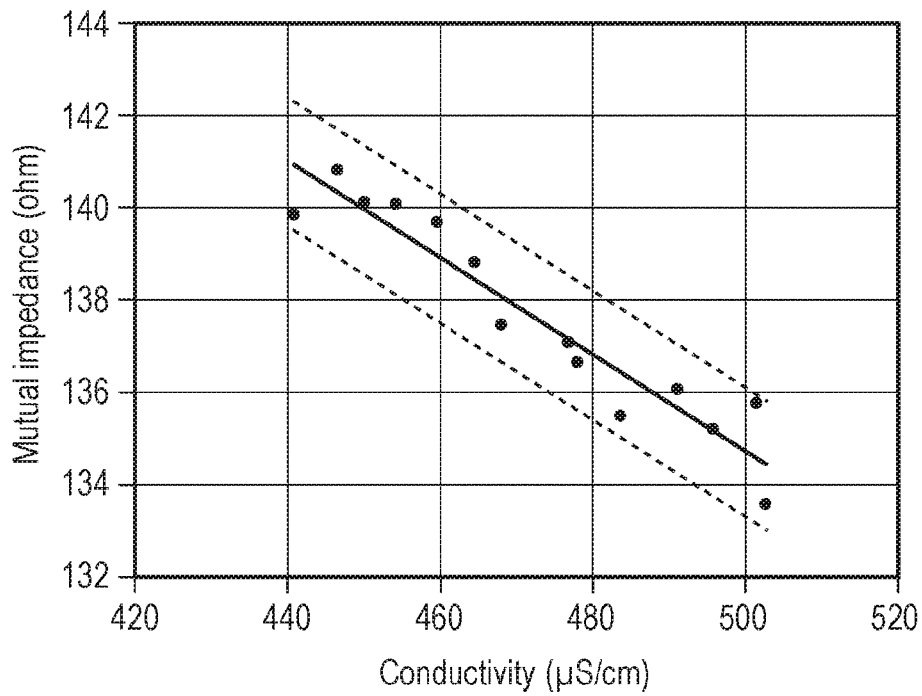
FIG. 27 shows the relationship between mutual impedance and conductivity in dynamic setup in an embodiment.

The conductivity cell was test in air-water two-phase flow. The flow ran for 30 minutes at 0.73 m³/hr inlet water flow rate was and 0.9 m³/hr inlet air flow rate. During the test, the separation of air water took place effectively and no air bubble entering the chamber was observed. The temperature of flow was heated up from 22.0° C. to 28.5° C. by the pump. FIG. 27 does not present as strong linear relationship between mutual impedance and conductivity temperature as FIG. 25 in static test, which means the circulation of water inside the chamber brings interference to conductivity measurement. Two dashed lines indicate the ±1% error range of the solid linear trend line.

Figure 28:
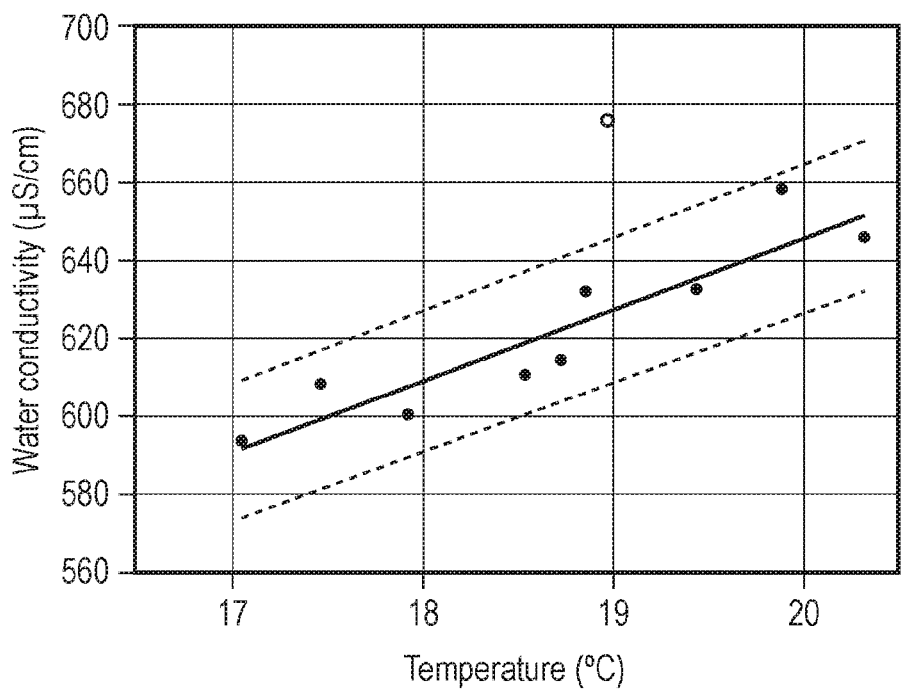
FIG. 28 shows the relationship between temperature and conductivity in dynamic setup in an embodiment.

The air-oil-water three-phase flow experiment was carried out at Schlumberger Gould Research, Cambridge, UK. The flow temperature rose from 17.06° C. to 20.32° C. and water conductivity measured from the conductivity cell was monitored accordingly. The inlet flow rate of each phase, flow temperature and water conductivity are listed in Table 1 below. The correlation between water conductivity and flow temperature is shown in FIG. 28. The red dot is regarded as an outlier and ignored. It might because this flow condition has the lowest water cut, which affects the water circulation in the chamber. Two dashed lines indicate the ±3% error range of solid linear trend line.

TABLE 1

| Conductivity change of air-oil-water three-phase flow | | | | |
|---|---|---|---|---|
| Qa (m³/hr) | Qo (m³/hr) | Qw (m³/hr) | Temperature (° C.) | Water conductivity (μS/cm) |
| 2 | 2 | 5 | 17.06 | 593.3 |
| 2 | 2 | 10 | 17.46 | 608.1 |
| 5 | 2 | 10 | 17.93 | 600.1 |
| 15 | 5 | 5 | 18.54 | 610.2 |
| 15 | 5 | 10 | 18.74 | 614.1 |
| 15 | 2 | 10 | 18.86 | 631.6 |
| 20 | 2 | 5 | 18.98 | 675.7 |
| 2 | 2 | 5 | 19.44 | 632.2 |
| 2 | 2 | 10 | 19.89 | 658.1 |
| 5 | 2 | 10 | 20.32 | 645.5 |

Figure 29:
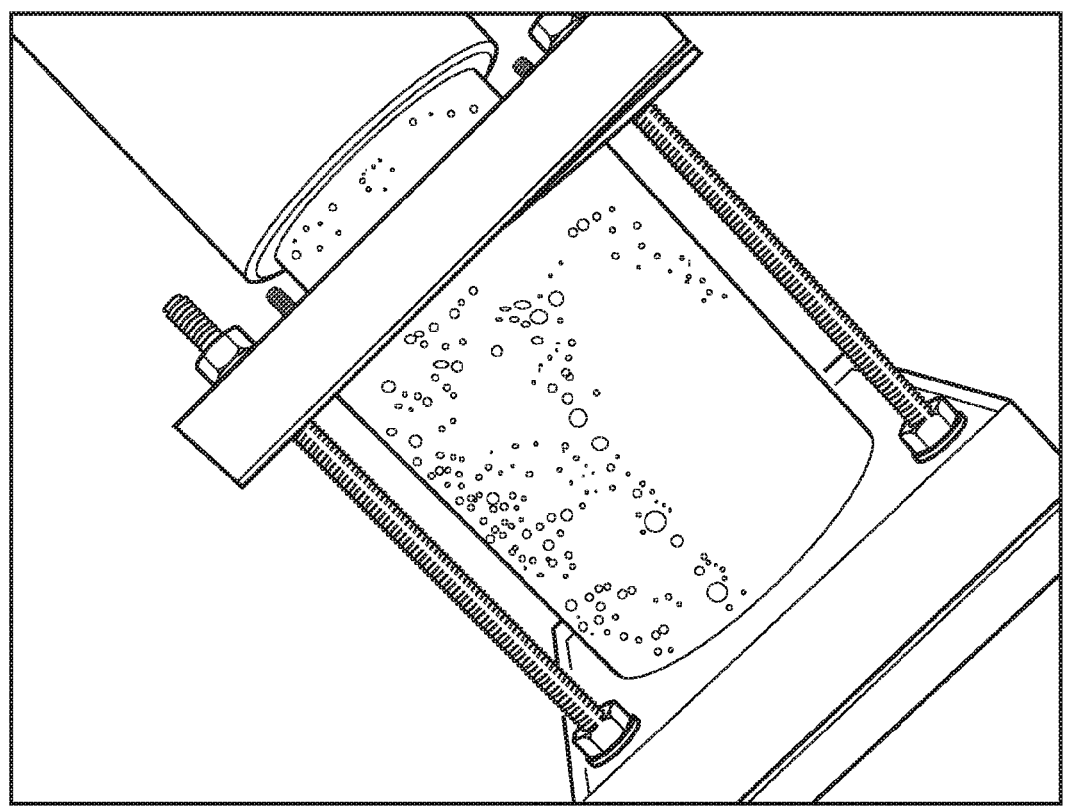
FIG. 29 is a photograph showing oil droplets stuck on the internal wall of the cell chamber.
Figure 30:
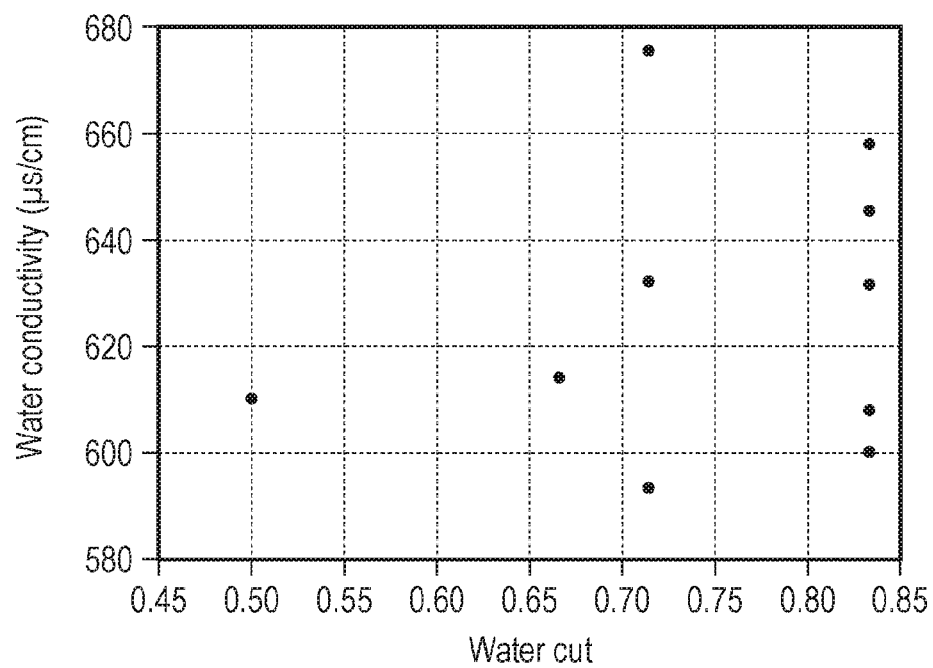
FIG. 30 shoes the correlation between water cut and water conductivity in an embodiment.

Because oil density is much closer to water density, the separation of oil and water in the chamber might not as good as that of air and water. As shown in FIG. 29, the oil droplets stuck on the internal wall of the chamber but the electrodes beneath the metal mesh were not covered by the oil droplets. It is concerned that these oil droplets will affect the accuracy of conductivity reading. The water cut against water conductivity is plotted in FIG. 30. There is no correlation demonstrated between two variables, which indicate that the conductivity cell functions well regardless of oil concentration.

CONCLUSIONS

The variation of water conductivity deteriorates the performance of EIT in the practical industrial process measurement. Two on-line calibration methods are applied to eliminate this effect. The first method indirectly calibrates conductivity by monitoring temperature, but temperature coefficient might introduce extra error. A novel conductivity cell structure is designed to directly on-line measure the conductivity of water in the multiphase flow. In the cell chamber, each phase is separated by the different density and water phase was circulated and conductivity is sampled. The experimental results demonstrate this conductivity cell functions well for air-water two-phase flow and air-oil-water three-phase flow.

REFERENCES FOR SUB-SECTION 3

HAYASHI, M., (2004), Temperature-Electrical Conductivity Relation of Water for Environmental Monitoring and Geophysical Data Inversion, *Environmental Monitoring and Assessment*, 96, 1-3, pp. 119-128.
OLERNI, C., JIA, J. and WANG, M. (2013) "Measurement of Air Distribution and Void Fraction of an Upward Air-water Flow Using Electrical Resistance Tomography and Wire-mesh Sensor", *Measurement Science and Technology*, 24, 3.
SHARIFI, M and YOUNG B., (2013) Towards an online milk concentration sensor using ERT: Correlation of conductivity, temperature and composition, Journal of Food Engineering, 116, 1, pp. 86-96.

Comments on Sub-Section 3

This describes and illustrates in its figures further details of further embodiments of the invention. In particular, it describes and illustrates details of conductivity sensors which may be incorporated in embodiments of the invention. Two such conductivity sensors are illustrated in FIG. 24

Description Sub-Section 4

Certain embodiments of the invention provide methods and devices for visualising and measuring ⅔ phase (gas and/or oil in water, solids and/or gas in water) multiphase flow. One embodiment provides a multi-phase flow instrument for non-invasively measuring the phase flow rates, and rapidly imaging the flow-field distributions, of complex, unsteady two- or three-phase flows (see FIG. 1). The embodiment is based on a method of partial imaging with limited measurements (PILM) of Electrical Impedance Tomography (EIT) combined with an Electromagnetic flowmeter (MF) in conjunction with auxiliary differential-pressure, temperature and conductivity measurements, providing rapid imaging speed, e.g. 10,000 dfps (dual frame per second). It can provide a measurement of volumetric flow rates in two and three phase flows, and alternatively, image time-dependent distributions of the local axial velocity and volume fraction of the dispersed and continuous phases, visualise flow patterns. Novel methods in terms of calibration and compensation are built in the instrument, providing an excellent capability to adopt various industrial environments. The instrument addresses demands of industries for the management of productivity in many industrial sectors such as petroleum, petrochemical, food, nuclear and mineral processing.

The embodiment provides new concepts and methods fused with multi-technologies from both science and engineering for two and three phase flow measurement systems, which includes (i) a dual-plane partial region tomography sensing strategy, (ii) associated partial imaging with limited measurements algorithm (PILM), (iii) a flow density metering system (FDM) based on absolute pressure sensors and an empirical model, (iv) on online conductivity sensor, (v) novel calibration methods, (vi) online compensation methods, (vii) multi-modality data fusion methods and (viii) flow data process, visualisation and users' interface methods. For the example of two-phase oil-in-water flow, the PILM methods with EIT technique is used to extract the local volume fraction distribution ($\alpha_d$) and the local flow velocity distribution ($v_d$) of the dispersed phase (oil) in water continuous flow. The mean oil flow rate can be then obtained by Eq. 1 or Eq. 2 below. EMF is used to measure the local velocity distribution ($v_w$) of the continuous water. The local volume fraction distribution ($\alpha_d$) of the non-conducting dispersed phase obtained using PILM is used with the measured water velocity distribution to obtain the water volumetric flow rate [Eq. 3], the same process can be used for solid in water flows. For the example of vertical three phase, water-continuous oil-water-gas flow with assumptions of flow symmetrical in pipeline and negligible oil-water velocity slip, the flow rates of the individual phases can be measured with PILM, EMF and FDM ([Eqs. 3-5]) and the instrument in FIG. 1—the mean phase volume fractions being calculated with the assistance of the fluid density obtained from the online FDM. To adopt various industrial environments, calibrations can use either the manufacture pre-calibrated set-ups or is carried out with (i) zero or (ii) none zero volume fraction of disperse phase, in respect to water only or phase flow, or with (iii) an estimated volume fraction of disperse phase.

Two-Phase Flow Metering Based on PILM and EMF Sensing Techniques

The dispersed phase flow rate $Q_{1,d}^{PILM}$ and water flow rate $Q_{1,w}^{EMF}$ are given by Eqs. 1 and 2 respectively.

$$Q_d^{PILM} = \sum_{i=1}^{M} \alpha_d^{i,PILM} v_d^{i,PILM} A^i \qquad (1)$$

$$Q_d^{PILM+FDM} = A\alpha_d^{FDM} \overline{v}_d^{PILM} \qquad (2)$$

$$Q_w^{EMF} = \sum_{i=1}^{M} (1 - \alpha_d^{i,PILM}) v_w^{i,EMF} A^i \qquad (3)$$

Three-Phase Metering Based on PILM, EMF and FDM Sensing Techniques $$Q_o^{PILM+FDM} = A\overline{\alpha}_o^{FDM} \overline{v}_o^{PILM} \qquad (4)$$

$$Q_g^{PILM+FDM} = A\overline{\alpha}_g^{FDM} \overline{v}_g^{PILM} \qquad (5)$$

In Eqs. 1 to 5, Q, $\overline{\alpha}$ and $\overline{v}$ represent volumetric flow rate, mean volume fraction and mean velocity respectively; $A^i$ and A are areas of the $i^{th}$ pixel and of pipe cross section respectively; M is the total number of pixels in the images reconstructed using PILM and EMF; subscripts indicate phase; superscripts denote the sensing technique(s) and pixel number.

FIG. 1 shows an integrated sensor system for two and three phase flow measurement. The PILM sensors (E1 and E2) consist of electrodes contacted to inner flow, which can be driven by either a voltage or current excitation tomography system. The EMF is indicated as M1. Two absolute pressure sensors (P1 & P2) are used to produce differential pressure for FDM, the temperature sensor (T1) or the online conductivity sensor is also used for online compensating the changes in the water conductivity due to changes in ionic concentration or temperature. Measurements from the absolute pressure and temperature sensors also allow the standard phase volumetric flow rates to be calculated from the measured phase volumetric flow rates.

Comments on Sub-Section 4

This contains further details of certain embodiments of the invention, for example details of the equations used for the calculation of certain parameters of two-phase flow and three-phase flow.

Description Sub-Section 5

This sub-section contains further details on a method to decompose volume fractions of each phase in three-phase flow using the density measurements from a flow density meter, as may be incorporated in certain embodiments of the invention.

It is necessary to derive n phases from at least n independent measurements. In the system, the fluids flow density is derived as an additional independent measurement to PILM and EMF, which makes the three phase measurement possible.

With the fluid density, $\rho^{FDM}$, obtained from FDM, the known densities of each phases, e.g. $\rho_w$, $\rho_o$, $\rho_g$, as the density of water, oil and gas, respectively, and disperse phases to be non-conductive. The similar principle can be applied to disperse phases composed from other materials, e.g. solid and air.

Then, following relations exists:

$$\begin{cases} \rho_w \bar{\alpha}_w + \rho_o \bar{\alpha}_o + \rho_g \bar{\alpha}_g = \rho^{FDM} \\ \bar{\alpha}_o + \bar{\alpha}_g = \bar{\alpha}^{PILM} \\ \bar{\alpha}_w + \bar{\alpha}_o + \bar{\alpha}_g = 1 \end{cases}$$

We have the secondary relationship $$\rho_o \bar{\alpha}_o + \rho_g \bar{\alpha}_g = \rho^{FDM} - \rho_w(1 - \bar{\alpha}^{PILM})$$

Then, the volume fractions of each phase can be derived as, $$\bar{\alpha}_o = \frac{(\rho_w - \rho_g)\bar{\alpha}^{PILM} + \rho^{FDM} - \rho_w}{\rho_o - \rho_g}$$

In case of the gas mass ignorable, $$\bar{\alpha}_o = \frac{\rho_w \bar{\alpha}^{PILM} + \rho^{FDM} - \rho_w}{\rho_o}$$

Then, $$\bar{\alpha}_g = \bar{\alpha}^{PILM} - \bar{\alpha}_o$$

$$\bar{\alpha}_w = 1 - \bar{\alpha}^{PILM}$$

or $$\bar{\alpha}_w = 1 - \bar{\alpha}_g - \bar{\alpha}_o$$

Description Sub-Section 6

This sub-section contains further details and figures relating to features of certain embodiments of the invention. For example, it provides details of the methods and apparatus which may be incorporated in embodiments to enable the use of absolute pressure sensors for the measurement of differential pressure without the use of a hydraulic transmission device.

The differential pressure readings are obtained from the subtraction of two individual absolute pressure sensors along the vertical upward multiphase flow. The void fraction of the dispersed phase is derived from the empirical model based on energy conservation. The flow density is then calculated. This method has benefits of low capital cost and ease of installation and maintenance without the use of hydraulic transmission. In addition, the absolute pressure measured at the particular location can be utilised to calibrate the parameter of gas phase and monitor the working condition of flow loop.

The wet/wet differential pressure sensor with two tubes can be used to measure the differential pressure. The fluid filled in the tubes transmits pressure at each tap for pressure comparison. However, for the gas-liquid two phase flow measurement, the small air bubbles always entering the tube affect the accuracy of readings. The differential pressure sensor with diaphragm seal interface is able to avoid this problem, but the initial calibration process is complex and the maintenance cost is high. The diaphragm gauge pressure sensors manage to measure the pressure inside the loop larger than that of atmosphere, however, because of the working principle of the gauge pressure sensor, it fails to provide the correct readings if the pressure is lesser than atmospheric pressure. In this method, two absolute pressure sensors are mounted along the vertical upward multiphase flow loop.

Figure 31:
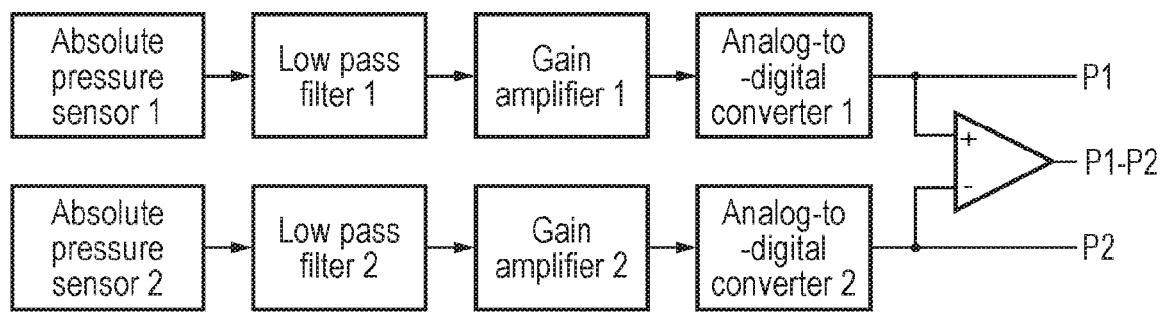
FIG. 31 illustrates signal processing in an embodiment.

The signal conditioning and process of the pressure sensors is illustrated in FIG. 31. Each analogue output of the absolute pressure sensor transmits the low pass filter to block high frequency noise. The amplitude of signal is amplified by the gain amplifier to utilise the sufficient resolution for analog-to-digital converter. At the end, the digitalised absolute pressure P1, P2 and differential pressure P1–P2 are available for the numerical calculation on the later stage.

The subtraction of two absolute pressure readings at positions P1 and P2 in FIG. 1 presents the differential pressure between two locations where the absolute pressure sensor fitted. The front-end interface of the pressure sensor is intrusive but non-invasive with fluids. To ensure the accuracy of differential pressure measurement, the measurement range of two absolute pressure sensors should be assessed and selected carefully. Two sensors need calibration to eliminate systemic measurement error.

Once the differential pressure is determined, the void fraction of the dispersed phase is derived from the empirical model based on energy conservation. The flow density is then calculated. Compared to other methods measuring differential pressure, this method has benefits of low capital cost and ease of installation and maintenance without the use of hydraulic transmission. In addition, the absolute pressure measured at the particular location also can be utilised to calibrate the parameter of gas phase and monitor the working condition of flow loop.

Description Sub-Section 7

This sub-section his gives further details and figures relating to features of certain embodiments of the invention. In particular, this sub-section provides details of how certain embodiments of the invention are able to perform a flow density measurement on a mixed-phase sample, based on differential pressures measured using two pressure sensors arranged at different heights with respect to the sample conduit. This sub-section provides details of a method of online flow density measurement (FDM) based on a differential pressure measurement and a method of empirical compensation A new method of on-line Flow Density Metering using absolute pressure transducers is proposed. A mixture density in a multiphase flow is measured based on the pressure drop along a vertical/inclined pipe section. The pressure drop is obtained from two auxiliary pressure transducers, which are installed on two different tapping points along the pipe section and are separated by a relatively short distance (less than 1 m). Using absolute pressure transducers, unlike conventional differential pressure cells, which employ hydraulic transmission device, offer the advantages such as simplicity in operation, easy to handle and low cost. The relationship between the mixture density and pressure drop along the pipe section is based on Bernoulli's principle of energy conservation. The frictional pressure drop along the pipe section is also taken into account in the calculation of mixture density. The results demonstrate the uncertainty associated with absolute pressure transducers is better than ±5% in two-phase air/water flow. Since many flows of practical engineering interest are steady (or at least steady in the mean); therefore, this novel method can provide a measurement of multiphase mixture density in vertical and inclined pipes. This then can be used for measurement of phase volume fraction and/or calibration purposes. The performance of absolute pressure transducers and the derived model is detailed below.

The Bernoulli equation is an approximate relation between pressure, velocity and elevation. It can be viewed as an expression of mechanical energy balance and can be stated as "The sum of the kinetic, potential and flow energies of a fluid particle is constant along a streamline during steady flow when compressibility and fractional effects are negligible"

The above statement mathematically can be expressed by equation 1:

$$\frac{P}{\rho} + \frac{V^2}{2} + gz = \text{Constant} \tag{1}$$

Equation 1 is commonly used in fluid mechanics for steady, incompressible flow along a streamline in inviscid regions of flow. The value of the constant can be evaluated at any point on the streamline, where the pressure, density, velocity and elevation are known. The Bernoulli equation (in terms of pressure) between any two points, such as point 1 and point 2, as shown in FIG. 32, within a vertical/inclined pipe section, through which a mixture of two- or three-phase flow, can be written as:

$$P_1 + \frac{\rho_m V_1^2}{2} + \rho_m g z_1 = P_2 + \frac{\rho_m V_2^2}{2} + \rho_m g z_2 \tag{2}$$

Figure 32:
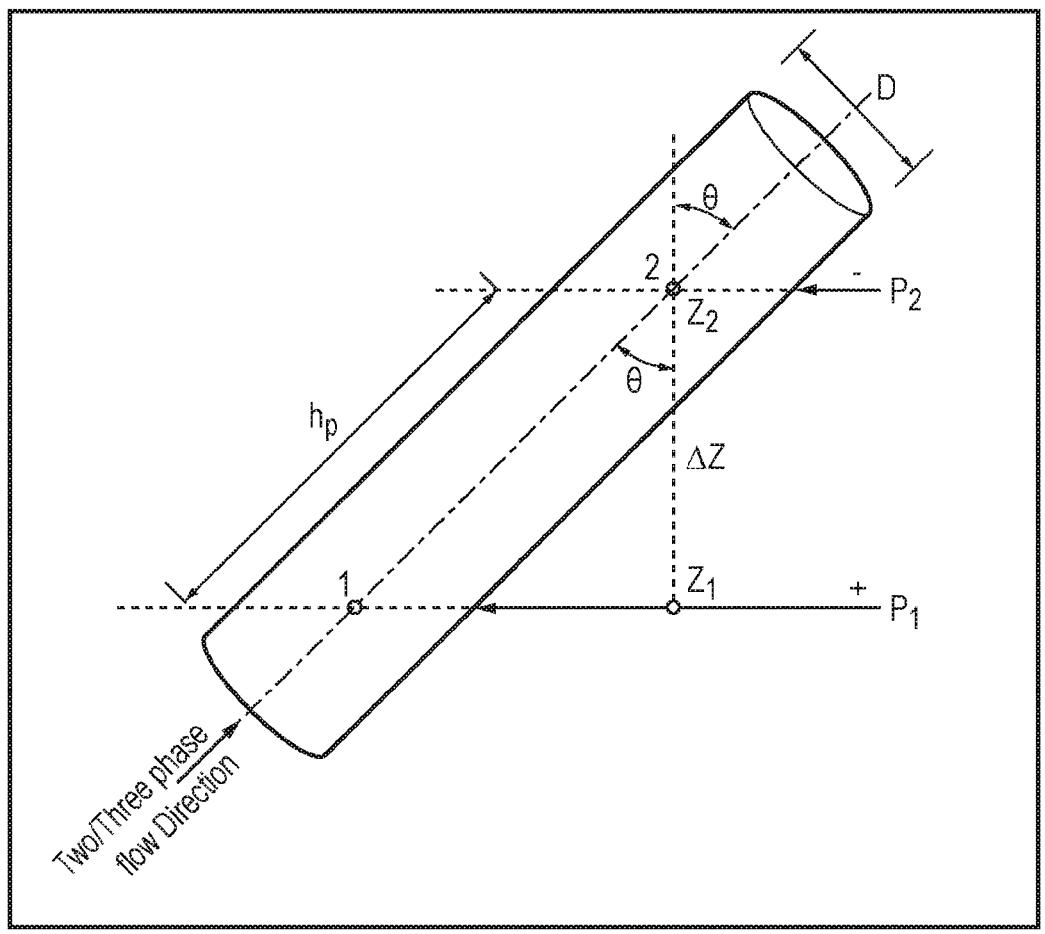
FIG. 32 shows two/three phase flow through an inclined pipe section in an embodiment.

With reference to FIG. 32, in direction of flow, due to friction caused by viscosity of liquid, the sum of total pressure at point 1 is bigger than the sum of pressure at point 2 (i.e. the left-hand side of equation 2 is bigger than the right-hand side). So, in order to compensate to the pressure difference between the two points within the pipe section, a scalar quantity has to be added to the total pressure at point 2 (i.e. to the right-hand side). The scalar quantity, which accounts for the difference between the two points, is called Frictional pressure loss ($F_p$) term between the pressure tapings in a straight pipe section as:

$$P_1 + \frac{\rho_m V_1^2}{2} + \rho_m g z_1 = P_2 + \frac{\rho_m V_2^2}{2} + \rho_m g z_2 + F_p \tag{3}$$

Rearranging equation 3:

$$(P_1 - P_2) + \frac{\rho_m}{2}(V_1^2 - V_2^2) = \rho_m g(z_2 - z_1) + F_p \tag{4}$$

$$(P_1 - P_2) = \Delta P \tag{5}$$

Since the pipe diameter is constant ($V_1 = V_2$), which makes the second term in the left-hand side of equation 4 to be cancelled out.

$$(z_2 - z_1) = \Delta z \tag{6}$$

From FIG. 32;

$$\Delta z = h_p \cos \theta \tag{7}$$

Substituting the above into the equation 4, and rearranging;

$$\rho_m = \frac{\Delta P - F_p}{g h_p \cos \theta} \tag{8}$$

The pressure drop due to frictional losses (or frictional pressure drop-$F_p$) is proportional to pipe length for fully developed flow. The frictional pressure drop can be calculated using equations 9.

$$F_p = \frac{2 C_f \rho_m h_p V_m^2}{D} \tag{9}$$

For smooth pipe, the friction factor is a function of only the Reynolds number, while in rough pipe; the relative roughness ($\varepsilon/D$) also affects the friction factor. Therefore, for turbulent flow in smooth pipes equation 10, the Blasius (1911), equation gives the friction factor accurately for a wide range of Reynolds number, as shown below.

$$C_f = 0.079 Re^{-0.25} \ [4000 < Re < 10^5] \tag{10}$$

On the other hand, for rough pipe and Re<$10^5$ equation 11, Churchill (1977), can be used.

$$C_f = \left[\frac{1}{-4\log\left[\frac{0.27\varepsilon}{D} + \left(\frac{7}{Re_m}\right)^{0.9}\right]}\right]^2 \quad [Re > 4000] \quad (11)$$

$$Re_m = \frac{DV_m\rho_m}{\mu_m} \quad (12)$$

Substituting equation 9 in equation 8 to give:

$$\rho_m = \frac{\Delta P}{h_p\left[g\cos\theta + \frac{2C_f V_m^2}{D}\right]} \quad (13)$$

Equation 13 can be used for calculation of multiphase mixture density in vertical and inclined water continuous upward flow, with considering the following:
The ratio of liquid velocity to the dispersed velocity is unity (i.e. the slip velocity is zero).
The axial pressure tapping separation ($h_p$) is known (0.88 mm in this study).
The mixture density ($\rho_m$) is assumed as density of continuous phase (Water).
$\rho_m = \rho_w = 1000$ kg/m$^3$, at STP 25° C. & 1 bar
The mixture velocity is assumed as continuous phase velocity (Water), which is acquired by the EMF.

$V_m = V_w = V_{EMF}$.

Figure 33:
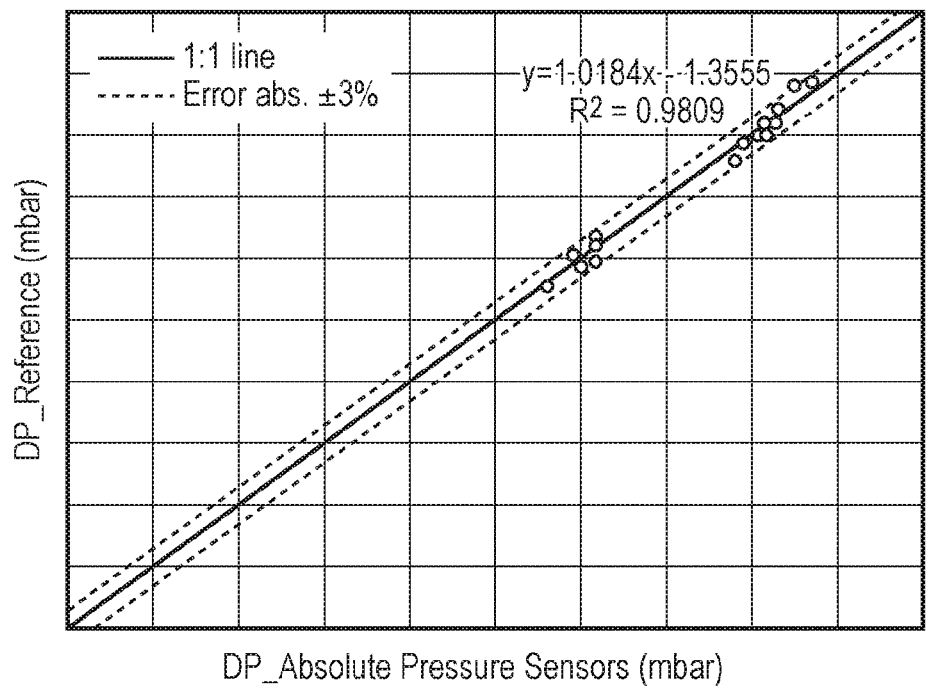
FIG. 33 shows the uncertainty in measured differential pressure using absolute pressure transducers in an embodiment.

The mixture viscosity is assumed as continuous phase viscosity (Water).
$\mu_m = \mu_w = 0.00089$ pa·s, at STP 25° C. & 1 bar Performance of Absolute Pressure Transducers FIG. 33 illustrates the uncertainty associated with the measured differential pressure using absolute pressure transducers in single-phase & two-phase air/water flow (bubble & slug flow). It can be seen that the error is better than 5%.

NOMENCLATURE FOR SUB-SECTION 7

$\rho_m$ Mixture density (kg/m$^3$)
$\theta$ Pipe inclination angle from vertical (degree)
$\varepsilon/D$ Relative roughness
$\varepsilon$ Pipe inner surface roughness (mm)
$\Delta z$ Difference of elevation from between point 1 and point 2 (m)
$\Delta P$ Differential pressure obtained from absolute pressure transducers (Pa)
$z_2$ Elevation head at point 2 (m)
$z_1$ Elevation point at point 1 (m)
z Elevation head (m)
$V_m$ Mixture velocity (m/s)
$V_2$ Fluid velocity at point 2 (m/s)
$V_1$ Fluid velocity at point 1 (m/s)
V Fluid velocity (m/s)
$Re_m$ Mixture Reynolds number
$P_2$ Pressure at tapping point 2 (Pa)
$P_1$ Pressure at tapping point 1 (Pa)
$h_p$ The axial pressure tapping separation (m)
g Gravitational acceleration (9.81 m/s$^2$)
$F_p$ Frictional pressure loss (or frictional pressure drop) (Pa)
D Internal pipe diameter (m)
$C_f$ Fanning friction factor (or friction coefficient)
$\mu_m$ Dynamic mixture viscosity (Pa·s or kg/(s·m))

Description Sub-Section 8

This provides further details on features of certain embodiments of the invention. In particular, it provides details on a method of online correction to the disperse phase volume fraction due to the change of continues phase ionic concentration (conductivity), temperature or using an initial disperse phase volume fraction from FDM without taking conductivity reference measurement.

Two issues are important in the precision of the multiphase flow measurement, which are calibration and compensation. The calibration relates to calibrate the system to the initial reference at its start stage. The compensation is relates to compensate the change of the continuous phase' conductivity due to the change of ionic concentration or temperature. In the application of Electrical impedance tomography, it is always challengeable to take a reference measurement from a zero disperse concentration set-up (e.g. pure water) as one of calibration and to compensate the continuous phase' conductivity variation due to change of ionic concentration or temperature.

Concentration Conversion

The Maxwell relationship is used to convert phase conductivities to the disperse phase volume fraction a from a two phase mixture.

$$\alpha = \frac{2\sigma_1 + \sigma_2 - 2\sigma_{mc} - \frac{\sigma_{mc}\sigma_2}{\sigma_1}}{\sigma_{mc} - \frac{\sigma_2}{\sigma_1}\sigma_{mc} + 2(\sigma_1 - \sigma_2)} \quad (1)$$

where $\sigma_1$ is the conductivity of aqueous continuous phase, $\sigma_2$ is the conductivity of disperse phase and $\sigma_{mc}$ is the mixture conductivity given by EIT. If disperse phase is non-conductive, $\sigma_2$ equals to zero. Then equation (1) can be simplified further:

$$\alpha = \frac{2\sigma_1 - 2\sigma_{mc}}{\sigma_{mc} + 2\sigma_1} \quad (2)$$

Rearrange equation (2), the conductivity ratio $\sigma_{mc}/\sigma_1$ becomes the only variable to determine the void fraction.

$$\alpha = \frac{2 - 2\frac{\sigma_{mc}}{\sigma_1}}{2 + \frac{\sigma_{mc}}{\sigma_1}} \quad (3)$$

The inverse function can be also presented in a mutually same form, $$\frac{\sigma_{mc}}{\sigma_1} = \frac{2 - 2a}{2 + a} \quad (4)$$

Temperature Effect $$\sigma_x = \sigma_{T_{cal}}[1+\lambda(T_x-T_{cal})]$$

where, T is the temperature of the sample, $T_{cal}$ is the calibration temperature.

$$\sigma_1(t_x) = \beta\sigma_0(t_0) \quad (6)$$

where $\beta = [1+\lambda(T_1-T_0)]$.

Ionic Effect

Aspect of the change of ionic concentration not being ignorable, the conductivity due to the change can be expressed as, $$\sigma_1(t_x) = k \cdot \sigma_0(t_0) \quad (7)$$

Density Relationship

The density relationship, for example og gas and oil in water, can be presented as, $$\rho_W(1-\overline{\alpha}_{ERT}) + \rho_O\overline{\alpha}_O + \rho_G\overline{\alpha}_G = \rho_{FDM} \quad (8)$$

The volume fraction measured from ERT can then be expressed as, $$\overline{\alpha}^{ERT} = \frac{\rho_o\overline{\alpha}_o + \rho_g\overline{\alpha}_g + \rho_w - \rho^{FDM}}{\rho_w} \quad (9)$$

For two phase flow, the volume fraction of disperse phase can be presented as, $$\overline{\alpha}_d = \frac{\rho^{FDM} - \rho_w}{\rho_d - \rho_w} \quad (10)$$

Calibration

Since only the relative change of conductivity is used in the data fusion, the actual value of conductivity is less important. The temperature deviation is used for measurement compensation in the system. Therefore, the correctness of temperature measurement or deviation should be checked or calibrated by a calibrated standard temperature meter. The correctness of both absolute and differential pressures is important. They may be calibrated by a set-up with or without a liquid having known density in the system tube. Assuming the flow density to be known or measurable as given by Equation 9 and 10 and the conductivity of the disperse phase is zero, the relative change of conductivity obtained with ERT without the conductivity reference can be simply corrected by the calibration coefficient, $\eta$, at any measurement stage, which is presented as, $$\eta \cdot \frac{\sigma_{mc}}{\sigma_1} = \frac{2-2\alpha}{2+\alpha} \quad (11)$$

Having the relative change measured with ERT at the calibration or any stage, the calibration coefficient can be derived as, $$\eta = \frac{2-2\alpha}{2+\alpha} \cdot \frac{\sigma_1}{\sigma_{mc}} \quad (12)$$

Then, the volume fraction can be derived with the calibration coefficient, $$\alpha = \frac{2 - 2\frac{\eta\sigma_{mc}}{\sigma_1}}{2 + \frac{\eta\sigma_{mc}}{\sigma_1}} \quad (13)$$

Where, $\sigma_{mc}/\sigma_1$ is from ERT measurement. Therefore, it doesn't need to get the reference conductivity.

Compensation

Combining effect from the change of temperature (Equation 6), the compensation can be made as, $$\alpha = \frac{2 - 2\frac{\eta\sigma_{mc}}{\beta\sigma_1}}{2 + \frac{\eta\sigma_{mc}}{\beta\sigma_1}} \quad (14)$$

Combining effect from the change of ionic concentration (Equation 7), the compensation can be made as, $$\alpha = \frac{2 - 2\frac{\eta\sigma_{mc}}{k\sigma_1}}{2 + \frac{\eta\sigma_{mc}}{k\sigma_1}} \quad (15)$$

where $\eta$ density calibration coefficient is taken or estimated at the time of taking reference, but $\beta$ is the temperature deviation coefficient between the times of reference and measurement, and $\kappa$ is the ionbic concentration coefficient.

Description Sub-Section 9

This provides further details of a conductivity meter and method of measuring conductivity which may be incorporated in certain embodiments of the invention. Further features of embodiments of the invention are also described. Methods of online conductivity measurement of water phase in two- or three-phase flow with minimum influence from other phases (gas, oil, solids) are described.

On-line conductivity measurement is a powerful tool for real-time process control, intervention etc. One embodiment is a method of on-line conductivity measurement of background conducting liquid phase (water) in two- or three-phase flows, with no or minimum influence from the other constituent phases (gas, oil or solid). 4-electrode conductivity measurement sensor is designed (FIG. 24) to provide real-time conductivity measurement of conducting liquid phase in vertical upward flow. The method/device overcomes the limitations associated with off-line measurement of water through sampling and provides a real-time conductivity of water for the purpose of conductivity correction or compensation.

One embodiment is a method of on-line conductivity measurement of background conducting liquid phase (water) in two- or three-phase vertical upward flows with no or minimum influence from the other constituent dispersed phases, such as gas, oil and solid particles. The conductivity sensor, shown in FIG. 24, is used for on-line measurement of conductivity. A 4-electrode (stainless steel) sensor is used to measure the conductivity of water accumulated in the measuring cell. The measuring cell used two electrodes, to which an alternating voltage is applied, and then the electrical current, which is directly proportional to the conductivity of the media, is measured through the other pair of electrodes. The electrodes are arranged in an equi-spaced fashion and are in direct contact with the fluid accumulated in the cell. The conductivity cell is coupled with a pipe section through a 45° pipe fitting. Two flanges are fixed at either end of the pipe section to facilitate installation of the conductivity spool in any vertical section of a flow line. The contained fluid within the cell is regularly refreshed via a flexible tube (flush line), which is connected to a low pressure point along the vertical pipe section. A metal screen (mesh) is used to separate the effective measuring area/region (around the electrodes) from fast moving flow and prevent disturbance caused by the other constituent phases. The configuration of the sensor used to measure the conductivity of background liquid phase in a mixture where solid particles exist, differ from the one used for conductivity measurement of conducting liquid phase in a mixture with no solid particles. For flows with solid particles, the conductivity cell is facing the direction of flow (upward) to prevent the accumulation of solid particles in the cell. On the other hand, for flows, where gas is one of the constituent phases, the conductivity cell is facing the opposite direction of flow (downward) to prevent trapping air bubbles in the cell.

Figure 34:
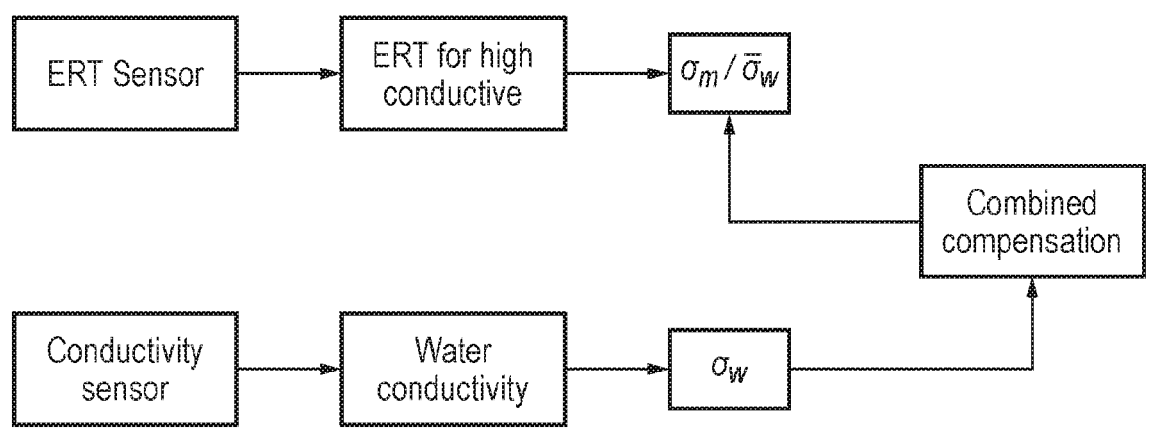
FIG. 34 illustrates part of a system embodying the invention.

The conductivity of the conducting liquid measured on-line is used for real-time compensating the changes in the water conductivity due to changes in ionic concentration or temperature, as shown in FIG. 34.

Description Sub-Section 10

This provides further details on features of certain embodiments of the invention. In particular, it provides details on sensor integration.

One embodiment of the invention is a method of integrating several sub-sensors to obtain a multi-modality measurement system for non-intrusively measuring the phase flow rates, and rapidly imaging the effective flow field distribution of two- or three-phase flows. The measurement principle of the multiphase flow system is based on the multi-modality sensors and multi dimensional data fusion, where all independent flow measurement sub-systems are applied. These sub-systems are, namely a dual-plane Partial Imaging with Limited Measurement sensor (PILM), an off-the-shelf electromagnetic Flow meter (EMF), two absolute pressure transducers, a temperature transducer and a conductivity measuring spool.

One embodiment of the invention is a method of integrating several sub-systems into one robotic, rigid flow meter for metering and imaging two- or three-phase flow. The integrated flow metering system is given in FIG. 17(b). The integrated metering system consists of a dual-plane PILM sensor, an off-the-shelf EMF, two absolute pressure transducers, one temperature sensor and a conductivity measuring spool. All the sub-system are integrated and positioned with consideration to their contribution into the final phase flow rate measurement. The PILM measurement sub-system consists of two planes, at the periphery of which a number of stainless-steel electrodes are mounted. The EMF measurement sub-system uses two or more coils to generate a magnetic field. The effective measuring region of both sensors, the PILM sensor and the EMF, is located in the downstream of the measurement system. Since the phase flow rates are obtained from the PILM sensor and the EMF subsystems, thus they are positioned next to each other, and both of them positioned at the downstream of the whole multi-phase measurement system, to ensure their measurement within a developed flow section. The absolute pressure transducers used to measure the differential change of the pressure in the effective volume of the section, on which the PILM sensor and the EMF are installed. The differential pressure along the PILM sensor section is then used for correction of the PILM reference measurement. Therefore, it is paramount to confine the PILM and the ERT measurement section, one at upstream of the PILM sensor and the EMF measurement section and the other one at downstream. The conductivity measuring spool and the temperature transducer are used for the compensation of conductivity measurement of conductive liquid. Thus, each of them has to be located as close as possible to the PILM sensor. The temperature transducer is positioned at the downstream of the ERT, after the EMF, and the conductivity measuring spool at the upstream, followed by the absolute pressure transducer (low pressure point). The measurement system is enclosed and supported by a metal house. Two flanges are fixed at the two end of the house for pipeline connection.

Description Sub-Section 11

This provides further details on features of certain embodiments of the invention. In particular, it provides a further description of overall framework of the software in terms of operation sequence.

Figure 35:
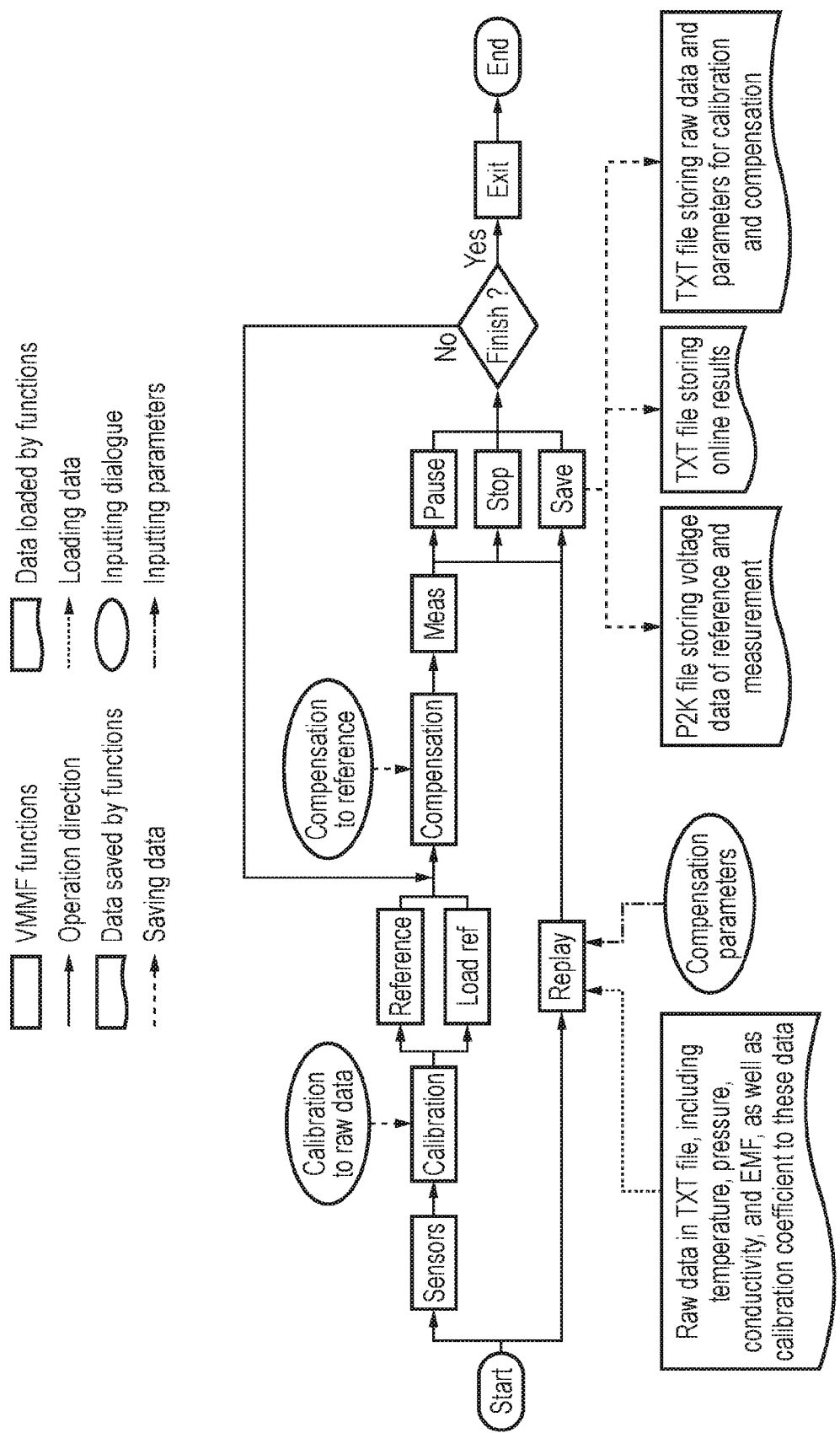
FIG. 35 illustrates the operation sequence of the software in an embodiment.

As FIG. 35 shows, the software can be used for either online flow measurement with block and online mode or replay of existing p2k data, both of which offer user-friendly interaction to users. Moreover, they all allow calibration and compensation to reference data and reconstructed images (conductivity distribution), respectively, with the output of p2k data (both reference and measurement), raw data and the parameters for calibration and compensation, and online results relating to flow measurement in terms of concentration, velocity, and flowrate.

As far as online flow measurement is concerned, it first needs to gauge raw data of EMF, temperature, pressure, and conductivity by auxiliary sensors. Then, by interacting via popup dialogue, calibration parameters are inputted by users and raw data are calibrated for further usage. Afterwards, reference data is taken either by online reference measurement or by loading existing reference file. After compensation to the reference data by the parameters being inputted via user-friendly input dialogue, all required data and parameters are ready to online measurement. During measurement, the computation of flow characteristics (concentration, velocity, and flowrate) is performed in parallel with the sensing of measurement data by EIT, and the intermediate results are displayed. When measuring, users can pause computation, or stop measurement. After measurement, users can save p2k raw data, raw data by auxiliary sensors along with the parameters for calibration and compensation, and the results of online measurement. If finished, users can exit the software, or choose to commit new measurement by repeating "Compensation" and "Meas" functions.

Compared to online flow measurement, replay function is relatively simpler, since there is no need to acquire raw data by auxiliary sensors and obtain reference data. By loading the raw data and relating calibration parameters stored in TXT file, and obtaining the parameters for compensation inputted by users through a popup window, the stored measurement data in p2k file is computed by the exactly same means as the "Meas" function does in online flow measurement. Similar to "Meas" function, the processed results are displayed and further saved.

Description Sub-Section 12

This describes further features of certain embodiments of the invention.

In certain embodiments, software graphically displays the online measurement results, as well as 2-dimension cross-sectional tomograms, of two- and three-phase flow by EIT. As for online measurement results, it contains the profiles of concentration and velocity of dispersed phase, and the mean values of concentration and velocity of continuous phase, as well as the mean flowrate of both dispersed phase and continuous phase.

The online measurement results in certain embodiments present the instantaneous values of concentration, velocity, and flowrate of dispersed phase and continuous phase. More specifically, since the measurement of dispersed phase is primarily based on EIT, its concentration and velocity are presented in terms of profiles containing twenty points, of which the profiles are averaged and calculated based on the parameters inputted by users. Further, the flowrate is displayed based on the concentration and velocity calculated previously. As far as the measurement results of continuous phase are concerned, all results are mean values in terms of concentration, velocity, and flowrate.

On the other hand, the 2-dimension cross-sectional graphs in certain embodiments display the tomograms of the flow at the speed restricted by data acquisition speed of EIT, which allow users to have some realtime information of the flow in terms of conductivity distribution, as well as the performance of EIT. However, the display is optional in certain embodiments and disabled by default for the purpose of increasing measurement precision.

Description Sub-Section 13

This describes further features of certain embodiments of the invention, in particular further information on software to provide users' dialogue interface for flow visualisation and measurement.

The software in certain embodiments provides two popup dialogues to allow users to choose different strategies and then input parameters for calibrating raw data by auxiliary and compensating reference, tomographic results and further concentration results, sensors based on theoretical and/or empirical experience. The dialogues offer user-friendly and easily understandable way for users to interact with the software. Calibration inputting dialogue and compensation inputting dialogue are provided.

The raw data obtained by auxiliary sensors is not gauged at standard level, e.g., temperature and pressure. It therefore needs to be calibrated according to standard values at certain temperature and pressure, for the purpose of decreasing errors. In certain embodiments all raw data is calibrated linearly based on the following equation:

$$[\text{Data}]\_cal = A * [\text{Data}]\_raw + B$$

where A and B are the values input by users. Then, the calibrated values are output for further usage.

As far as compensation is concerned, it contains two separate aspects: one is on reference and the other is on reconstructed images (i.e., conductivity values). Different compensations may be arranged independently and offer users simple input. The reference compensation is based on 3 different strategies, including zero compensation to reference, compensation to reference with known mixture concentration, and compensation to reference by Flow Density Meter (FDM). On the other hand, compensation to reconstructed images also has 3 different ways: non compensated reconstructed images, compensation by temperature without ionic concentration, and compensation based on ionic concentration, each of which is chooseable through the user interface.

Description Sub-Section 14

Summary

Two schemes for measurement from two or three phase flows are described, where the disperse phase can be materials in any kind, in general, as long as they are non-conductive. A typical example for the measurement from gas and oil in water are illustrated in FIG. 3. The schemes are segmented in five parts in terms of sensors, devices, raw data, data fusion and flow quantities finalisation.

Description

Figure 36:
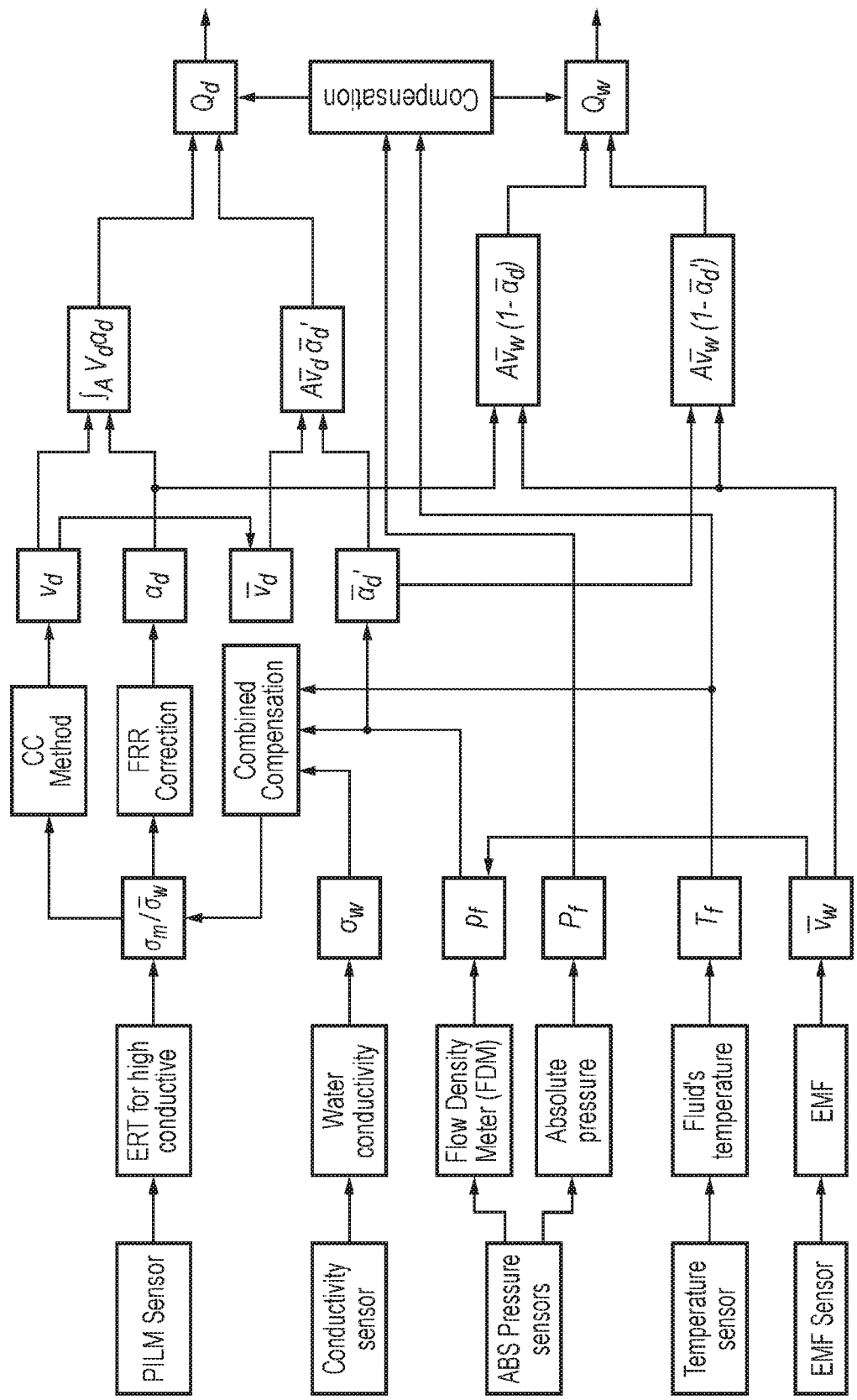
FIG. 36 shows a two phase measurement scheme embodying the invention

FIG. 36 presents the two phase flow measurement scheme. Two key measurements from PILM and FEM with three auxiliary measurements of the online conductivity, temperature and absolute pressure sensors (in the 1st column of FIG. 36) are acquired with relevant devices in the 2nd column in FIG. 36, providing raw measurements of the relative change of conductivity at each imaging pixel, water phase velocity, water conductivity, fluid temperature, density of fluid in flow, absolute pressure inside the pipe at the sensor position, respectively, as shown in the 3rd column of FIG. 36. The relative change of conductivity at each pixel corrected and/or compensated with the online measured water conductivity, fluid density and temperature, provides the disperse phase volume fraction at each pixel, with further correction made by the flow regime recognition (FRR) and correction. The disperse phase velocity at each pixel is derived with the cross-correlation method and the mean velocity is calculated by averaging pixel's velocities. The mean volume fraction can also be derived from the density of flowing fluids with the FDM. These data fusion processes are highlighted in the 4th and 5th columns of FIG. 36. Finally, the flow rate of the continuous phase (water) is calculated using the velocity measured with EMF and volume fraction derived from the difference to the disperse phase. The disperse phase flow rate is calculated with either an integration of the product of pixel volume fractions and velocities over the pipe cross area of the sensing domain or simple products of mean volume fraction and mean velocity as shown in the final two columns of FIG. 36. There are two ways to produce the disperse phase flow rates using either the pixel volume fractions from PILM or the mean value from FDM. The final flow rates are compensated with the online temperature and absolute pressure to the standard reference at 20 □C temperature and 1 bar pressure.

Figure 37:
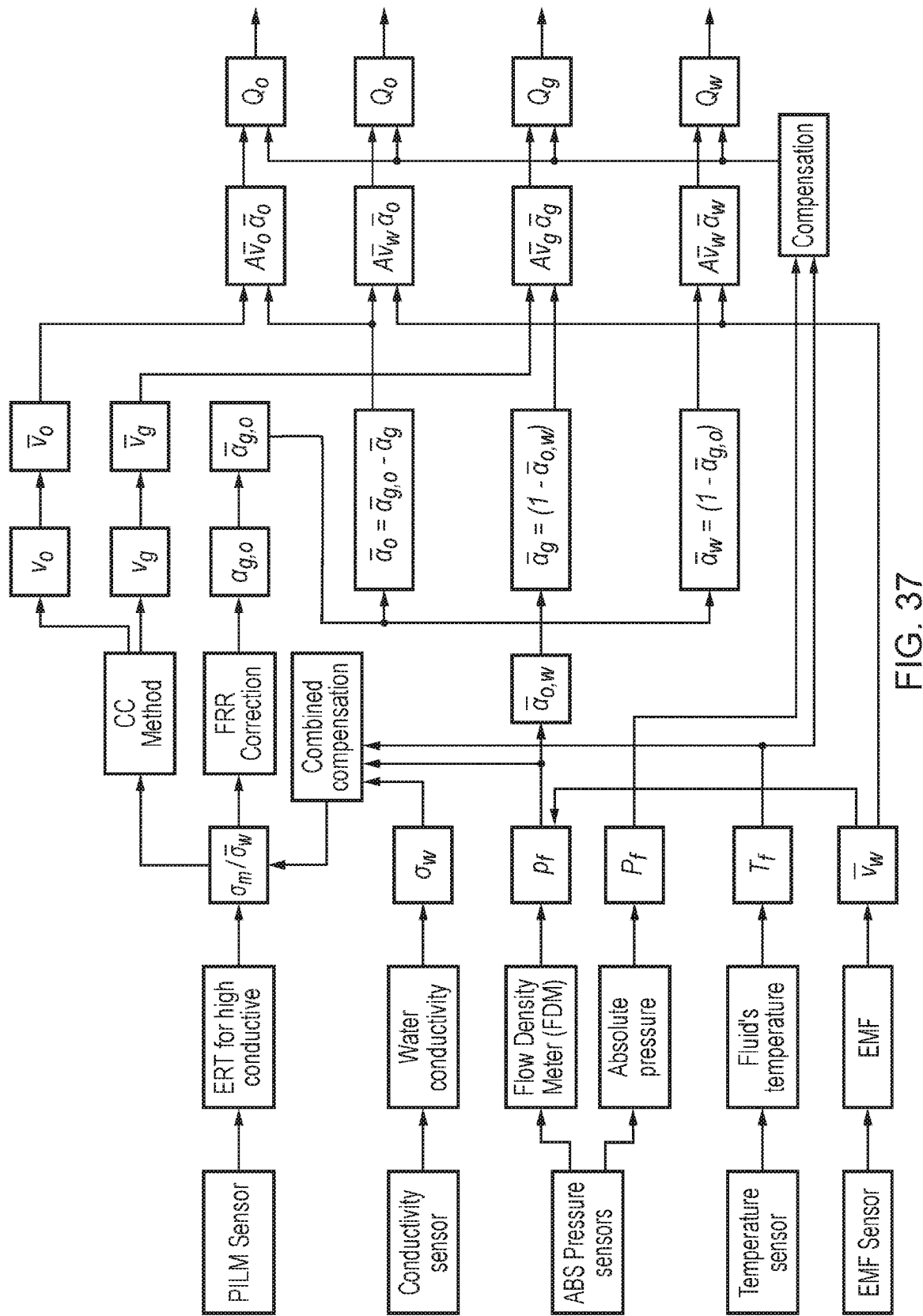
FIG. 37 shows a three phase measurement scheme embodying the invention.

FIG. 37 shows the measurement and data fusion scheme for a gas and oil in water three phase flow. The most process and procedure are the same as described in the two phase flow measurement scheme in FIG. 36, except the decomposition function for third phase shown by the three blocks in the bottom of the 5th column in FIG. 37 and the ways of derive the oil flow rate, which can be obtained from either the cross-correlation method or the use of the water velocity according to relevant circumstances. Both the decomposition method and the oil velocity issue are detailed elsewhere in this specification.

Thus, sub-section 14 describes further details of features of certain embodiments of the present invention. For example, FIG. 36 illustrates the processing of certain sensor signals and data in certain embodiments adapted to monitor a two-phase flow, to calculate or otherwise derive certain parameters of flow. FIG. 37 illustrates the processing of sensor signals and data in certain other embodiments of the invention in order to calculate flow parameters associated with a three-phase flowing sample.

Description Sub-Section 15

This describes features of certain embodiments of the invention. In particular, this sub-section describes an electrode arrangement (or PILM sensor structure incorporating convex electrodes) which may be incorporated in certain tomography apparatus and flow monitoring or measuring systems embodying the invention.

Summary

One aspect of the invention is a novel structure of PILM sensor electrodes to provide self-cleaning and maintain the measurement performance. Each stainless-steel electrode surface is structured to have a convex shape along the length of the sensor plane. The novel electrode self-cleaning and antifouling method is based on increasing the axial flow velocity across the sensor plane cross-section and introducing the electrode surface to a region with higher velocity than that close to the pipe wall. The flowing fluid stream over the convex shaped electrode surface creates a tangential drag force, which prevent deposit formation on the surface of the electrode. The novel structure is addressed to reduce the cost of cleaning and maintenance, increase process reliability and enhance product quality.

Description

Figure 38:
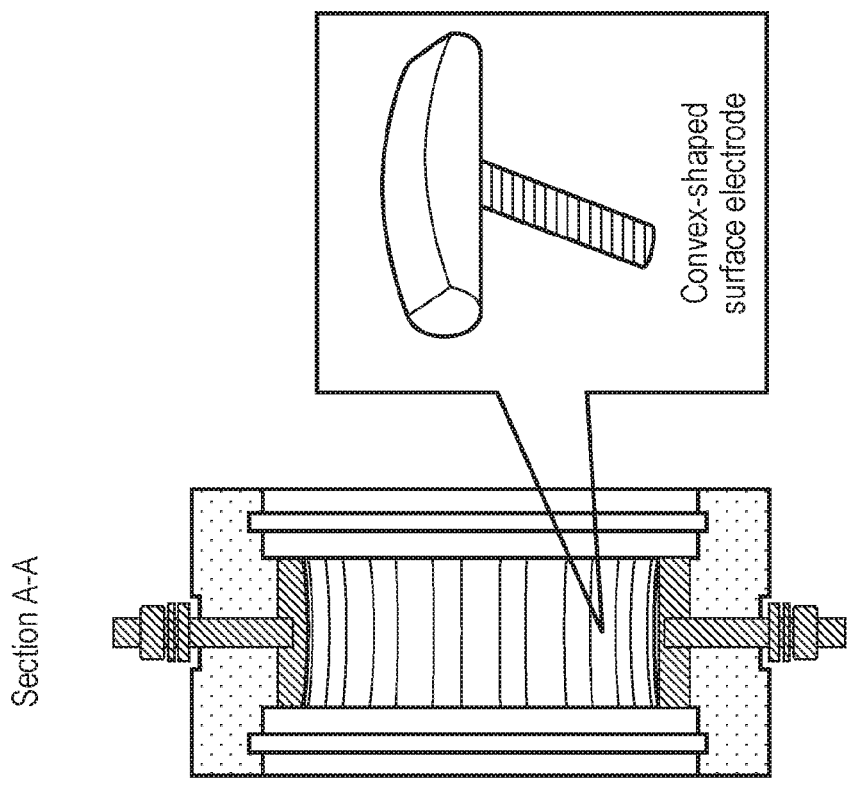
FIG. 38 is a diagram of the PILM sensor plane with electrode surface convex structure in an embodiment.
Figure 38:
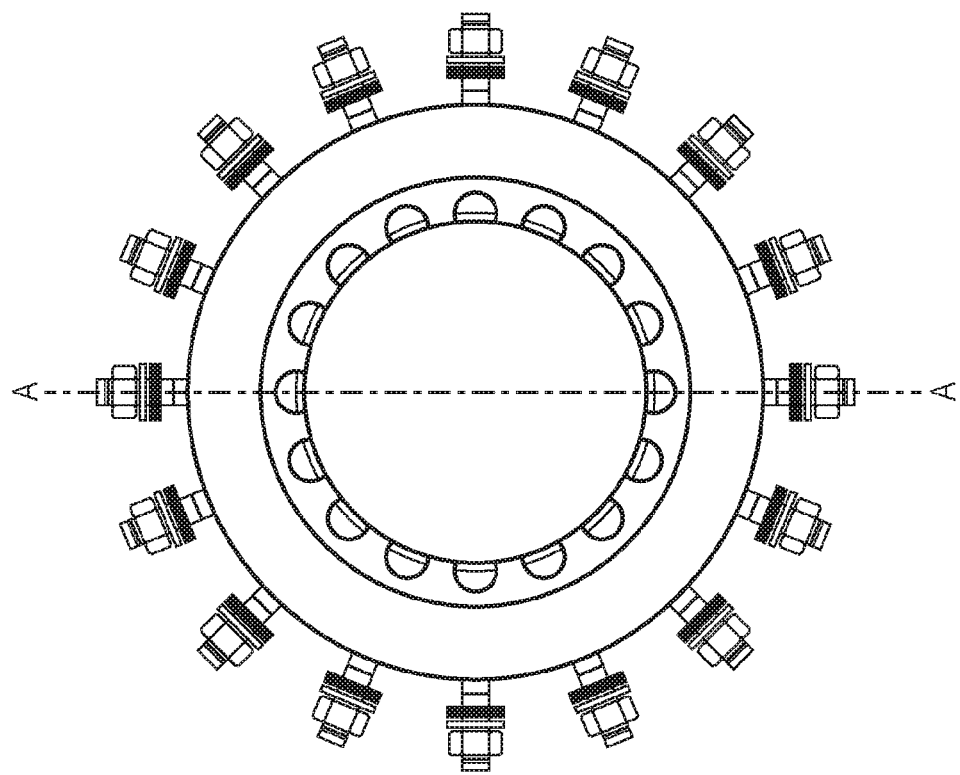

The novel structure of electrode provides a self-leasing method and cleaning optimisation. The method is based on the concept that by increasing the impact force of a tangential stream of fluid on the surface of electrodes can overcome the removal of deposits. The fluid streams over the conventional structure of electrode, which is flush mounted and has a flat surface, has less influence on the removal of the deposits on the surface of each electrode. The influence of removing the deposits can be increased by exposing the surface of each electrode to the faster streams of fluid across the PILM sensor cross-section. FIG. 38 shows the schematic diagram of the PILM sensor plane with electrode surface convex structure. A number of stainless-steel electrodes are mounted at the periphery of the plane, through a threaded bar, which is inserted into the hole at the circumference of the plane. The threaded bar is extended out of the plane to allow the connection of cables using solder tags. Since no economically effective fouling prevention is available in industry, hence the novel structure of the PILM sensor with mounted convex-shaped electrodes can be considered as a mean of reducing cost of cleaning and increase process reliability.

Further Description

It will be appreciated from the above description that certain novel aspects and embodiments of the invention, and features of those certain novel aspects and embodiments, include the following:

Two and Three phase measurements with EIT, EMF and gradiomanometer flow-mixture density metre (FDM) (see, for example, sub-sections 2, 14);

Two phase measurements with EIT, EMF and FDM with either a reference at a water only set-up or the flow-mix density with FDM at any online set-up (see, for example, sub-sections 2, 14);

Differential pressure sensor which can be made with two absolute pressure sensors or one differential pressure sensor for FDM (see, for example, sub-sections 2, 7);

A conductivity measurement chamber with centrifugal and gravitational separation, and fluid refreshing design for compensating the effect of ionic concentration change on flow-mix concentration (see, for example, sub-section 3);

Temperature sensor for compensating the effect of temperature change on flow mix concentration (see, for example, sub-sections 2, 3, 8);

Absolute pressure sensor and temperature sensor for gas mass compensation (see, for example, sub-section 2);

An electrode system with specific design to prevent surface contamination (see, for example, sub-section 15 and/or FIGS. 4-8);

A data acquisition system for cooperating sensors' information (see, for example, sub-section 2);

A computer or microprocessor for data fusion, flow-mix visualisation and monitoring (see, for example, sub-section 2);

Three phase decomposition method with EIT, EMF and FDM (see, for example, sub-section 5);

Calibration method with an initial flow-mix density from FDM or an estimated initial value of the second phase volumetric fraction (see, for example, sub-sections 2, 8);

Compensation method with either the relative change of flow-mix conductivity or temperature (see, for example, sub-section 8);

The integrated two/three phase flow-mix monitoring system (see, for example, sub-sections 1, 2)

The conductivity chamber (see, for example, sub-section 3); and

The electrode system (see, for example, sub-section 15 or FIGS. 4-8).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A flow monitoring system for monitoring flow of a mixed-phase sample comprising at least a first phase and a second phase having different electrical conductivities, the second phase being a liquid or a gas and electrically non-conductive and the first phase being a liquid and having a conductivity higher than the second phase, the system comprising:
 a conduit through which the mixed-phase sample is arranged to flow;
 a tomography apparatus arranged to generate tomography data indicative of at least a first conductivity profile of at least a portion of a first cross section of the mixed phase sample when flowing through the conduit;
 a flow meter arranged to detect flow of the first phase though the conduit and provide a flow signal indicative of a flow velocity of the first phase; and
 a processing means adapted to calculate, from said data, an area fraction of said first cross section occupied by the first phase, and calculate, from said area fraction and said flow signal, a volumetric flow rate of the first phase through the conduit,
 wherein the tomography apparatus comprises:
 a plurality of electrodes each having a respective contact surface arranged to be in electrical contact with a sample flowing through said conduit; and
 the tomography apparatus configured to perform a plurality of measurements on a sample flowing through said conduit to generate said tomography data, each measurement comprising driving a current between a pair of said electrodes and measuring a voltage across another pair of said electrodes,
 wherein at least a portion of each electrode contact surface slopes inwardly, toward a longitudinal axis of the conduit, along the longitudinal axis, such that accumulation of deposits on each said portion is at least partly inhibited by sample flow past each said portion, and
 wherein said plurality of electrodes are evenly spaced around said conduit, and the respective contact surface of each said electrode is flush mounted with an inner surface of the conduit, and has a convex shape along the longitudinal axis,
 such that the plurality of contact surfaces provide a constriction in said conduit to increase axial flow velocity over the convex shaped contact surfaces.

2. The system of claim 1, further comprising a temperature sensor arranged to sense a temperature of the sample flowing though the conduit and provide a temperature signal, indicative of said temperature, to the processing means.

3. The system of claim 1, further comprising a heating means operable to heat at least part of each electrode, wherein each contact surface is a surface of the respective said part.

4. The system of claim 1, further comprising a vibrating means operable to vibrate at least part of each electrode, wherein each contact surface is a surface of the respective said part.

5. The system of claim 1, further comprising conductivity measuring means arranged to measure an electrical conductivity of the first phase of the sample flowing through the conduit and provide a conductivity signal, indicative of the measured conductivity, to the processing means.

6. The system of claim 5, wherein the conductivity measuring means comprises a chamber arranged in communication with the sample-containing volume of the conduit such that when the sample is flowing through the conduit, a portion of the sample collects in the chamber, a plurality of electrodes arranged to be in electrical contact with first phase material collected in the chamber, the plurality of electrodes arranged to drive a current through the collected first phase material and measure a voltage developed across the first phase material.

7. The system of claim 1, wherein said data is further indicative of a second conductivity profile of at least a portion of a second cross section of the mixed phase sample when flowing through the conduit.

8. The system of claim 7, wherein the tomography apparatus comprises a first array of electrodes arranged around said first cross section and a second array of electrodes arranged around said second cross section.

9. The system of claim 7, wherein the processing means is adapted to calculate a volume fraction of the first phase in the sample using said data.

10. The system of claim 7, wherein the processing means is adapted to calculate an axial velocity and a volume fraction of the second phase in the sample using said data.

11. The system of claim 1, wherein the mixed-phase sample comprises a third phase, the third phase being a liquid or a gas, being electrically non-conductive, and having a density different from a density of the second phase, the system further comprising means for measuring a density of the mixed-phase sample flowing through the conduit and generating density data indicative of the density of the mixed-phase sample.

12. The system of claim 11, wherein the second phase is a liquid and the third phase is a gas.

13. The system of claim 11, wherein the processing means is adapted to calculate a volume fraction of the second and/or third phase in the sample using the tomography data.

14. The system of claim 11, wherein the processing means is adapted to calculate a volumetric flow rate of the first phase using the tomography data and electromagnetic flow meter data.

15. The system of claim 11, wherein the processing means is adapted to measure flow-mix density using a flow-mixture density meter.

16. The system of claim 11, wherein the processing means is adapted to calculate a volumetric flow rate of the third phase using tomography data and flow-mixture density data.

17. The system of claim 11, wherein said conduit is arranged with its longitudinal axis substantially vertical, and the means for measuring a density comprises a first pressure sensor arranged at a first height and a second pressure sensor arranged at a second height, each pressure sensor being arranged to sense pressure of the flowing sample in the conduit at the respective height and provide a respective pressure signal, indicative of sample pressure, to the processing means.

18. A flow monitoring method for monitoring flow of a mixed-phase sample comprising at least a first phase and a second phase having different electrical conductivities, the second phase being a liquid or a gas and electrically nonconductive and the first phase being a liquid and having a conductivity higher than the second phase, the system comprising:
arranging the mixed-phase sample to flow through a conduit;
using a tomography apparatus to generate tomography data indicative of at least a first conductivity profile of at least a portion of a first cross section of the mixed phase sample flowing through the conduit;
using a flow meter to detect flow of the first phase though the conduit and generate a flow signal indicative of a flow velocity of the first phase; and
calculating, from said data, an area fraction of said first cross section occupied by the first phase, and calculating, from said area fraction and said flow signal, a volumetric flow rate of the first phase through the conduit,
wherein the tomography apparatus comprises:
a plurality of electrodes each having a respective contact surface arranged to be in electrical contact with a sample flowing through said conduit; and
the tomography apparatus configured to perform a plurality of measurements on a sample flowing through said conduit to generate said tomography data, each measurement comprising driving a current between a pair of said electrodes and measuring a voltage across another pair of said electrodes,
wherein at least a portion of each electrode contact surface slopes inwardly, toward a longitudinal axis of the conduit, along the longitudinal axis, such that accumulation of deposits on each said portion is at least partly inhibited by sample flow past each said portion, and
wherein said plurality of electrodes are evenly spaced around said conduit, and the respective contact surface of each said electrode is flush mounted with an inner surface of the conduit, and has a convex shape along the longitudinal axis,
such that the plurality of contact surfaces provide a constriction in said conduit to increase axial flow velocity over the convex shaped contact surfaces.

19. A tomography apparatus comprising:
a conduit having an interior volume extending along a longitudinal axis and through which a fluid or mixed-phase sample is arranged to flow;
a plurality of electrodes each having a respective contact surface arranged to be in electrical contact with a sample flowing through said interior volume; and
wherein the tomography apparatus is adapted to perform a plurality of measurements on a sample flowing through said interior volume, each measurement comprising driving a current between a pair of said electrodes and measuring a voltage across another pair of said electrodes,
wherein at least a portion of each electrode contact surface slopes inwardly, toward the longitudinal axis, along the longitudinal axis, whereby accumulation of deposits on each said portion is at least partly inhibited by sample flow past each said portion, and
wherein said plurality of electrodes are evenly spaced around said conduit, and the respective contact surface of each said electrode is flush mounted with an inner surface of the conduit, and has a convex shape along the longitudinal axis,
such that the plurality of contact surfaces provide a constriction in said conduit to increase axial flow velocity over the convex shaped contact surfaces.

* * * * *